United States Patent
Nomura et al.

(10) Patent No.: US 9,392,790 B2
(45) Date of Patent: Jul. 19, 2016

(54) MOLECULAR ROADBLOCKS FOR RPON BINDING SITES

(75) Inventors: Christopher T. Nomura, Syracuse, NY (US); Benjamin R. Lundgren, Nampa, ID (US)

(73) Assignee: THE RESEARCH FOUNDATION FOR THE STATE UNIVERSITY OF NEW YORK, Syracuse, NY (US)

( * ) Notice: Subject to any disclaimer, the term of this patent is extended or adjusted under 35 U.S.C. 154(b) by 30 days.

(21) Appl. No.: 14/115,953

(22) PCT Filed: May 7, 2012

(86) PCT No.: PCT/US2012/036746
§ 371 (c)(1),
(2), (4) Date: Jan. 21, 2014

(87) PCT Pub. No.: WO2012/154651
PCT Pub. Date: Nov. 15, 2012

(65) Prior Publication Data
US 2014/0148380 A1    May 29, 2014

Related U.S. Application Data

(60) Provisional application No. 61/483,350, filed on May 6, 2011.

(51) Int. Cl.
| | | |
|---|---|---|
| A61K 38/00 | (2006.01) | |
| C07K 16/00 | (2006.01) | |
| A01N 37/46 | (2006.01) | |
| C12N 15/63 | (2006.01) | |
| C12N 9/12 | (2006.01) | |
| C12Q 1/68 | (2006.01) | |

(52) U.S. Cl.
CPC .............. *A01N 37/46* (2013.01); *C12N 9/1247* (2013.01); *C12N 15/63* (2013.01); *C12Q 1/6897* (2013.01)

(58) Field of Classification Search
None
See application file for complete search history.

(56) References Cited

U.S. PATENT DOCUMENTS

| 6,004,803 | A | 12/1999 | Klatzmann et al. |
| 6,994,985 | B1 | 2/2006 | Werner et al. |
| 7,517,684 | B2 * | 4/2009 | Rubenfield et al. ........... 435/325 |
| 2003/0023032 | A1 | 1/2003 | Bassler et al. |
| 2004/0157314 | A1 | 8/2004 | Bergeron et al. |
| 2007/0020624 | A1 * | 1/2007 | Rubenfield ............ C07K 14/21 435/6.15 |

FOREIGN PATENT DOCUMENTS

WO    2004/056960 A2    7/2004

OTHER PUBLICATIONS

Thompson, et. al. The alternative sigma factor RpoN regulates the quorum sensing gene rhlI in Pseudomonas aeruginosa, FEMS Microbiology Letters, 220 (2003) 187-195.*
Kelly, Journal of Bacteriology. 2000, p. 6503-6508vol. 182, No. 22.*
Thompson et. al. FEMS Microbiology Letters 220 (2003) 187-195.*
International Search Report and Written Opinion issued in PCT/US2012/036746, mailed Dec. 26, 2012.
Thompson et al., "The alternative sigma factor RpoN regulates the quorum sensing gene rhlI in *Pseudomonas aeruginosa*," *FEMS Microbiology Letters*, 220:187-195 (2003).

* cited by examiner

*Primary Examiner* — James Alstrum-Acevedo
*Assistant Examiner* — Jeanette Lieb
(74) *Attorney, Agent, or Firm* — Heslin Rothenberg Farley & Mesiti P.C.

(57) ABSTRACT

The present invention relates to, inter alia, a method for repressing transcription and/or gene expression from RpoN binding sites (or promoters) or cryptic promoters upstream of RpoN binding sites. The method comprises providing an agent that specifically and selectively binds to RpoN promoter sequences to inhibit or repress the expression of genes downstream of that promoter; and contacting the RpoN promoter with the agent. Agents for repressing transcription and/or gene expression from RpoN promoters are also provided. The agent can be a composition that binds specifically to the −24, −12, or −24/−12 site(s) for RpoN promoter interference. Synthetic peptides, vectors, and host cells are also provided.

13 Claims, 25 Drawing Sheets

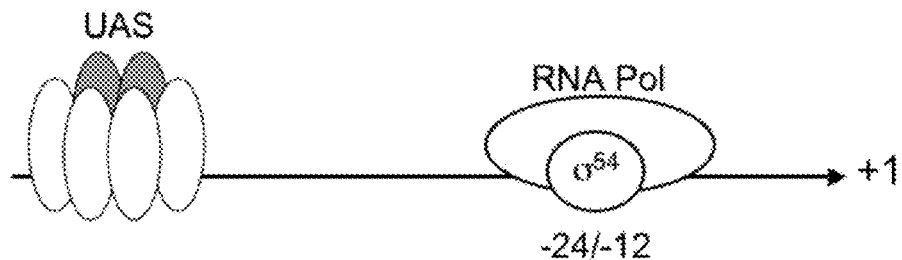
FIG. 1
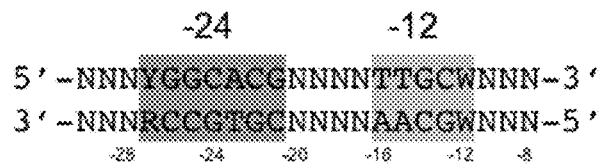
FIG. 2
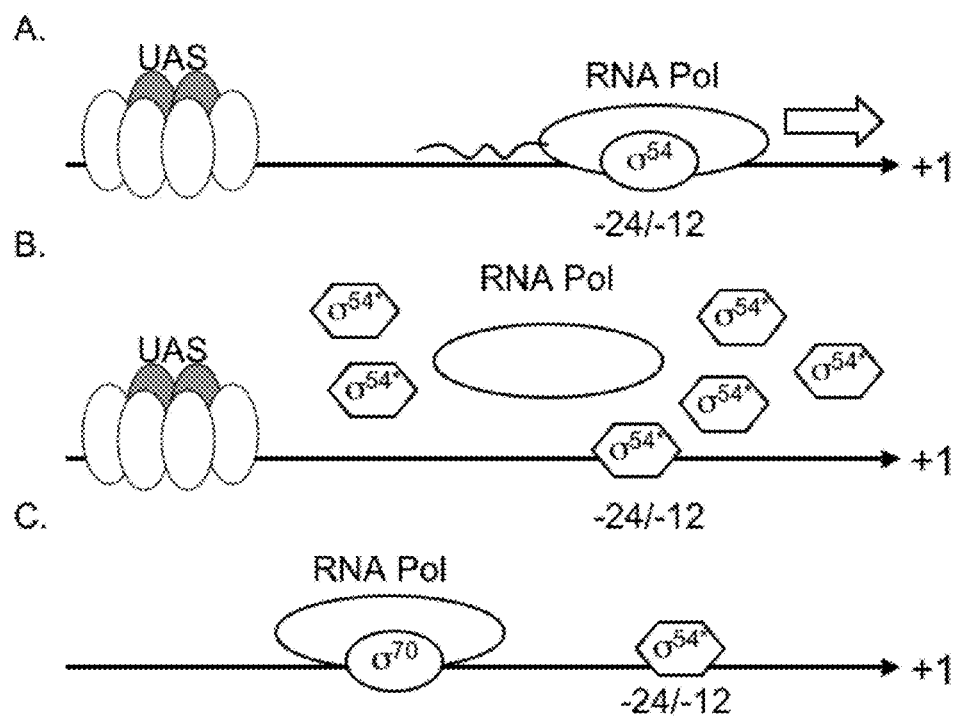
FIGS. 3A-C

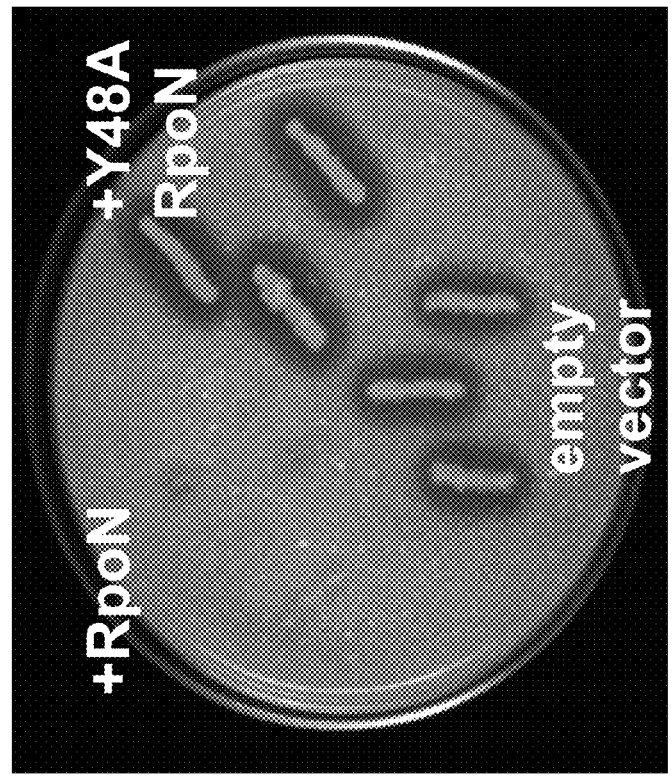
FIG. 9

RpoN-deficient bacterium: | With the RpoN molecular roadblock:
---|---

A. Genes can be transcribed by other promoters

*Cryptic promoters can activate RpoN-regulated genes*

B. Cannot detect antagonistic RpoN interactions i. at $\sigma^{70}$ promoters

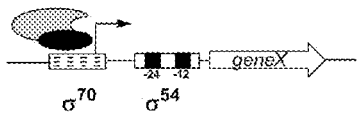

ii. with activator protein from RNAP:$\sigma^{70}$

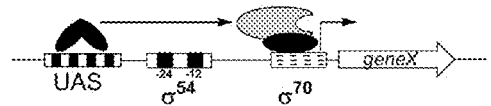

C. Higher RNAP:$\sigma^{70}$ increases transcription from $\sigma^{70}$ promoters

*sigma factor RNAP imbalance generates bias transcription data*

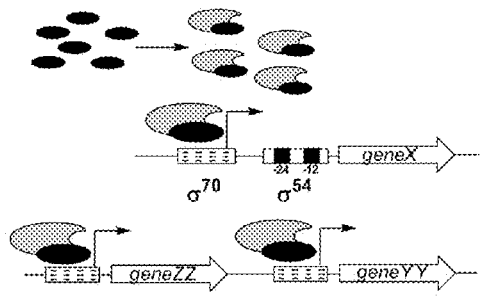

D. Genes are blocked from multiple promoters

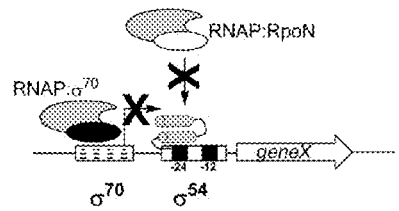

E. Antagonistic interactions can be observed i. blocking $\sigma^{70}$ promoters

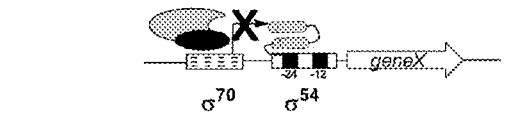

ii. blocking activator protein from RNAP:$\sigma^{70}$

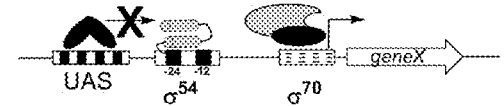

F. RNAP:sigma factor complexes are in normal balance

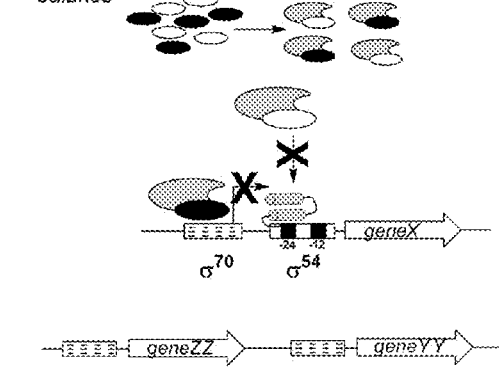

FIG. 19

|  |  | Downfold-change | |
| --- | --- | --- | --- |
| Genes | Function | ΔrpoN | wt |
| PhzA2B2C2D2E2F2 | phenazine biosynthesis | -9 | -62 |
| PA1677 | Isochorismatase hydrolase | -5 | -2 |
| PA2069 | carbamoyltransferase | -4 | -6 |
| PA1869 | acyl carrier protein | -3 | -3 |
| OprG | outer membrane protein | -3 | -5 |
| PA1414 | hypothetical | -3 | -2 |
| Ppa | inorganic pyrophosphatase | -3 | -2 |
| PA4141 | hypothetical | -3 | -10 |
| PA3326 | hypothetical | -3 | -4 |
| PA1342 | amino acid transport | -3 | -12 |
| RhlR | QS transcriptional regulator | -3 | -4 |
| PA4463 | sigma 54 modulation protein | -3 | -4 |
| Idh | isocitrate dehydrogenase | -3 | NC |
| RhlA | rhamnosyltransferase | -2 | -5 |
| PckA | PEP carboxykinase | -2 | NC |
| PA2321 | glucokinase | -2 | NC |
| PA2805 | hypothetical | -2 | -4 |
| PA3309 | universal stress protein | -2 | -3 |
| PA2067 | hydrolase | -2 | -3 |
| PA2031 | hypothetical | -2 | -4 |
| PA0200 | hypothetical | -2 | -33 |
| PA4348 | metallo-beta-lactamase superfamily protein | -2 | NC |
| GlyA3 | serine hydroxymethyltransferase | -2 | NC |
| PA0542 | hypothetical | -2 | -3 |
| AlgP | alginate regulatory protein | -2 | -3 |
| Anr | anaerboic transition | -2 | -2 |
| PA0102 | carbonic anhydrase | -2 | NC |
| PA2604 | hypothetical | -2 | -10 |
| PA0459 | ClpA/B protease ATP binding subunit | -2 | -6 |
| PA5445 | succinyl-CoA:coenzyme A transferase | -2 | 2 |
| AceA | isocitrate lyase | -2 | -2 |
| PA3665 | LysE transporter | -2 | NC |
| Rmf | ribosome modulation factor | -2 | -10 |

FIG. 28

MOLECULAR ROADBLOCKS FOR RPON BINDING SITES

CROSS-REFERENCE TO RELATED APPLICATIONS

This application is a U.S. National Phase filing under 35 U.S.C. §371 of International Application No. PCT/US2012/036746, filed May 7, 2012, and published as WO 2012/154651-A2 on Nov. 15, 2012, which claims benefit of priority from U.S. Provisional Patent Application Ser. No. 61/483,350, filed May 6, 2011. The entire contents of each of the prior applications are incorporated herein by reference in their entirety.

GOVERNMENT RIGHTS STATEMENT

This invention was made with Government support under grant number DMR0907085 awarded by the National Science Foundation. The Government has certain rights in the invention.

SEQUENCE LISTING

The instant application contains a lengthy Sequence Listing which has been submitted via text file (.txt) in lieu of a printed, paper (or .pdf) copy, and is hereby incorporated by reference in its entirety.

FIELD OF THE INVENTION

The present invention relates to molecular roadblocks for RpoN binding sites and uses thereof, including, inter alia, methods and tools for repressing gene transcription by targeting promoter activity. The invention further relates to agents, synthetic peptides, vectors, and host cells for repressing gene transcription.

BACKGROUND OF THE INVENTION

Bacterial pathogens cause a number of important diseases of humans, animals, and plants. Bacteria also contribute to the growth of unwanted biofilms, which can cause biofouling of coatings, water sources, and microbial influenced corrosion. The average bacterium has ~3500 genes that must be coordinately expressed in order for the organism to grow and respond to the environment. Therefore, understanding gene expression in bacteria is an important aspect in developing ways to control diseases and other problematic issues caused by bacteria.

Currently, there is a global rise in microbial resistance to antibiotics. The rapid evolution of resistant bacteria and the slow development of new antibiotics underscores the urgent need for new and innovative approaches to decrease microbial pathogenicity. Most traditional antibiotics act in one of two fashions: either as bacteriostatics that prevent bacterial cell division or as bactericides that kill the cell. Recently, there has been a movement to target quorum sensing (QS) since this does not control processes essential for the survival or growth of the cells (Njoroge et al., 2009, EMBO Mol Med 1(4): 201-210). All currently available antibiotics target a single process for the bacterial cells, e.g., cell wall synthesis, protein synthesis, quorum sensing, etc.

Since these methodologies target single cellular functions or structures, microbes can often evolve to evade the treatment. In addition, there is a dearth of defined targets to inhibit or limit bacterial response to the environment. There is therefore a need in the art for new approaches that address the limitations associated with traditional antibiotics. In particular, there is a need in the art for methods that can specifically interfere with the expression of genes involved in pathogenesis, motility, bacterial communication, biofilm production, and bacterial response to environmental stimuli.

The present invention is directed to overcoming these and other deficiencies in the art.

Citation or identification of any reference in this section, or in any other section of this application, shall not be considered an admission that such reference is available as prior art to the present invention.

SUMMARY OF THE INVENTION

The present invention relates to various methods, agents, compositions, synthetic peptides, and other tools that are effective in, inter alia, repressing gene transcription in bacteria. Gene expression in bacteria requires specialized proteins called sigma factors that direct the RNA polymerase (RNAP) to sites of transcription. Most sigma factors belong to the $\sigma^{70}$ family. Whereas bacteria have multiple $\sigma^{70}$-type sigma factors, they normally only have one functional copy of the alternative sigma factor, $\sigma^{54}$ or RpoN. The alternative sigma factor, $\sigma^{54}$ or RpoN, regulates a complex genetic network that extends into various facets of bacterial physiology, including metabolism, survival in strenuous environments, production of virulence factors, and formation of biofilms. And although RpoN is essential for expression of these phenotypic traits, definition of the transcriptional network governed by RpoN is limited to few examples, which focused on predictive models or expression of full-length native RpoN to identify sites of regulation.

In one aspect, to circumvent the inherent shortcomings of these approaches and gain global insight into RpoN regulation, the present invention provides, inter alia, a DNA-binding protein called the RpoN molecular roadblock that specifically targets RpoN promoters. The RpoN molecular roadblock antagonizes transcription from all genes possessing RpoN promoters thereby providing a genome-wide, temporal snapshot of RpoN regulation. The RpoN molecular roadblock of the present invention is useful for defining RpoN regulons for bacterial pathogens, including opportunistic pathogens, by using a combination of microarray transcriptome analysis and computational prediction. Use of the RpoN molecular roadblock of the present invention also is useful for identifying unprecedented control points for RpoN regulation. Also, because of the universal nature of RpoN transcription, the RpoN molecular roadblock of the present invention can be applied to any bacterium and will serve as an advantageous tool for discovering RpoN genetic networks.

The methods, agents, synthetic peptides, vectors, and host cells of the present invention can be used in medical, agricultural, and bioprocess industries and applications. For example, the present invention can be used to reduce or prevent biofilms produced by bacteria, as many of the genes encoding proteins associated with biofilm synthesis are regulated by RpoN promoters. Further, a number of plant and animal (including human) diseases are caused by pathogenic bacteria, which rely on virulence factors.

Further, since RpoN is a global transcriptional regulator and is necessary for full virulence in several human bacterial pathogens, the present invention provides important methods and tools useful to discover cryptic promoters and genes regulated by RpoN. By using the method to inhibit expression of genes regulated by RpoN promoters, genes can be identified via comparisons using art-known transcriptome analyzing technologies (e.g., real time sequencing, quantitative real time PCR (QRT PCR), microarray analysis).

The present invention can also be used to improve bioprocess applications such as protein and bioproduct production by decreasing metabolic burden of RpoN expressed genes in cells. By eliminating unnecessary burden from RpoN expressed genes, more energy can go towards bioproduct production.

Thus, in one aspect, the present invention relates to a method for repressing transcription or gene expression from a binding site of interest, where the binding site of interest is an RpoN binding site or a cryptic promoter upstream or downstream of an RpoN binding site. The method involves the steps of: (a) providing an agent that (i) specifically and selectively binds to a sequence comprised in the binding site of interest and (ii) inhibits or represses expression of genes regulated by the binding site of interest; and (b) contacting the agent to the binding site of interest. In some embodiments, said contacting comprises contacting the agent to a bacterial cell comprising the binding site of interest, wherein the agent is heterologous to the bacterial cell.

In another aspect, the present invention relates to an agent for repressing transcription and/or gene expression from a binding site of interest, where the binding site of interest is an RpoN binding site or a cryptic promoter upstream of an RpoN binding site.

In another aspect, the present invention relates to a composition comprising an agent for repressing transcription and/or gene expression, bound to a binding site of interest, where the binding site of interest is an RpoN binding site or a cryptic promoter upstream of an RpoN binding site. In some embodiments, the composition further comprises a bacterial cell comprising the agent bound to the RpoN binding site or a cryptic promoter upstream of an RpoN binding site, wherein the agent is heterologous to the bacterial cell.

In another aspect, provided herein is a composition comprising a bacterial cell comprising a heterologous agent bound to an RpoN binding site or a cryptic promoter upstream of an RpoN binding site, wherein said agent represses transcription and/or gene expression from the RpoN binding site or a cryptic promoter upstream of an RpoN binding site.

As used herein, the term "heterologous" refers to what is not normally found in nature. Accordingly, the term "heterologous agent" refers to an agent, for example, a heterologous protein, not normally found in a given cell in nature. As such, a heterologous agent may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) naturally found in the host cell but positioned outside of its natural locus (e.g., an exogenous polynucleotide comprising a native gene sequence but encoding a heterologous protein).

In some embodiments, the heterologous agent bound to an RpoN binding site or a cryptic promoter upstream of an RpoN binding site can be any agent capable of repressing transcription and/or gene expression from an RpoN binding site or a cryptic promoter upstream of an RpoN binding site, as provided herein.

In some embodiments, the heterologous agent comprises: a synthetic peptide comprising an amino acid sequence that: (a) has 70-75%, 75-80%, 80-85%, 85-90%, 90-95% or 95-100% homology with an RpoN box of Region III of an RpoN protein; and (b) binds specifically to a −24, −12, or −24/−12 site(s) of an RpoN promoter, where the synthetic peptide is effective for repressing transcription and/or gene expression from a binding site of interest, and where the binding site of interest is an RpoN binding site or a cryptic promoter upstream of an RpoN binding site. In some embodiments, the amino acid sequence comprises the conserved amino acids from an RpoN box of Region III of an RpoN protein through the carboxy terminal amino acid residue of the RpoN protein. In some embodiments, the Region III comprises a modification to the heptad repeat overlapping the glutamine-rich or acid-rich motifs of an RpoN protein. In some embodiments, the amino acid sequence comprises at least 20 carboxy terminal amino acids of an RpoN protein. In some embodiments, the amino acid sequence binds specifically and selectively to a cryptic promoter upstream of an RpoN binding site. In some embodiments, the amino acid sequence comprises SEQ ID NO:10103 or a functional variant thereof. In some embodiments, the heterologous agent comprises an isolated nucleic acid molecule encoding the synthetic peptide described above. In some embodiments, the nucleic acid molecule comprises the nucleotide sequence of SEQ ID NO:10102.

In a further aspect, the present invention relates to a method for identifying an agent for repressing transcription or expression of a gene of interest from a promoter of interest, where the promoter of interest comprises an RpoN binding site or a cryptic promoter upstream of an RpoN binding site. The method comprises the steps of: (a) transforming an expression vector into a bacterial cell of interest, where the expression vector comprises a reporter gene operably linked to a promoter comprising an RpoN binding site or a cryptic promoter upstream of an RpoN binding site; and (b) determining the expression of the reporter gene in the absence and presence of a candidate agent, respectively. In some embodiments, the candidate agent is identified as an agent for repressing transcription or expression of a gene of interest from an RpoN binding site or a cryptic promoter upstream of an RpoN binding site when expression of the reporter gene is modulated in the presence of the candidate agent. In some embodiments, the identified agent decreases expression of the reporter gene. In some embodiments, the bacterial cell of interest does not comprise a native RpoN protein.

In another aspect, the present invention relates to a method for identifying an RpoN −24 conserved nucleotide sequence element for use in a screening assay, where the screening assay screens for an agent of interest that binds to the RpoN −24 conserved nucleotide sequence. This method involves the steps of: (a) transforming a bacterial cell with an expression vector comprising a reporter gene, where the vector comprises a −24 nucleotide sequence element comprising GTTGGXXXXTT (where X is any nucleotide) positioned between a promoter and a ribosomal binding site (RBS) for the reporter gene; (b) contacting an RpoN protein or peptide to −24 element nucleotide sequence of the reporter gene construct; and (c) determining whether transcription mediated by the reporter gene promoter is impeded, thereby reducing expression of the reporter gene. In some embodiments, the −24 nucleotide sequence element comprising GTTGGXXXXTT is identified as an RpoN −24 conserved nucleotide sequence element when expression of the reporter gene is reduced.

In a further aspect, the present invention relates to a synthetic peptide comprising an amino acid sequence that: (a) has 70-75%, 75-80%, 80-85%, 85-90%, 90-95% or 95-100% homology with an RpoN box of Region III of an RpoN protein; and (b) binds specifically to a −24, −12, or −24/−12 site(s) of an RpoN promoter, where the synthetic peptide is effective for repressing transcription and/or gene expression from a binding site of interest, and where the binding site of interest is an RpoN binding site or a cryptic promoter upstream of an RpoN binding site.

In another aspect, the present invention relates to an isolated nucleic acid molecule encoding the synthetic peptide of the present invention.

In another aspect, the present invention relates to a vector comprising the isolated nucleic acid molecule encoding the synthetic peptide of the present invention.

In another aspect, the present invention relates to a host cell comprising the vector of the present invention.

In another aspect, the present invention relates to a method of using the synthetic peptide of the present invention for repressing transcription or gene expression from a binding site of interest, where the binding site of interest is an RpoN binding site or a cryptic promoter upstream or downstream of an RpoN binding site. The method involves the steps of: (a) providing the synthetic peptide according to the present invention; and (b) contacting the synthetic peptide to the binding site of interest, thereby repressing transcription or gene expression from the binding site of interest.

BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1: Schematic of organization of RpoN ($\sigma^{54}$)-dependent promoters and activators. The RpoN ($\sigma^{54}$) protein binds to a specific nucleotide sequence binding site (promoter) located −24/−12 to the initiation site. Once bound, it recruits the RNA polymerase (RNA Pol). Specific activator proteins called enhancer binding proteins (EBPs) that bind to upstream activating sequences (UAS) are necessary activate transcription from the RpoN binding site.

FIG. 2: Consensus nucleotide sequence of the $\sigma^{54}$ binding site. The −24 (dark gray box) and −12 (light gray box) consensus sequences are shown. N, any nucleotide; R, purines; Y, pyrimidines; W is A or T.

FIGS. 3A-3C: Schematic of one embodiment. A. Normal transcription from the RpoN ($\sigma^{54}$) promoter as depicted in FIG. 1. B. Use of a compound, non-native, mutant protein, synthetic peptide, or other chemical compound capable of binding the RpoN promoter sequence (indicated by the hexagon $\sigma^{54*}$) that can antagonize transcription by the RNA polymerase. Once bound, the protein is unable to interact with the RNA polymerase or activator proteins, thus preventing transcription of the RpoN-specific locus. Multiple copies of the $\sigma^{54*}$ will titer out the RpoN promoter sites therefore repressing the transcription of all loci regulated by RpoN. C. In cases where genes or operons have more than one promoter, the $\sigma^{54*}$ can inhibit expression by physically blocking RNA polymerase holoenzyme associated with another sigma factor (in this example it is a $\sigma^{70}$ type sigma factor, but it may be any sigma factor that promotes transcription from upstream of the molecular roadblock. In some cases, the repression of the expressed gene will result in a lack of transcription from genes that would be under control of the repressed gene. For example, if the gene were an activator of transcription of other genes on the genome, the $\sigma^{54*}$ would prevent expression of that gene and any genes under its control. On the other hand, the blockage of a repressor would result in the expression of other genes in the genome, not normally expressed under those particular conditions.

FIG. 9: *P. aeruginosa* PAO1 growth on LB plates with 2% milk when expressing i) pBRL344 (empty vector), ii) truncated RpoN, or iii) Y48A RpoN.

FIG. 28: Genes that are antagonistically regulated by RpoN in *P. aeruginoisa*. To identify sites of antagonism via RpoN, the RpoN molecular roadblock was expressed in rpoN-deficient *P. aeruginosa*. The resulting transcriptome was then compared to a transcriptome generated by rpoN-deficient *P. aeruginosa* harboring empty plasmid. Genes displaying a magnitude of more than 2-fold change and possessing putative RpoN binding sites were categorized as sites of RpoN antagonism (ArpoN column). For comparison, relative fold changes are given for comparing the transcriptomes between wild-type *P. aeruginosa* with and without the RpoN molecular roadblock (wt column).

DETAILED DESCRIPTION OF THE INVENTION

Figure 4:
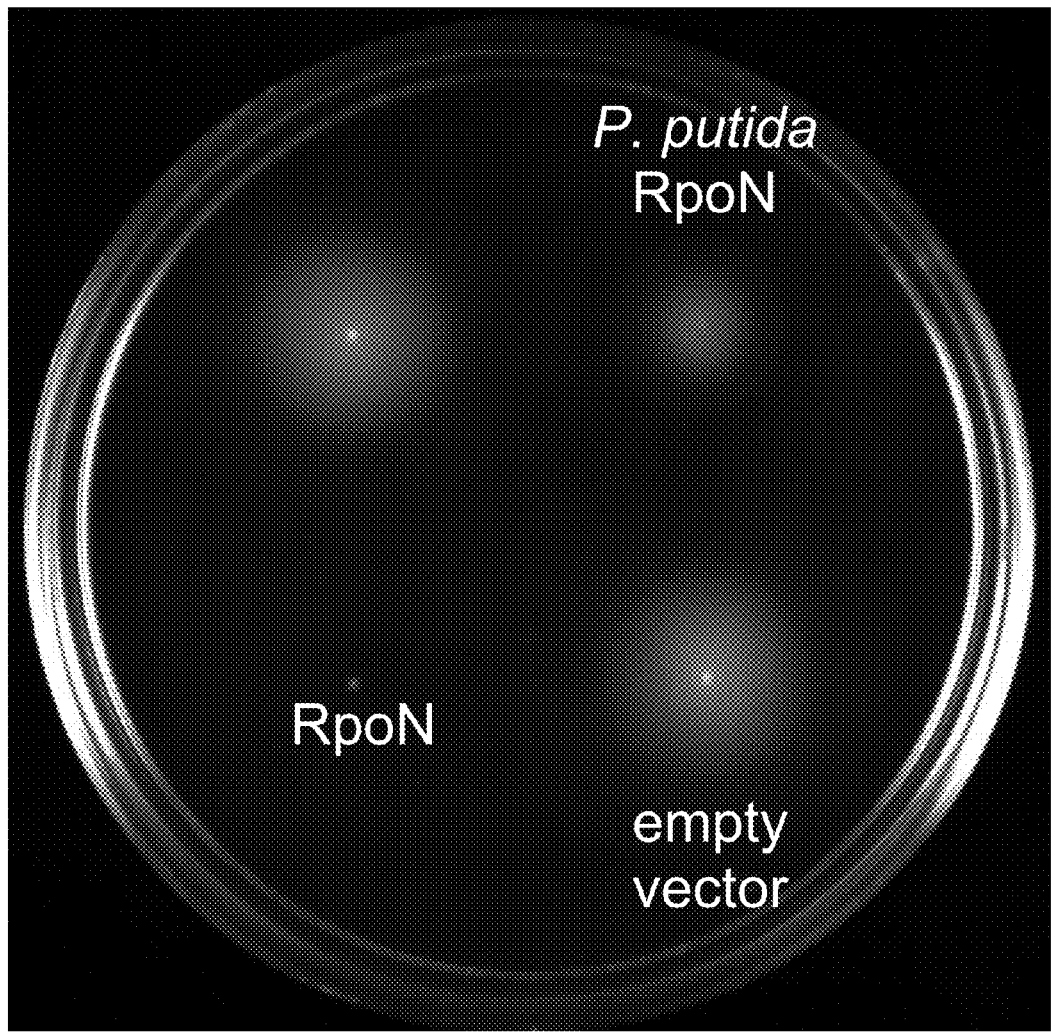
FIG. 4: Motility of *P. putida* KT2440 on M63 soft agar expressing i) empty vector, ii) native RpoN or iii) *M. xanthus* RpoN.

The present invention relates to molecular roadblocks for RpoN binding sites and uses thereof, including, inter alia, methods and tools for repressing gene transcription by targeting promoter activity. The invention further relates to agents, synthetic peptides, vectors, and host cells for repressing gene transcription.

Sigma Factors and RpoN ($\sigma^{54}$)

Sigma factors (a) are prokaryotic proteins that are necessary for transcription of prokaryotic genes. Sigma factors bind to specific nucleotide sequences in the DNA usually located −35/−10 and sometimes extended −10 from the initiation site called promoters and recruit the RNA polymerase to initiate transcription of specific genes (Gruber et al. 2003, Annu Rev Microbiol 57:441-466). Most sigma factor proteins belong to the RpoD or $\sigma^{70}$ family of proteins based on sequence similarity.

The alternative sigma factor RpoN (also known as $\sigma^{54}$, sig54, $\sigma^{N}$, NtrA, SigL) is a protein that also directs transcription in prokaryotic cells but is completely unrelated to the $\sigma^{70}$ family of proteins (Burrows, P. C., K. Severinov, A. Ishihama, M. Buck, and S. R. Wigneshweraraj. 2003. Mapping sigma 54-RNA polymerase interactions at the −24 consensus promoter element. J Biol Chem 278:29728-43). Although the RpoN protein also binds to a very specific nucleotide sequence binding site (−24/−12) and recruits the RNA polymerase in order to initiate transcription of specific genes, it must work in concert with transcriptional activators that often bind to a specific enhancer nucleotide sequences that are not located near the RpoN binding site (or promoter). These activators are a broad class of ATP activated proteins that allow the RpoN initiated transcription from a −24/−12 binding site to occur (FIG. 1). Thus, in contrast to the $\sigma^{70}$ family of proteins, whose members promote transcription from the −35/−10 sites and do so independently of an ATP energy source (Murakami, K. S., and S. A. Darst. 2003. Bacterial RNA polymerases: the whole story. Curr Opin Struct Biol 13:31-9), RpoN proteins must bind to their promoter and undergo a conformational change in the presence of specific ATP activated proteins to form an open transcription complex.

The RpoN protein has been shown to activate transcription of genes encoding proteins involved in nitrogen utilization and in pilin-, flagella-, and virulence-related factors in both plant and animal pathogens (Cases, I., D. W. Ussery, and V. de Lorenzo. 2003. The sigma54 regulon (sigmulon) of *Pseudomonas putida*. Environ Microbiol 5:1281-93; Hendrickson, E. L., J. Plotnikova, S. Mahajan-Miklos, L. G. Rahme, and F. M. Ausubel. 2001. Differential roles of the *Pseudomonas aeruginosa* PA14 rpoN gene in pathogenicity in plants, nematodes, insects, and mice. J Bacteriol 183:7126-34; Studholme, D. J., and M. Buck. 2000. The biology of enhancer-dependent transcriptional regulation in bacteria: insights from genome sequences. FEMS Microbiol Lett 186: 1-9). The protein interacts with a specific, conserved nucleotide sequence, the RpoN ($\sigma^{54}$) promoter or binding site (FIG. 2). The sequence is remarkably conserved with some nucleotides in the −24 and −12 sites>90% conserved across a number of bacterial species (Barrios, H., B. Valderrama, and E. Morett. 1999. Compilation and analysis of sigma(54)-dependent promoter sequences. Nucleic Acids Res 27:4305-13).

FIG. 2 shows a consensus sequence for an RpoN binding site. SEQ ID NOS. 1-9999 (which are 5'-3' sequences) and the 3'-5' complementary sequences thereof, are examples of consensus sequences for RpoN binding sites that can be targeted using the methods of the invention. In one instance, the consensus sequence is −12 from the initiation site. In another embodiment, the consensus sequence is located 20-600 bp from the initiation site.

In another instance, the consensus sequence is 20-30 nucleotides in length. In other instances, the consensus sequence can be 20, 21, 22, 23, 24, 25, 26, 28, 29 or 30 nucleotides in length and can comprise a sequence that has 70-75%, 75-80%, 80-85%, 85-90%, 90-95% or 95-100% homology with any one of the sequences set forth in SEQ ID NOS. 1-9999. Furthermore, it will be understood by the skilled artisan that the sequences set forth herein and in SEQ ID NOS. 1-9999 are 5'-3' sequences, and that the complementary 3'-5' set of consensus sequences are also contemplated as targets according to the methods disclosed herein.

The RpoN proteins as a class are divided into three regions (Wigneshweraraj, S. R., S, Nechaev, K. Severinov, and M. Buck. 2002. Beta subunit residues 186-433 and 436-445 are commonly used by Esigma54 and Esigma70 RNA polymerase for open promoter complex formation. J Mol Biol 319:1067-83). Region I located near the N-terminus interacts with the enhancer binding proteins (EBPs) necessary to activate transcription. Region II is a linking region. Region III contains subdomains that interact with the RNA polymerase and very highly conserved sequences that are involved in binding the −24/−12 binding (promoter) site on the DNA known as the RpoN box (Doucleff, M., J. G. Pelton, P. S. Lee, B. T. Nixon, and D. E. Wemmer. 2007. Structural basis of DNA recognition by the alternative sigma-factor, sigma54. J Mol Biol 369:1070-8). Because of the lack of homology in Region I among RpoN proteins from various bacterial species, it is likely that this region would be species specific for proper interactions with EBPs. Region II has even less homology cross species. On the other hand, Region III, with its high degree of conserved primary sequence, likely interacts with RpoN promoters regardless of species or primary sequence of Region I and Region II. It has been shown previously that overexpression of RpoN leads to growth inhibition in bacteria, but the cause of this is unknown (Sasse-Dwight, S., and J. D. Gralla. 1990. Role of eukaryotic-type functional domains found in the prokaryotic enhancer receptor factor sigma 54. Cell 62:945-54).

The present invention relates to a method for repressing transcription or gene expression from a binding site of interest, where the binding site of interest is an RpoN binding site or a cryptic promoter upstream or downstream of an RpoN binding site. The method involves the steps of: (a) providing an agent that (i) specifically and selectively binds to a sequence comprised in the binding site of interest and (ii) inhibits or represses expression of genes regulated by the binding site of interest; and (b) contacting the agent to the binding site of interest.

In one embodiment, the agent binds specifically to a −24, −12, or −24/−12 site for RpoN promoter interference.

In another embodiment, the RpoN binding site comprises a sequence selected from the group consisting of SEQ ID NOS. 1-9999 and the 3' to 5' complementary base pairs thereof.

In another embodiment, the agent comprises an amino acid sequence encoding a native or mutant RpoN protein.

In another embodiment, the agent is provided by heterologously expressing a native or mutant RpoN protein.

In another embodiment, the RpoN protein comprises a sequence selected from the group consisting of SEQ ID NOS. 10000-10093. In some embodiments, the RpoN protein consists (or consists essentially) of a sequence selected from the group consisting of SEQ ID NOS. 10000-10093.

In another embodiment, the agent comprises an amino acid sequence encoding a $\sigma^{54}$ ("sig54") protein.

In another embodiment, the agent is provided by heterologously expressing the $\sigma^{54}$ ("sig54") protein.

In another embodiment, the agent comprises an amino acid sequence encoding an RpoN protein comprising a modification to the heptad repeat overlapping the glutamine-rich or acid-rich motifs.

In another embodiment, the agent comprises an amino acid sequence encoding a stabilized cyclic peptide or fusion protein.

In another embodiment, the agent binds specifically and selectively to the cryptic promoter.

In another embodiment, the agent is a synthetic peptide from 20 to 600 amino acids in length.

In another embodiment, the synthetic peptide comprises at least 20 carboxy terminal amino acids of an RpoN protein.

In another embodiment, the synthetic peptide comprises the conserved amino acids from an RpoN box of Region III of an RpoN protein through the carboxy terminal amino acid residue of the RpoN protein.

In another embodiment, the synthetic peptide has 70-75%, 75-80%, 80-85%, 85-90%, 90-95% or 95-100% homology with an RpoN box of Region III of an RpoN protein.

In another embodiment, Region III comprises a modification of the heptad repeat overlapping the glutamine-rich or acid-rich motifs.

In another embodiment, bacterial cell motility is inhibited, bacterial cell growth is inhibited, bacterial quorum sensing is inhibited, bacteria are killed, bacterial attachment is inhibited, bacterial virulence is inhibited, bacterial wilt disease is prevented, or bacterial extra polysaccharide production is inhibited as a result of repression of transcription and/or gene expression from an RpoN binding site or a cryptic promoter upstream of an RpoN binding site by the agent within the bacterial cell.

In another embodiment, the inhibition of bacterial cell motility, the inhibition of bacterial cell growth, the inhibition of bacterial quorum sensing, the killing of bacteria, the inhibition of bacterial attachment, the inhibition of bacterial virulence, the prevention of bacterial wilt disease or the inhibition of bacterial extra polysaccharide production is temporally controlled through induction.

The present invention also relates to an agent for repressing transcription and/or gene expression from a binding site of interest, where the binding site of interest is an RpoN binding site or a cryptic promoter upstream of an RpoN binding site.

In one embodiment, the agent binds specifically to a −24, −12, or −24/−12 site(s) for RpoN promoter interference.

In another embodiment, the agent induces overexpression of a native or mutant RpoN protein.

In another embodiment, the agent comprises a $\sigma^{54}$ ("sig54") protein.

In another embodiment, the agent comprises a modification to the heptad repeat overlapping the glutamine-rich or acid-rich motifs of an RpoN protein.

In another embodiment, the agent comprises a stabilized cyclic peptide or fusion protein.

In another embodiment, the agent binds specifically and selectively to a cryptic promoter upstream of an RpoN binding site.

In another embodiment, the agent is a synthetic peptide from 20 to 600 amino acids in length.

In another embodiment, the synthetic peptide comprises at least 20 carboxy terminal amino acids of an RpoN protein.

In another embodiment, the synthetic peptide comprises the conserved amino acids from an RpoN box of Region III of an RpoN protein through the carboxy terminal amino acid residue of the RpoN protein.

In another embodiment, the synthetic peptide has 70-75%, 75-80%, 80-85%, 85-90%, 90-95% or 95-100% homology with an RpoN box of Region III of an RpoN protein.

In another embodiment, Region III comprises a modification of the heptad repeat overlapping the glutamine-rich or acid-rich motifs.

Also provided herein is a composition comprising an agent for repressing transcription and/or gene expression, bound to a binding site of interest, where the binding site of interest is an RpoN binding site or a cryptic promoter upstream of an RpoN binding site. In some embodiments, the composition further comprises a bacterial cell comprising the agent bound to the RpoN binding site or a cryptic promoter upstream of an RpoN binding site, wherein the agent is heterologous to the bacterial cell.

Also provided herein is a method for identifying an agent for repressing transcription or expression of a gene of interest from a promoter of interest, where the promoter of interest comprises an RpoN binding site or a cryptic promoter upstream of an RpoN binding site. The method comprises the steps of: (a) transforming an expression vector into a bacterial cell of interest, where the expression vector comprises a reporter gene operably linked to a promoter comprising an RpoN binding site or a cryptic promoter upstream of an RpoN binding site; and (b) determining the expression of the reporter gene in the absence and presence of a candidate agent, respectively. In some embodiments, the candidate agent is identified as an agent for repressing transcription or expression of a gene of interest from an RpoN binding site or a cryptic promoter upstream of an RpoN binding site when expression of the reporter gene is modulated in the presence of the candidate agent. In some embodiments, the identified agent decreases expression of the reporter gene. In some embodiments, the bacterial cell of interest does not comprise a native RpoN protein. In one embodiment, the promoter of interest is a sigma 70 (sig70, σ70) type promoter.

In another embodiment, the present invention provides a method for identifying an agent for repressing transcription or expression of a gene of interest from a promoter of interest, where the promoter of interest is an RpoN binding site or a cryptic promoter upstream of an RpoN binding site, the method comprising: (a) transforming a vector into a first wildtype strain and a first rpoN-deficient strain of a bacterial strain of interest, wherein the vector is an expression vector that expresses a candidate agent; and (b) transforming a vector into a second wildtype strain and a second rpoN-deficient strain of the bacterial strain of interest, wherein the vector is a parental empty vector of the expression vector of step (a). In some embodiments, the candidate agent comprises a candidate synthetic RpoN peptide.

This embodiment can further include the steps of: growing the first and second wildtype strains and the first and second rpoN-deficient strains (e.g., under identical conditions); isolating total RNA from the first and second wildtype strains and the first and second rpoN-deficient strains after the induction of expression of the candidate agent (e.g., a candidate synthetic RpoN binding protein (or peptide)); preparing cDNA libraries from mRNA isolated from total RNA from the first and second wildtype strains and the first and second rpoN deficient strains after the induction of expression of the candidate agent; using the cDNA libraries: in independent real-time sequencing experiments to identify the sequences of all total transcripts produced, thereby obtaining data concerning the identity of the transcripts, or to create labeled sequences to be used in microarray (gene chip) assays to evaluate expression of a transcriptome of the bacterial strain of interest, thereby obtaining data concerning the expression the transcriptome; analyzing the data obtained for similarities or differences in expression; comparing the first and second wildtype strains with the first and second rpoN-deficient strains to identify genes that are transcribed from previously cryptic promoters; and determining whether a transcriptome for an RpoN binding site or a cryptic promoter upstream of an RpoN binding site is present. In some embodiments, the candidate agent is identified as an agent for repressing transcription or expression of a gene of interest from an RpoN binding site or a cryptic promoter upstream of an RpoN binding site when a transcriptome is present.

The present invention also relates to a method for identifying an RpoN −24 conserved nucleotide sequence element for use in a screening assay, where the screening assay screens for an agent of interest that binds to the RpoN −24 conserved nucleotide sequence. This method involves the steps of: (a) transforming a bacterial cell with an expression vector comprising a reporter gene, where the vector comprises a −24 nucleotide sequence element comprising GTTG-GXXXXTT (where X is any nucleotide) positioned between a promoter and a ribosomal binding site (RBS) for the reporter gene; (b) contacting an RpoN protein or peptide to −24 element nucleotide sequence of the reporter gene construct; and (c) determining whether transcription mediated by the reporter gene promoter is impeded, thereby reducing expression of the reporter gene. In some embodiments, the −24 nucleotide sequence element comprising GTTG-GXXXXTT is identified as an RpoN −24 conserved nucleotide sequence element when expression of the reporter gene is reduced.

In one embodiment, the agent of interest is an RpoN protein, an RpoN synthetic peptide or a chemical compound.

In certain embodiments, the reporter gene promoter can be any suitable promoter known in the art including but not limited to lac, trc, T7, tac, $P_{BAD}$, $P_{GRAC}$, rrn promoter.

In another embodiment, the reporter gene encodes lacZ, gus, luciferase, green fluorescent protein (GFP), yellow fluorescent protein (YPF), blue fluorescent protein (BPF), mCherry or a derivative thereof.

The present invention further relates to a synthetic peptide comprising an amino acid sequence that: (a) has 70-75%, 75-80%, 80-85%, 85-90%, 90-95% or 95-100% homology with an RpoN box of Region III of an RpoN protein; and (b) binds specifically to a −24, −12, or −24/−12 site(s) of an RpoN promoter, where the synthetic peptide is effective for repressing transcription and/or gene expression from a binding site of interest, and where the binding site of interest is an RpoN binding site or a cryptic promoter upstream of an RpoN binding site.

In one embodiment, the amino acid sequence comprises the conserved amino acids from an RpoN box of Region III of an RpoN protein through the carboxy terminal amino acid residue of the RpoN protein.

In another embodiment, the Region III comprises a modification to the heptad repeat overlapping the glutamine-rich or acid-rich motifs of an RpoN protein.

In another embodiment, the amino acid sequence comprises at least 20 carboxy terminal amino acids of an RpoN protein.

In another embodiment, the amino acid sequence binds specifically and selectively to a cryptic promoter upstream of an RpoN binding site.

In another embodiment, the amino acid sequence comprises SEQ ID NO:10103 or a functional variant thereof.

The present invention also relates to an isolated nucleic acid molecule encoding the synthetic peptide of the present invention.

In another embodiment, the nucleic acid molecule comprises the nucleotide sequence of SEQ ID NO:10102.

The present invention also relates to a vector comprising the isolated nucleic acid molecule encoding the synthetic peptide of the present invention.

The present invention also relates to a host cell comprising the vector of the present invention.

The present invention further relates to a method of using the synthetic peptide of the present invention for repressing transcription or gene expression from a binding site of interest, where the binding site of interest is an RpoN binding site or a cryptic promoter upstream or downstream of an RpoN binding site. The method involves the steps of: (a) providing the synthetic peptide according to the present invention; and (b) contacting the synthetic peptide to the binding site of interest, thereby repressing transcription or gene expression from the binding site of interest.

Further disclosure regarding aspects of the present invention is provided below.

Method for Repressing Transcription and/or Gene Expression:

A method is provided for repressing transcription and/or gene expression from RpoN binding sites or cryptic promoters upstream of RpoN binding sites. The method can be used to simultaneously shut down the many metabolic pathways that bacteria need to grow and to maintain their virulence. The method can be used as a master switch to turn off the growth of bacteria. The method targets the RpoN binding site, which is conserved among a wide range of bacteria. Thus, inhibition or blocking of the RpoN binding site is deleterious or fatal to the bacteria, and because the binding site regulates so many genes and its sequence is so well conserved, bacteria cannot easily evolve or mutate around the targeted RpoN binding site.

The method can be used, for example to inhibit bacterial cell motility, inhibit bacterial cell growth, inhibit bacterial quorum sensing, kill bacteria, inhibit bacterial attachment, inhibit bacterial virulence, prevent bacterial wilt disease, and/or inhibit bacterial extra polysaccharide production. In another embodiment, any of these uses of the method can be temporally controlled through induction, using standard methods known in the art.

The method comprises providing an agent that specifically and selectively binds to RpoN binding site sequences (or cryptic promoters upstream of RpoN binding sites) to inhibit or repress the expression of genes downstream of that promoter; and contacting the RpoN binding site with the agent.

In one embodiment, the agent can compete with the native RpoN protein for binding at the RpoN binding site. In another embodiment, the agent can bind to a site upstream or downstream of the RpoN binding site and physically block transcription. In another embodiment, the agent blocks the interaction between a transcriptional activator and a RNA polymerase holoenzyme. The agent can bind, for example, at a site between the activator binding site and the binding site for RNA polymerase holoenzyme at a separate promoter.

The agent can be any composition known in the art that will bind specifically to the −24, −12, or −24/−12 site(s) for RpoN binding site (or promoter) interference. Delivery of the agent to the target can include but are not limited to delivery via bacteriophage (Beumer, A., and J. B. Robinson. 2005. A broad-host-range, generalized transducing phage (SN-T) acquires 16S rRNA genes from different genera of bacteria. Appl Environ Microbiol 71:8301-8304; Kwan, T., J. Liu, M. Dubow, P. Gros, and J. Pelletier. 2006. Comparative genomic analysis of 18 *Pseudomonas aeruginosa* bacteriophages. J Bacteriol 188:1184-7; Liu, J., M. Dehbi, G. Moeck, F. Arhin, P. Bauda, D. Bergeron, M. Callejo, V. Ferretti, N. Ha, T. Kwan, J. McCarty, R. Srikumar, D. Williams, J. J. Wu, P. Gros, J. Pelletier, and M. DuBow. 2004. Antimicrobial drug discovery through bacteriophage genomics. Nat Biotechnol 22:185-91), plasmid, chromosomal insertion, RNA, single stranded DNA, single stranded RNA, double stranded DNA, double stranded DNA, DNA-RNA hybrids, which could be linear, circular, or supercoiled. These can enter the cell via delivery methods well known in the art, e.g., transformation, electroporation (Wang, Q., A. P. Mueller, C. R. Leong, K. Matsumoto, S. Taguchi, and C. T. Nomura. 2010. Quick and efficient method for genetic transformation of biopolymer-producing bacteria. J Chem Technol Biotechnol 85:775-778), using a carrier such as DMSO diffusion (Pottz, G., J. Rampey, and B. Furmandean. 1967. The effect of dimethyl sulfoxide (DMSO) on antibiotic sensitivity of a group of medically important microorganisms: preliminary report. Ann NY Acad Sci 141:261-272) via fusion with a carrier such as a siderophore (Budzikiewicz, H.2001. Siderophore-antibiotic conjugates used as Trojan horses against *Pseudomonas aeruginosa*. Curr Top Med Chem 1:73-82), etc.

Three embodiments of the method for inhibiting or repressing the expression of genes downstream from an RpoN promoter are shown in FIGS. 3A-C.

In one embodiment (FIG. 3A), an agent, e.g., a non-native, mutant protein, synthetic peptide, or chemical compound, is used. The agent is capable of binding to the RpoN binding sequence (indicated by the hexagon $\sigma^{54*}$) and antagonizes transcription by the RNA polymerase. Once bound, the agent, e.g., a non-native, mutant protein, a synthetic peptide, or a chemical compound, is unable to interact with the RNA polymerase or activator proteins, thus preventing transcription of the RpoN-specific locus.

In another embodiment (FIG. 3B), multiple copies of a sigma factor, e.g., the sigma factor $\sigma^{54}$, above the level of the native sigma factor can be used to titer out the RpoN promoter sites and to thereby repress the transcription of all loci regulated by RpoN. In FIG. 3B, multiple copies of the native RpoN protein are expressed from the plasmid, showing an inhibitory effect on motility. In cases where genes or operons have more than one promoter, the $\sigma^{54*}$ can inhibit expression by physically blocking RNA polymerase holoenzyme associated with another sigma factor (FIG. 3C). In the embodiment depicted in FIG. 3C, $\sigma^{54*}$, a $\sigma^{70}$ type sigma factor is used, but any sigma factor known in the art may be used that promotes transcription from upstream of the molecular roadblock.

In another embodiment, the agent is an exogenous RpoN protein with a low degree of homology with the native RpoN protein of the bacterial strain that is being treated wherein the exogenous RpoN protein is capable of binding to an RpoN binding site (or promoter) to prevent the expression of one or more genes under the control of RpoN. According to this embodiment, an overabundance of the agent that binds the RpoN promoter can be used. In another embodiment, the agent can be a heterologous RpoN from another bacterial species with low sequence homology to the RpoN protein of the bacteria being treated. Alternatively, engineered RpoN proteins incapable of interacting with the RNA polymerase or enhancer binding proteins (EBPs) can be used. This will result in repression of all RpoN-promoters in the cell.

Exemplary RpoN proteins that can be used according to the methods of the invention are set forth as SEQ ID NOS. 10000-10093.

According to the methods of the invention, any known loci that encode proteins that are regulated by RpoN will be repressed. Additionally, unknown loci that may be under the control of multiple promoters will be repressed. Multiple pathways can be repressed at the same time.

Agents for Repressing RpoN Binding Sites or Cryptic Promoters Upstream of RpoN Binding Sites The method provided herein comprises the step of providing an agent that specifically and selectively binds to an RpoN binding site or promoter sequence (or to a cryptic promoter upstream of an RpoN binding site) to inhibit or repress the expression of genes downstream of that binding site; and contacting the RpoN binding site with the agent. Agents that specifically and selectively bind to an RpoN binding site sequence (or to a cryptic promoter upstream of an RpoN binding site) are also provided.

As disclosed herein, the agent specifically and selectively binds to RpoN promoter sequences to inhibit or repress the expression of genes downstream of that promoter. The agent can be any composition known in the art that will bind specifically to the −24, −12, or −24/−12 site(s) for RpoN promoter interference, e.g., a wild-type or native protein, a non-native protein, a mutant protein, a synthetic peptide, or a chemical compound. Any chemical compound known in the art that binds specifically to the RpoN promoter sequence can be used. In one embodiment, the agent can be a non-protein compound capable of specifically binding to the RpoN promoter site. (e.g., comprising one or more mutations to a native amino acid sequence).

In other embodiments, the agent can be any RpoN protein known in the art, e.g., a wild-type, native, non-native, naturally occurring mutant, engineered (e.g., comprising one or more mutations to a native amino acid sequence) or recombinant RpoN protein.

In another embodiment, the agent can be a wild-type, native, non-native, naturally occurring mutant, engineered or recombinant RpoN protein of interest (or a purified derivative or analog thereof) that displays one or more functional activities of an RpoN protein and that shares at least 30% homology with the RpoN protein of interest. In other embodiments, the agent can be a wild-type, native, non-native, naturally occurring mutant, engineered or recombinant RpoN protein of interest (or a purified derivative or analog thereof) that shares 30-40%, 40-50%, 50-60%, 60-70%, 70-80%, 80-90% or 90-100% homology with the RpoN protein of interest.

In other embodiments, the agent can be a wild-type, native, non-native, naturally occurring mutant, engineered or recombinant RpoN protein of interest (or a purified derivative or analog thereof) that shares 30% or more homology for Region III. In yet other embodiments, the agent can share 30-40%, 40-50%, 50-60%, 60-70%, 70-80%, 80-90% or 90-100% homology with Region III.

Compounds of the aureolic acid family such as mithramycin (MTM), chromomycin, and their derivatives capable of binding to GC-rich DNA sequences that have been used as anticancer drugs are examples of such chemical compounds (Albertini, V., A. Jain, S. Vignati, S, Napoli, A. Rinaldi, I. Kwee, M. Nur-e-Alam, J. Bergant, F. Bertoni, G. M. Carbone, J. Rohr, and C. V. Catapano. 2006. Novel GC-rich DNA-binding compound produced by a genetically engineered mutant of the mithramycin producer *Streptomyces* argillaceus exhibits improved transcriptional; Pucci, D., V. Albertini, R. Bloise, A. Bellusci, A. Cataldi, C. V. Catapano, M. Ghedini, and A. Crispini. 2006. Synthesis and anticancer activity of cyclopalladated complexes containing 4-hydroxy-acridine. J Inorg Biochem 100:1575-8).

In one embodiment, a $\sigma^{54}$ protein is used as the agent. Any $\sigma^{54}$ protein known in the art can be used, e.g., *Klebsiella pneumoniae* $\sigma^{54}$ protein: I123N, L200P, Q351R, S379F, S404F (Pitt, M., M. T. Gallegos, and M. Buck. 2000. Single amino acid substitution mutants of *Klebsiella pneumoniae* sigma(54) defective in transcription. Nucleic Acids Res 28:4419-27).

Other proteins that can be used as agents include, but are not limited to, a modification to the heptad repeat overlapping the glutamine-rich or acid-rich motifs as disclosed in Sasse-Dwight, S., and J. D. Gralla (1990. Role of eukaryotic-type functional domains found in the prokaryotic enhancer receptor factor sigma 54. Cell 62:945-54), truncated RpoN proteins as disclosed in Wong, C., Y. Tintut, and J. D. Gralla (1994. The domain structure of sigma 54 as determined by analysis of a set of deletion mutants. J Mol Biol 236:81-90), including but not limited to Δ2-16, Δ18-31, Δ51-56, Δ79-131, Δ133-157, Δ178-183, Δ4213-244, Δ246-291, Δ293-332 of the RpoN protein from *Escherichia coli*, and truncated RpoN protein from *Aquifex aeolicus* (residues 338-398) as disclosed in Doucleff, M., J. G. Pelton, P. S. Lee, B. T. Nixon, and D. E. Wemmer (2007. Structural basis of DNA recognition by the alternative sigma-factor, sigma54. J Mol Biol 369:1070-8).

In another embodiment, the agent is an RpoN protein with a low degree of homology with the RpoN protein of the bacterial strain that is being treated and/or a peptide that is capable of binding to RpoN promoters to prevent the expression of genes under the control of RpoN. An agent can also be a heterologous RpoN from another bacterial species with low sequence homology to the RpoN protein of the bacteria being treated. Alternatively, engineered RpoN proteins incapable of interacting with the RNA polymerase or enhancer binding proteins (EBPs) can be used as an agent. This will result in repression of all RpoN-promoters in the cell.

In a specific embodiment, the agent is a stabilized cyclic peptide or a stabilized fusion protein, e.g., art-known stabilized cyclic peptides or fusion proteins such as maltose binding protein, glutathione, and green fluorescent protein. An exemplary fusion protein is shown in FIG. 4 (RpoN-thioredoxin fusion).

Overexpression of a protein agent may result in aggregation and poor solubility in heterologous systems. As few as 22.7% of proteins expressed in *E. coli* have been soluble (Butt, T., S. Edavettal, J. Hall, and M. Mattern. 2005. SUMO fusion technology for difficult-to-express proteins. Protein Exp Pur 43:1-9). A variety of structures have been used to enhance soluble protein expression. Some structures that can be added to help with solubility of the protein and stabilization include: small ubiquitin modifying protein (SUMO), glutathione S-transferase (GST), maltose binding protein (MBP), thioredoxin (trx), ubiquitin (Ub), DsbA, NusA, bacterioferritin (BFR), and GrpE (Butt, T., S. Edavettal, J. Hall, and M. Mattern. 2005. SUMO fusion technology for difficult-to-express proteins. Protein Exp Pur 43:1-9; Davis, G., C. Elisee, D. Newham, and R. Harrison. 1999. New fusion protein systems designed to give soluble expression in *Escherichia coli*. Biotechnol Bioeng 65:382-388).

Binding of the agent to an RpoN binding site (or promoter) can be determined or screened for using methods known in the art such as: electrophoretic mobility shift assays (Wigneshweraraj, S. R., S, Nechaev, K. Severinov, and M. Buck. 2002. Beta subunit residues 186-433 and 436-445 are commonly used by Esigma54 and Esigma70 RNA polymerase for open promoter complex formation. J Mol Biol 319:1067-83), transcriptomic analyses using either microarrays or real time sequencing, or reporter assays as described in Example 2.

Any known reporter gene known in the art can be used to screen for binding of an agent to an RpoN binding site, e.g., lacZ; luciferase; gus; green fluorescent protein (GFP), yellow fluorescent protein (YPF), blue fluorescent protein (BPF), mCherry or a derivative thereof. A putative agent can be contacted to an RpoN binding site and modulation (e.g., lowered expression) of the reporter can be screened for.

In another embodiment, the agent specifically and selectively binds to RpoN binding sites downstream of a cryptic promoter thus inhibiting expression from that cryptic promoter. This is demonstrated in Example 4 (see Tables 5-8, in which exemplary sequences of the binding sites are set forth).

The RpoN promoter sequences set forth as SEQ ID NOS 1-9999 are also exemplary RpoN promoter sequences can be used according to the methods of the invention.

A screen is also provided herein to assay the binding of compounds to an RpoN nucleotide sequence. See Example 2 for one embodiment of the screen, an assay for the binding of compounds to the RpoN −24 conserved nucleotide sequence.
Uses of the Method:

The method provided herein can be used in many different applications. The method specifically interferes with the expression of genes involved in bacterial pathogenesis, motility, communication, growth and biofilm production. An advantage of the method is that it can interfere with all of these bacterial characteristics simultaneously, and thus can have broad applications related to medical and preventative treatments for bacterial infection, biocontrol of bacteria or biofouling by bacteria. Since multiple pathways can be repressed at the same time, the method can also be used, for example, to define RpoN regulons for biomedical research and development.

In addition, the method can be used as a tool to study antagonistic relationships of the native RpoN transcription factor under a variety of conditions and in a temporal manner, thereby allowing for fine-tuned analysis of when the RpoN transcription factor is necessary for bacterial responses to the environment. This has the added benefit of identifying regulatory circuits to target with traditional antibiotics.

Because of the ubiquitous and conserved nature of the RpoN promoter, the method targets a broad range of bacteria, including, but not limited to *Pseudomonas aeruginosa, Pseudomonas syringae, Pseudomonas putida, Helicobacter pylori, Campylobacter jejuni, Bacillus subtilis, Bacillus anthracis, Mycobacterium tuberculosis, Escherichia coli, Salmonella typhimurium, Salmonella enterica, Legionella pneumophila, Listeria monocytogenes, Methylobacterium extorquens, Myxococcus xanthus, Borrelia burgdorferi, Vibrio cholerae, Acinetobacter baumanii, Agrobacterium tumefaciens, Bacillus cereus, Bacteroides fragilis, Candidatus* spp., *Chlamydia trachomatis, Chlamydophila pneumoniae, Clostridium acetobutylicum, Clostridium kluyberi, Clostridium perfringens, Geobacter sulfurreducens, Gramella forsetii, Neisseria meningitidis, Ralstonia solanacearum, Shewanella oneidensis, Soilbacter usitatus, Sorangium cellulosum, Sphaerobacter thermophilus, Staphylococcus aureus, Sulfurihydrogenibium* sp. YO3AOP1, *Treponema denticola*, and *Yersinia pestis*. The RpoN promoter sequence and RpoN regulate bacterial expression of genes but not eukaryotic expression of genes. Thus, the technology can be used in humans and animals. The method provides a simple way to inhibit pathogenesis because the expression levels of many of the proteins for virulence in pathogenic bacteria are regulated by RpoN.

The method can be used in medical, agricultural, and bioprocess industries.

Many of the genes encoding proteins associated with biofilm synthesis are regulated by RpoN promoters. Biofilms can be persistent and a source of biofouling of water sources, coatings, microbial influenced corrosion (rusting). The method provided herein can address this by repressing expression of genes associated with the building of these sticky films across a broad spectrum of bacteria.

The method can be used to discover cryptic promoters and genes regulated by RpoN. By using the method to inhibit expression of genes regulated by RpoN promoters, genes can be identified via comparisons using art-known transcriptome analyzing technologies (e.g., real time sequencing, quantitative real time PCR (QRT PCR), microarray analysis).

The method can be used to improve bioprocess applications such as protein and bioproduct production by decreasing metabolic burden of RpoN expressed genes in cells. By eliminating unnecessary burden from RpoN expressed genes, more energy can go towards bioproduct production.

EXAMPLES

The following examples are intended to illustrate particular embodiments of the present invention, but are by no means intended to limit the scope of the present invention.

Example 1

Use of a Synthetic RpoN Promoter Binding Protein in Bacteria to Inhibit the Expression of Virulence Factors This example demonstrates one embodiment of the method for repressing transcription and/or gene expression from an RpoN promoter. In the example, a synthetic RpoN promoter binding protein is used in bacteria to inhibit the expression of virulence factors.

Introduction

Pseudomonads are a broad group of Gram-negative bacteria that are found in many environmental niches. Despites some similarities in gene organization among pseudomonads, some pseudomonads are pathogenic to plants (Penaloza-Vazquez, A., M. K. Fakhr, A. M. Bailey, and C. L. Bender. 2004. AlgR functions in algC expression and virulence in *Pseudomonas syringae* pv. *syringae*. Microbiology 150:2727-37) or animals (Hendrickson, E. L., J. Plotnikova, S. Mahajan-Miklos, L. G. Rahme, and F. M. Ausubel. 2001.

Differential roles of the *Pseudomonas aeruginosa* PA14 rpoN gene in pathogenicity in plants, nematodes, insects, and mice. J Bacteriol 183:7126-34).

*Pseudomonas aeruginosa* is a Gram-negative opportunistic pathogen that causes nosocomial infections and has been implicated as one of the top five organisms that cause pulmonary, bloodstream, urinary tract, surgical site, and soft tissue infections (Veesenmeyer, J. L., A. R. Hauser, T. Lisboa, and J. Rello. 2009. *Pseudomonas aeruginosa* virulence and therapy: evolving translational strategies. Crit. Care Med 37:1777-86). *P. aeruginosa* is also the leading cause of death among patients with cystic fibrosis (Gilligan, P. H. 1991. Microbiology of airway disease in patients with cystic fibrosis. Clin Microbiol Rev 4:35-51). There are many factors associated with virulence that are produced during the course of infection by *P. aeruginosa* including exotoxin A (Azghani, A. O. 1996. *Pseudomonas aeruginosa* and epithelial permeability: role of virulence factors elastase and exotoxin A. Am Respir Cell Mol Biol 15:132-40), hemolysin (Rampioni, G., M. Schuster, E. P. Greenberg, E. Zennaro, and L. Leoni. 2009. Contribution of the RsaL global regulator to *Pseudomonas aeruginosa* virulence and biofilm formation. FEMS Microbiol Lett 301:210-7), elastase (Azghani, A. O. 1996. *Pseudomonas aeruginosa* and epithelial permeability: role of virulence factors elastase and exotoxin A. Am J Respir Cell Mol Biol 15:132-40; Park, P. W., G. B. Pier, M. T. Hinkes, and M. Bernfield. 2001. Exploitation of syndecan-1 shedding by *Pseudomonas aeruginosa* enhances virulence. Nature 411: 98-102), alginate (Cabral, D. A., B. A. Loh, and D. P. Speert. 1987. Mucoid *Pseudomonas aeruginosa* resists nonopsonic phagocytosis by human neutrophils and macrophages. Pediatr Res 22:429-3; Simpson, J. A., S. E. Smith, and R. T. Dean. 1989. Scavenging by alginate of free radicals released by macrophages. Free Radic Biol Med 6:347-53), flagella (Balloy, V., A. Verma, S. Kuravi, M. Si-Tahar, M. Chignard, and R. Ramphal. 2007. The role of flagellin versus motility in acute lung disease caused by *Pseudomonas aeruginosa*. J Infect Dis 196:289-96; Feldman, M., R. Bryan, S. Rajan, L. Scheffler, S. Brunnert, H. Tang, and A. Prince. 1998. Role of flagella in pathogenesis of *Pseudomonas aeruginosa* pulmonary infection. Infect Immun 66:43-5), pili (Chi, E., T. Mehl, D. Nunn, and S. Lory. 1991. Interaction of *Pseudomonas aeruginosa* with A549 pneumocyte cells. Infect Immun 59:822-8; Tang, H., M. Kays, and A. Prince. 1995. Role of *Pseudomonas aeruginosa* pili in acute pulmonary infection. Infect Immun 63:1278-85), extracellular proteases (Nicas, T. I., and B. H. Iglewski. 1985. The contribution of exoproducts to virulence of *Pseudomonas aeruginosa*. Can J Microbiol 31:387-92), rhamnolipids, lipopolysaccharide (Danner, R. L., C. Natanson, R. J. Elfin, J. M. Hosseini, S. Banks, T. J. MacVittie, and J. E. Parrillo. 1990. *Pseudomonas aeruginosa* compared with *Escherichia coli* produces less endotoxemia but more cardiovascular dysfunction and mortality in a canine model of septic shock. Chest 98:1480-7; Pier, G. B., and P. Ames. 1984. Mediation of the killing of rough, mucoid isolates of *Pseudomonas aeruginosa* from patients with cystic fibrosis by the alternative pathway of complement. J Infect Dis 150: 223-8), quorum sensing (Pearson, J. P., M. Feldman, B. H. Iglewski, and A. Prince. 2000. *Pseudomonas aeruginosa* cell-to-cell signaling is required for virulence in a model of acute pulmonary infection. Infect Immun 68:4331-4; Rampioni, G., M. Schuster, E. P. Greenberg, E. Zennaro, and L. Leoni. 2009. Contribution of the RsaL global regulator to *Pseudomonas aeruginosa* virulence and biofilm formation. FEMS Microbiol Lett 301:210-7), pyocyanin (Rampioni, G., M. Schuster, E. P. Greenberg, E. Zennaro, and L. Leoni. 2009. Contribution of the RsaL global regulator to *Pseudomonas aeruginosa* virulence and biofilm formation. FEMS Microbiol Lett 301:210-7), cyanide (Reimmann, C., M. Beyeler, A. Latifi, H. Winteler, M. Foglino, A. Lazdunski, and D. Haas. 1997. The global activator GacA of *Pseudomonas aeruginosa* PAO positively controls the production of the autoinducer N-butyryl-homoserine lactone and the formation of the virulence factors pyocyanin, cyanide, and lipase. Mol Microbiol 24:309-19), pyoverdines (Imperi, F., F. Tiburzi, and P. Visca. 2009. Molecular basis of pyoverdine siderophore recycling in *Pseudomonas aeruginosa*. Proc Natl Acad Sci USA 106:20440-5), biofilms (Jesaitis, A. J., M. J. Franklin, D. Berglund, M. Sasaki, C. I. Lord, J. B. Bleazard, J. E. Duffy, H. Beyenal, and Z. Lewandowski. 2003. Compromised host defense on *Pseudomonas aeruginosa* biofilms: characterization of neutrophil and biofilm interactions. J Immunol 171: 4329-39), and type III secretion system (Lee, V. T., R. S. Smith, B. Tummler, and S. Lory. 2005. Activities of *Pseudomonas aeruginosa* effectors secreted by the Type III secretion system in vitro and during infection. Infect Immun 73:1695-705; Vance, R. E., A. Rietsch, and J. J. Mekalanos. 2005. Role of the type III secreted exoenzymes S, T, and Y in systemic spread of *Pseudomonas aeruginosa* PAO1 in vivo. Infect Immun 73:1706-13). Current therapeutics independently target many of the virulence factors of *P. aeruginosa* (Veesenmeyer, J. L., A. R. Hauser, T. Lisboa, and J. Rello. 2009. *Pseudomonas aeruginosa* virulence and therapy: evolving translational strategies. Crit. Care Med 37:1777-86), but no single current therapy addresses all of these factors.

The expression of the genes encoding these factors or proteins, which make these factors, is controlled by essential subunits of the prokaryotic RNA polymerase called sigma factors. Sigma factors fall into two structurally and mechanistically distinct families: sig70-like sigma factors and sig54. Both families of sigma factors bind to the core RNA polymerase but activate transcription in very different ways. Sig70 class sigma factors bind to the core RNA polymerase holoenzyme (Murakami, K. S., S. Masuda, E. A. Campbell, O. Muzzin, and S. A. Darst. 2002. Structural basis of transcription initiation: An RNA polymerase holoenzyme-DNA complex. Science 296:1285-1290) and then to a promoter specific DNA sequence (usually −10 and −35 nt upstream of the transcription start site) to initiate transcription. Sig54 class sigma factors bind to a conserved nucleotide sequence (mrNrYTGGCACG-N4-TTGCWNNw), the RpoN ($\sigma^{54}$) promoter or binding site (Barrios, H., B. Valderrama, and E. Morett. 1999. Compilation and analysis of sigma(54)-dependent promoter sequences. Nucleic Acids Res 27:4305-13). The sequence is remarkably conserved with some nucleotides in the −24 and −12 sites>90% conserved across a number of bacterial species (Barrios, H., B. Valderrama, and E. Morett. 1999. Compilation and analysis of sigma(54)-dependent promoter sequences. Nucleic Acids Res 27:4305-13).

However, unlike the sig70 family of sigma factors, sig54 is capable of binding to this DNA sequence without first interacting with the RNA polymerase. Once the sig54 interacts with the core RNA polymerase it forms a transcriptionally inactive closed complex consisting of the holoenzyme bound to DNA (Buck, M., M. T. Gallegos, D. J. Studholme, Y. Guo, and J. D. Gralla. 2000. The bacterial enhancer-dependent sigma(54) (sigma(N)) transcription factor. J Bacteriol 182: 4129-36). Unlike sig70 RNA polymerase holoenzymes, the sig54-RNA polymerase complex cannot spontaneously isomerize from a closed to open transcription complex. It must further interact with other transcriptional activating proteins called enhancer binding proteins (EBPs) and use the energy of nucleotide hydrolysis in order to activate transcription from the RpoN promoter (Chen, B., M. Doucleff, D. E. Wemmer, S. De Carlo, H. H. Huang, E. Nogales, T. R. Hoover, E. Kondrashkina, L. Guo, and B. T. Nixon. 2007. ATP ground- and transition states of bacterial enhancer binding AAA+ATPases support complex formation with their target protein, sigma54. Structure 15:429-40).

The RpoN proteins as a class are divided into three regions (Wigneshweraraj, S. R., S, Nechaev, K. Severinov, and M. Buck. 2002. Beta subunit residues 186-433 and 436-445 are commonly used by Esigma54 and Esigma70 RNA polymerase for open promoter complex formation. J Mol Biol 319:1067-83). Region I located near the N-terminus interacts with EBPs necessary to activate transcription. Region II is a linking region. Region III contains subdomains that interact with the RNA polymerase and very highly conserved sequences that are involved in binding the −24/−12 promoter site on the DNA known as the RpoN domain (Doucleff, M., J. G. Pelton, P. S. Lee, B. T. Nixon, and D. E. Wemmer. 2007. Structural basis of DNA recognition by the alternative sigma-factor, sigma54. J Mol Biol 369:1070-8). Because of the lack of homology in Region I among RpoN proteins from various bacterial species, it is likely that this region would be species specific for proper interactions with EBPs. Region II has even less homology cross species. On the other hand, Region III, with its high degree of conserved primary sequence, likely interacts with RpoN promoters regardless of species or primary sequence of Region I and Region II. It has been shown previously that overexpression of RpoN leads to growth inhibition in bacteria, but the cause of this is unknown (Sasse-Dwight, S., and J. D. Gralla. 1990. Role of eukaryotic-type functional domains found in the prokaryotic enhancer receptor factor sigma 54. Cell 62:945-54). The RpoN protein has been shown to activate transcription of genes encoding proteins involved in nitrogen utilization, pilin, flagella, and virulence-related factors in P. aeruginosa (Hendrickson, E. L., J. Plotnikova, S. Mahajan-Miklos, L. G. Rahme, and F. M. Ausubel. 2001. Differential roles of the Pseudomonas aeruginosa PA14 rpoN gene in pathogenicity in plants, nematodes, insects, and mice. J Bacteriol 183:7126-34; Thompson, L. S., J. S. Webb, S. A. Rice, and S. Kjelleberg. 2003. The alternative sigma factor RpoN regulates the quorum sensing gene rhlI in Pseudomonas aeruginosa. FEMS Microbiol Lett 220:187-95; Totten, P. A., J. C. Lara, and S. Lory. 1990. The rpoN gene product of Pseudomonas aeruginosa is required for expression of diverse genes, including the flagellin gene. J Bacteriol 172:389-96). These virulence factors are also under control of RpoN promoters in other bacteria as well (Cases, I., D. W. Ussery, and V. de Lorenzo. 2003. The sigma54 regulon (sigmulon) of Pseudomonas putida. Environ Microbiol 5:1281-93; Hendrickson, E. L., J. Plotnikova, S. Mahajan-Miklos, L. G. Rahme, and F. M. Ausubel. 2001. Differential roles of the Pseudomonas aeruginosa PA14 rpoN gene in pathogenicity in plants, nematodes, insects, and mice. J Bacteriol 183:7126-34; Studholme, D. J., and M. Buck. 2000. The biology of enhancer-dependent transcriptional regulation in bacteria: insights from genome sequences. FEMS Microbiol Lett 186:1-9).

The unique nature with which the RpoN protein regulates gene expression presents a great target for simultaneous inhibition of the expression of virulence factors. This example demonstrates that a synthetic peptide comprising amino acids from Region III of the RpoN protein (see Table 3) can antagonistically impair transcription from multiple RpoN promoters in P. aeruginosa. These amino acids can be defined by the 60 amino acid region of the carboxy terminus of the RpoN protein. Key residues are defined by the RpoN box. Specific residues within the RpoN box essential for interaction include the following sequence of amino acids: ARRTVAKYR(E/D). A thorough definition is given by Doucleff, M., J. G. Pelton, P. S. Lee, B. T. Nixon, and D. E. Wemmer (2007. Structural basis of DNA recognition by the alternative sigma-factor, sigma54. J Mol Biol 369:1070-8). By expressing a peptide capable of binding to the RpoN binding site that is incapable of interacting with the core RNA polymerase or the EBPs, transcription of genes regulated by native RpoN can be disrupted. The antagonistic action of this peptide renders the strain incapable of producing a number of virulence factors and provides information on the multi-layered transcriptional regulation provided by RpoN.

Materials and Methods

Bacterial Strains, Plasmids, and Growth Conditions

Table 1 lists the bacterial strains and plasmids used in the experiments described in this example. *Escherichia coli* strains were routinely grown on Difco™ LB broth (per liter: 10 g tryptone, 5 g yeast extract, 5 g NaCl) nutrient yeast broth (NYB, per liter: 25 g nutrient broth Oxoid no. 2, 5 g yeast extract), or M63 minimal media (per liter: 3 g $KH_2PO_4$, 7 g $K_2HPO_4$, 2 g $(NH_4)_2SO_4$, 0.25 g $MgSO_4.7H_2O$, 5 g glucose, pH 7.0). The following antibiotics were used for *E. coli*: ampicillin, 100 μg ml$^{-1}$, kanamycin 50 μg ml$^{-1}$, tetracycline 10 μg ml$^{-1}$, gentamicin 10 μg ml$^{-1}$, for *P. putida*: kanamycin 50 μg ml$^{-1}$, gentamicin 50 μg ml$^{-1}$, for *P. aeruginosa*: gentamicin 50 μg ml$^{-1}$, for *R. solanacearum*: kanamycin 50 μg ml$^{-1}$, and for *B. cepacia*: gentamicin 50 μg ml$^{-1}$. Isopropyl β-thiogalactopyranoside (IPTG) was purchased from Fisher chemicals. Polymerase Chain Reaction (PCR) was done using the DNA polymerase PrimeStar™ (Takara Biosciences) according to the manufacturer's instructions. All endonucleases and DNA modifying enzymes were purchased from New England Biolabs (Ipswich, Mass.). All nucleic acids were purified using Promega (Madison, Wis.) DNA purification systems.

TABLE 1

Strains and plasmids used in this example.

| Construct | Description | Reference or source |
|---|---|---|
| *Pseudomonas putida* | | |
| KT2440 | Wild-type | ATCC |
| rpoN | rpoN::Km$^r$ | Kohler, T., S. Harayama, J. L. Ramos, and K. N. Timmis. 1989. Involvement of *Pseudomonas putida* RpoN sigma factor in regulation of various metabolic functions. J Bacteriol 171: 4326-33 |
| | KT2440 derivative, pBBR1MCS-2 | This example |
| | rpoN derivative, pBBR1MCS-2 | This example |
| | KT2440 derivative, pBRL340 | This example |
| | rpoN derivative, pBRL340 | This example |

TABLE 1-continued

Strains and plasmids used in this example.

| Construct | Description | Reference or source |
|---|---|---|
| *Pseudomonas aeruginosa* | | |
| PAO1 | Wild-type | ATCC |
| PAO6359 | rpoN::Ω-Km | Heurlier, K., V. Denervaud, G. Pessi, C. Reimmann, and D. Haas. 2003. Negaitive control of quorum sensing by RpoN (sig54) in *Pseudomonas aeruginosa* PAO1. J Bacteriol 185: 2227-2235 |
| PAO1/pBRL344 | PAO1 derivative, pBRL344 | This example |
| PAO1/pBRL348 | PAO1 derivative, pBRL348 | This example |
| PAO1/pBRL349 | PAO1 derivative, pBRL349 | This example |
| PAO6359/pBRL344 | PAO6359 derivative, pBRL344 | This example |
| PAO6359/pBRL348 | PAO6359 derivative, pBRL348 | This example |
| PAO6359/pBRL349 | PAO6359 derivative, pBRL349 | This example |
| *Burkholderia cepacia* ATCC 17759 | Wild-type | ATCC |
| *Ralstonia solanacearum* AW-1 | Wild-type | Denny, T. P., F. W. Makini, and S. W. Brumbley. 1988. Genetic evidence that extracellular polysaccharide is a virulence factor of *Pseudomonas solanacearum* Tn5 mutants deficient in extracellular polysaccharide. Mol Plant-Microbe Interact 1: 215-223 |
| *Escherichia coli* | | |
| JM109 | recA1 endA1 gyrA96 thi-1 hsdR17 ($r_K^-$ $m_K^+$) supE44 relA1 λ-lac [F' proAB lacI$^q$ ZΔM15] | Promega |
| TOP10 | F-mcrA Δ(mrr-hsdRMS-mcrBC) φ80lacZΔM15 ΔlacX74 nupG recA1 araD139 Δ(ara-leu)7697 galE15 galK16 rpsL(Str$^R$) endA1 λ$^-$ | Invitrogen |
| Plasmids | | |
| pBBR1MCS2 | Broad-host range cloning vector; Km$^R$ | Kovach, M. E., P. H. Elzer, D. S. Hill, G. T. Robertson, M. A. Farris, R. M. Roop, 2nd, and K. M. Peterson. 1995. Four new derivatives of the broad-host-range cloning vector pBBR1MCS, carrying different antibiotic-resistance cassettes. Gene 166: 175-6 |
| pBBR1MCS5 | Broad-host range cloning vector; Gm$^R$ | Kovach, M. E., P. H. Elzer, D. S. Hill, G. T. Robertson, M. A. Farris, R. M. Roop, 2nd, and K. M. Peterson. 1995. Four new derivatives of the broad-host-range cloning vector pBBR1MCS, carrying different antibiotic-resistance cassettes. Gene 166: 175-6 |
| pSWU19 | Mx8 att site vector; Km$^R$ | Wang, J., Hu, W., Lux, R., He, X., Li, Y., and W. Shi. 2011. Natural transformation of *Myxococcus xanthus*. J Bacteriol 193(9): 2122-2132. |
| pJ201 | pUC ori, Km$^R$ | DNA 2.0, Menlo Park, CA |
| pBRL306 | pBBR1MCS-2, *Myxococcus xanthus* rpoN | This example |
| pBRL316 | pBBR1MCS-2, *P. putida* KT2440 rpoN | This example |

TABLE 1-continued

Strains and plasmids used in this example.

| Construct | Description | Reference or source |
|---|---|---|
| pBRL323 | pJ201, codon optimized synthetic RpoN region III from *A. aerolicus* (Leu338-Ile398) | This example |
| pBRL340 | pBBR1MCS-2, codon optimized synthetic RpoN region III from *A. aerolicus* (Leu338-Ile398) | This example |
| pBRL344 | pBBR1MCS-5, lacI$^Q$-controlled inducible trc-promoter | This example |
| pBRL348 | pBRL344, codon optimized synthetic RpoN region III from *A. aerolicus* (Leu338-Ile398) | This example |
| pBRL349 | pBRL348, Y48A RpoN (synthetic) | This example |
| pBRL354 | pSWU19, codon optimized synthetic RpoN region III from *A. aerolicus* (Leu338-Ile398) | This example |

Plasmid Construction and DNA Manipulation

TABLE 2

Sequences of oligonucleotides used in this example.

| Amplification product | Primer Name | Oligonucleotide sequence (5'-3') | SEQ ID NO. | Restriction Site |
|---|---|---|---|---|
| *P. putida* rpoN | BL321.f | GCAGCATATGAAACCATCGCTCGTCCTA | 10094 | Nde I |
|  | BL321.r | GCAGGAATTCCTACATCAGTCGCTTGCGTTC | 10095 | EcoR I |
| Y48A RpoN | BL330.f | CGTACGGTTGCCAAGGCTCGTGAGATGCTGGGTATTCCG | 10096 |  |
|  | BL330.r | CGGAATACCCAGCATCTCACGAGCCTTGGCAACCGTACG | 10097 |  |
| Sac I/EcoR I silent mutation of pBRL343 | BL331.f | GGAAACAGACCATGCAATTCCAGCTCGGTACCCGGGGATCC | 10098 |  |
|  | BL331.r | GGATCCCCGGGTACCGAGCTGGAATTGCATGGTCTGTTTCC | 10099 |  |
| lacI$^Q$-rpoN from pBRL348 | BL337.f | GAGCCCTAGGGCATGCATTTACGTTGACACCATC | 10100 | Avr II |
|  | BL337.r | GAGCCCTAGGTCAGAGCTCAATGCGGCGTTCAC | 10101 | Avr II |

The rpoN gene from *M. xanthus* DK1622 was PCR-amplified and subsequently cloned into pCR-Blunt (Invitrogen, Carlsbad, Calif.) according to the manufacturer's instructions. The rpoN gene was subsequently cloned into the Nde I and EcoR I sites of pET28b (Novagen, USA). For expression in bacteria other than *E. coli*, the *M. xanthus* rpoN-pET28b plasmid was digested with Xba I and Sac I to liberate the rpoN gene with the pET28b-derived ribosome binding site. This fragment was ligated into the Xba I/Sac I sites of pBBR1MCS-2 to give pBRL306.

The rpoN gene from *P. putida* was PCR-amplified (primers BL321.f/BL321.r) and subsequently cloned into pCR-Blunt (Invitrogen, Carlsbad, Calif.) according to the manufacturer's instructions to give pBRL310. *P. putida* rpoN was subsequently cloned from pBRL310 into the Nde I/EcoRI sites of pKH22 to give pBRL312. Lastly, pBRL312 was digested with Xba I/Sac I, and the released rpoN fragment was ligated into the Xba I/Sac I sites of pBBR1MCS-2 to yield pBRL315.

A plasmid for the strict and inducible expression of recombinant genes in *P. aeruginosa* was constructed. First, the vector pTrc99a was digested with Sph I and Xba I to release the lacI$^Q$ gene, trc-promoter and the MCS. This fragment was subsequently ligated into the corresponding Sph I/Xba I sites of pBBR1MCS-5 to yield the plasmid pBRL343. For cloning purposes, the Sac I and EcoR I sites of the pTrc99a MCS fragment were removed from pBRL343 via site-directed mutagenesis (primers BL331.f/BL331.r) using the QuikChange™ kit (Stratagene, California) to liberate pBRL344.

A gene encoding the last (C-terminal) 60 amino acid residues of RpoN from *Aquifex aeolicus* was synthesized and optimized to *E. coli-codon* usage by DNA2.0 (Menlo Park, Calif.). Both the amino acid (ORF of 60 amino acids) and DNA sequences (195 base pairs) are given in Table 3 for the engineered rpoN construct (also known as RpoN* or σ54*). For expression purposes, the engineered rpoN construct was cloned from pBRL323 into the Xba I/Sac I sites of pBRL344 to give pBRL348. To generate an attenuated RpoN*, the tyrosine at position 48 was changed into alanine (primers BL330.f/BL330.r) using the Quikchange™ kit (Stratagene, California) with pBRL348 as the template. The resulting plasmid pBRL349 thus contained a Y48A RpoN* protein.

TABLE 3

Nucleotide and amino acid sequence of codon optimized synthetic RpoN region III from *A. aerolicus*.

| | | |
|---|---|---|
| Nucleotide Sequence | 5'-CATATGCTGACCCAAGGCGAACTGATGAAACTGAT CAAAGAAATCGTGGAGAATGAGGACAAGCGTAAAC CGTACAGCGATCAGGAGATCGCGAACATTTTGAAA GAGAAGGGTTTCAAGGTCGCACGCCGTACGGTTGC CAAGTATCGTGAGATGCTGGGTATTCCGTCCAGCC GTGAACGCCGCATTGAGCTC-3' | SEQ ID NO. 10102 |
| Amino Acid Sequence | MLTQGELMKLIKEIVENEDKRKPYSDQEIANILKEKGFK VARRTVAKYREMLGIPSSRERRIEL | SEQ ID NO. 10103 |

RpoN* was shuttled into the *M. xanthus* Mx8 att-site integration vector, pSWU19. First, the lacI$^Q$-rpoN cluster from pBRL348 was PCR-amplified (see Table 2 for primers, BL337.f/BL337.r) and cloned into pCR-Blunt (Invitrogen, Carlsbad, Calif.) according to the manufacturer's instructions to give pBRL353. The lacI$^Q$-rpoN fragment was then excised from pBRL353 by Avr II digestion, and then subsequently ligated into the Xba I site of pSWU19 to yield pBRL354.

Plasmids were introduced into *P. putida*, *B. cepacia* and *P. aeruginosa* using previously established electroporation methods (Wang, Q., A. P. Mueller, C. R. Leong, K. Matsumoto, S. Taguchi, and C. T. Nomura. 2010. Quick and efficient method for genetic transformation of biopolymer-producing bacteria. J Chem Technol Biotechnol 85:775-778). A BTX Harvard apparatus ECM 399 was used for all electroporations.

Swarming and Twitching Motility Assays

Swarming and twitching motility were done as described previously (O'Toole, G. A., and R. Kolter. 1998. Flagellar and twitching motility are necessary for *Pseudomonas aeruginosa* biofilm development. Mol Microbiol 30:295-304). Plates used in motility assays were supplemented with 2 mM IPTG.

For *P. putida*, individual colonies were stabbed onto M63 minimal media plates supplemented with 0.5% glucose, 0.5% casamino acids (CAA) and 0.3% Difco™ agar. The resulting plates were grown at 30° C. for 24 h at which time motility was assessed.

For *B. cepacia*, individual colonies were stabbed onto LB plates with 0.2% glucose and 0.3% agar. Plates were incubated at either 30 or 37° C. for 24 h.

For *P. aeruginosa*, individual colonies were stabbed onto either i) M63 minimal media plates supplemented with 0.5% glucose, 0.5% CAA and 0.3% agar or ii) LB plates with 0.5% CAA and 0.3% agar. Plates were incubated at 25, 30 or 37° C. for 24 h.

Pyocyanin Production

Production of pyocyanin from *P. aeruginosa* in LB was determined as described (Dong, Y.-H., X.-F. Zhang, H.-M. L. Soo, E. P. Greenberg, and L.-H. Zhang. 2005. The two-component response regulator PprB modulates quorum-sensing signal production and global gene expression in *Pseudomonas aeruginosa*. Mol Microbiol 56:1287-1301). Briefly, 2 mL of LB was inoculated with 0.5% of seed culture and then grown to an OD$_{600}$ of 0.3 at 37° C., 250 rpm. IPTG was added to a final concentration of 2 mM, and the induced cultures were grown for 16 h at 37° C., 250 rpm. After incubation, cells were cleared by passage through a 0.2 micron filter, and the pyocyanin was extracted from 1.5 ml of the cell-free broth by the addition of 1 ml of chloroform. The resulting chloroform phase was then extracted with an equal volume of 0.2 M HCl, and the aqueous phase was assayed at 520 nm for pyocyanin.

Protease Assays

Protease activity was assessed by patching individual *P. aeruginosa* colonies onto either LB or LB plus 2% skim milk plates, which were supplemented with 2 mM IPTG. Patched plates were incubated at 25, 30 or 37° C. for 24 h. Breakdown of protein was determined by colony and/or halo formation.

Elastase activities of cell-free broth from *P. aeruginosa*-cultures grown in PTSB (5% peptone, 0.25% tryptic soy broth) were measured by breakdown of elastin-congo red complex as described (Dong, Y.-H., X.-F. Zhang, H.-M. L. Soo, E. P. Greenberg, and L.-H. Zhang. 2005. The two-component response regulator PprB modulates quorum-sensing signal production and global gene expression in *Pseudomonas aeruginosa*. Mol Microbiol 56:1287-1301; Ohman, D. E., S. J. Cryz, and B. H. Iglewski. 1980. Isolation and characterization of *Pseudomonas aeruginosa* PAO mutant that produces altered elastase. J Bacteriol 142:836-842). Briefly, 1.8 mL of PTSB was inoculated with 0.5% of seed culture and subsequently grown at 37° C., 250 rpm until an OD$_{600}$ of 0.1 was reached. At that time, gene expression was induced with a final concentration of 2 mM IPTG, and the cultures were grown for a total of 16 h post induction. Following incubation, the broth was passed through a 0.2-micron filter to remove the cells, and 1 ml of the resulting cell-free filtrate was added to 2 ml of elastase reaction buffer (0.1 M Tris, pH 7.2, 1 mM $CaCl_2$, 10 mg $ml^{-1}$ elastin-congo red). Reactions were carried out at 37° C. for 7 h. Subsequently, insoluble material in the reaction mixture was removed by centrifugation, and the resulting supernatant was assayed at an absorbance of 459 nm.

Hemolysin Assays

Individual *P. aeruginosa* colonies were patched onto LB plates supplemented with 0.5% CAA and 5% sheep blood. Hemolytic activity was determined after 24 h of growth at 37° C.

Growth of *E. coli* MG1655 on W-Salt Minimal Plates

*E. coli* MG1655 harboring either pSWU19 or pBRL354 were patched onto W-salt plates (per liter: 10.5 g $K_2HPO_4$, 4.5 g $KH_2PO_4$, 0.261 ml of 1 M $MgSO_4.7H_2O$, 5 g glucose) supplemented with 0.4% $(NH_4)SO_4$ or 0.2% L-glutamine as the sole nitrogen source, and 2 mM IPTG. Patched plates were grown at 37° C. for 24-48 h.

Results

Motility is Inhibited when RpoN is Overexpressed

RpoN is known to be essential for motility in several pseudomonads such as *P. putida* and *P. aeruginosa*. Indeed, expression of several vital motility genes is mediated through the RpoN-RNAP holoenzyme in an EBP-dependent manner. To show that a non-native RpoN could effectively compete with an organism's native $\sigma^{54}$ due to the universal-nature of the -12/-24 promoter, the full-length RpoN protein from the distantly related *M. xanthus* was overexpressed in *P. putida* KT2440. As expected, motility on M63 soft agar plates was completely abolished for *P. putida* when expressing *M. xanthus* RpoN (FIG. 4); *P. putida* harboring the *M. xanthus* RpoN were also observed to 'sink' in LB-liquid culture, thus suggesting defects in swimming motility. Interestingly, overexpression of the *P. putida*'s native RpoN significantly reduced motility (FIG. 4). These results suggested that overexpression of full length RpoN can antagonize motility in *P. putida*.

It has been shown that the last 60 amino acids (region III) of RpoN are sufficient for recognition and binding to the -24 element of the $\sigma^{54}$ promoter. Because of the conservation of both the -24-promoter element and region III of RpoN, we hypothesized that a peptide composed of only the region III amino acid residues would be sufficient for antagonizing genome-wide transcription at $\sigma^{54}$ promoters. This is determined by Doucleff et al. 2007. To this end, a peptide was synthesized to resemble region III (Leu338-Ile398) of RpoN from the thermophilic bacterium *A. aeolicus* and was codon-optimized for expression in *E. coli*.

Figure 5:
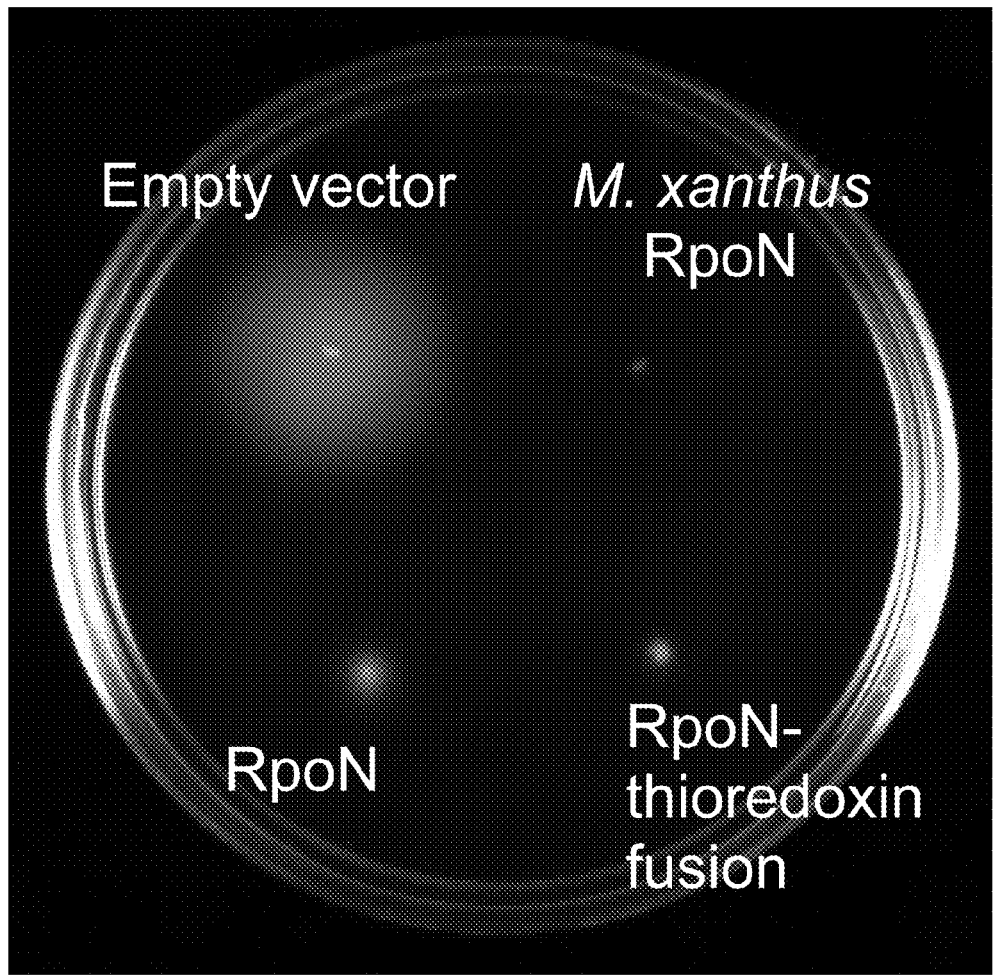
FIG. 5: *P. putida* KT2440 motility on M63 soft agar expressing i) pBRL344 (empty vector), ii) *M. xanthus* RpoN, iii) truncated RpoN, or iv) thioredoxin-RpoN fusion protein.

Introduction of the synthetic, truncated RpoN into *P. putida* KT2440 generated strains incapable of moving on M63 soft agar plates (FIG. 5). When the RpoN construct was attenuated by replacing the tyrosine residue in the RpoN box motif with alanine (Y48A), motility was only impaired and not absent. This suggested that the antagonizing effect of RpoN can be localized to region III and its interaction with the -24 element of $\sigma^{54}$ promoters in the bacterial genome.

Figure 6:
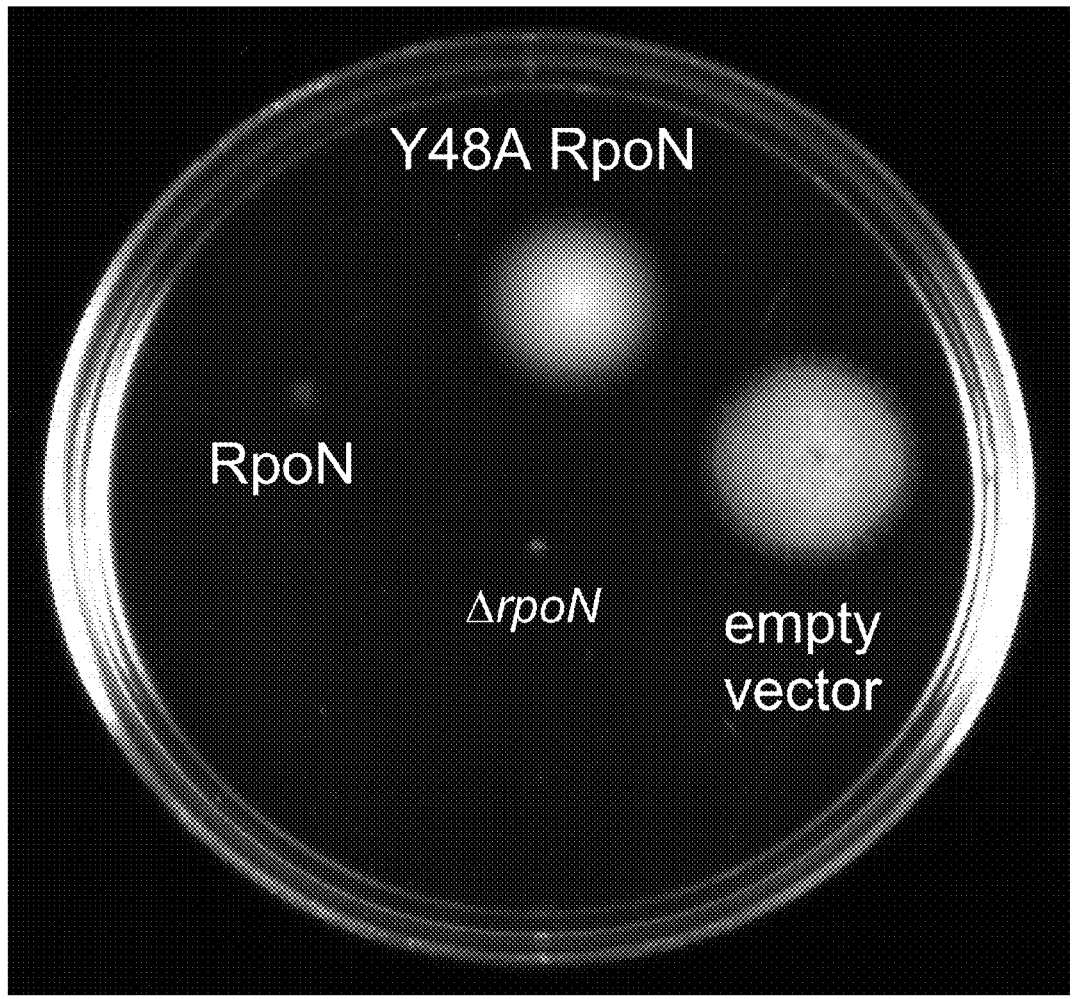
FIG. 6: *P. aeruginosa* PAO1 motility on M63 soft agar expressing i) pBRL344 (empty vector), ii) truncated RpoN, or iii) Y48A RpoN. The ΔrpoN PAO1 strain was used as a control.
Figure 7:
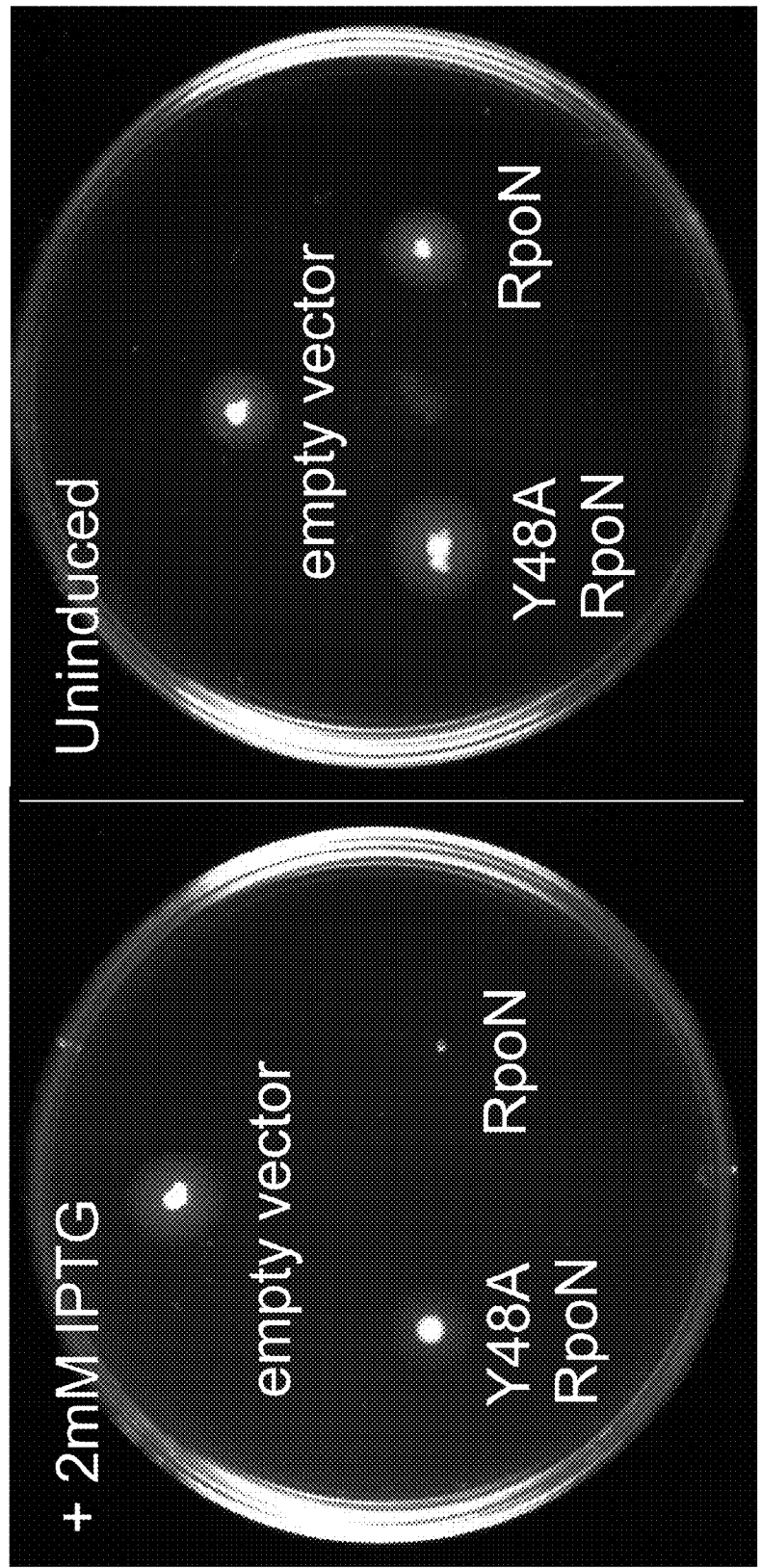
FIG. 7: *P. aeruginosa* PAO1 twitching motility when expressing i) pBRL344 (empty vector), ii) truncated RpoN, or iii) Y48A RpoN.
Figure 8:
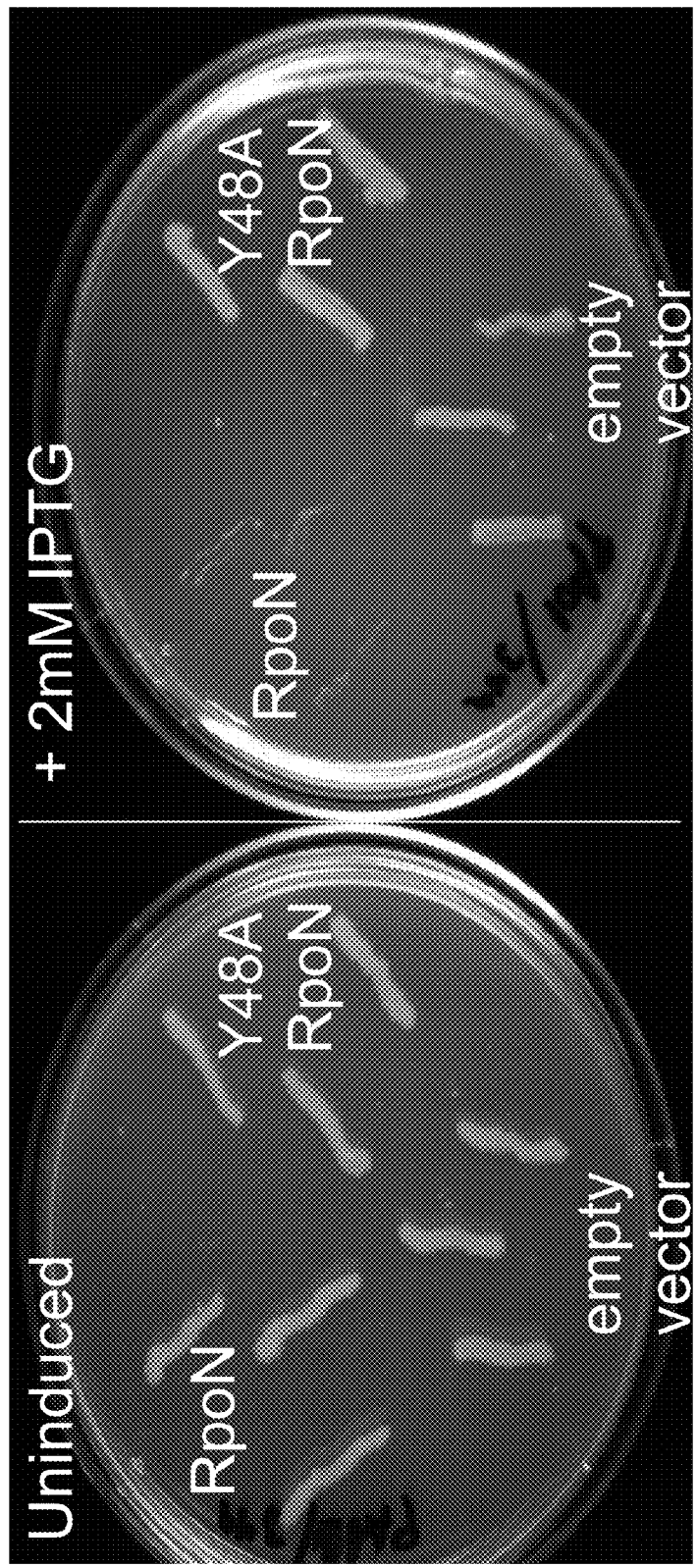
FIG. 8: *P. aeruginosa* PAO1 growth on Lennox broth solid media when expressing i) pBRL344 (empty vector), ii) truncated RpoN, or iii) Y48A RpoN.
Figure 10:
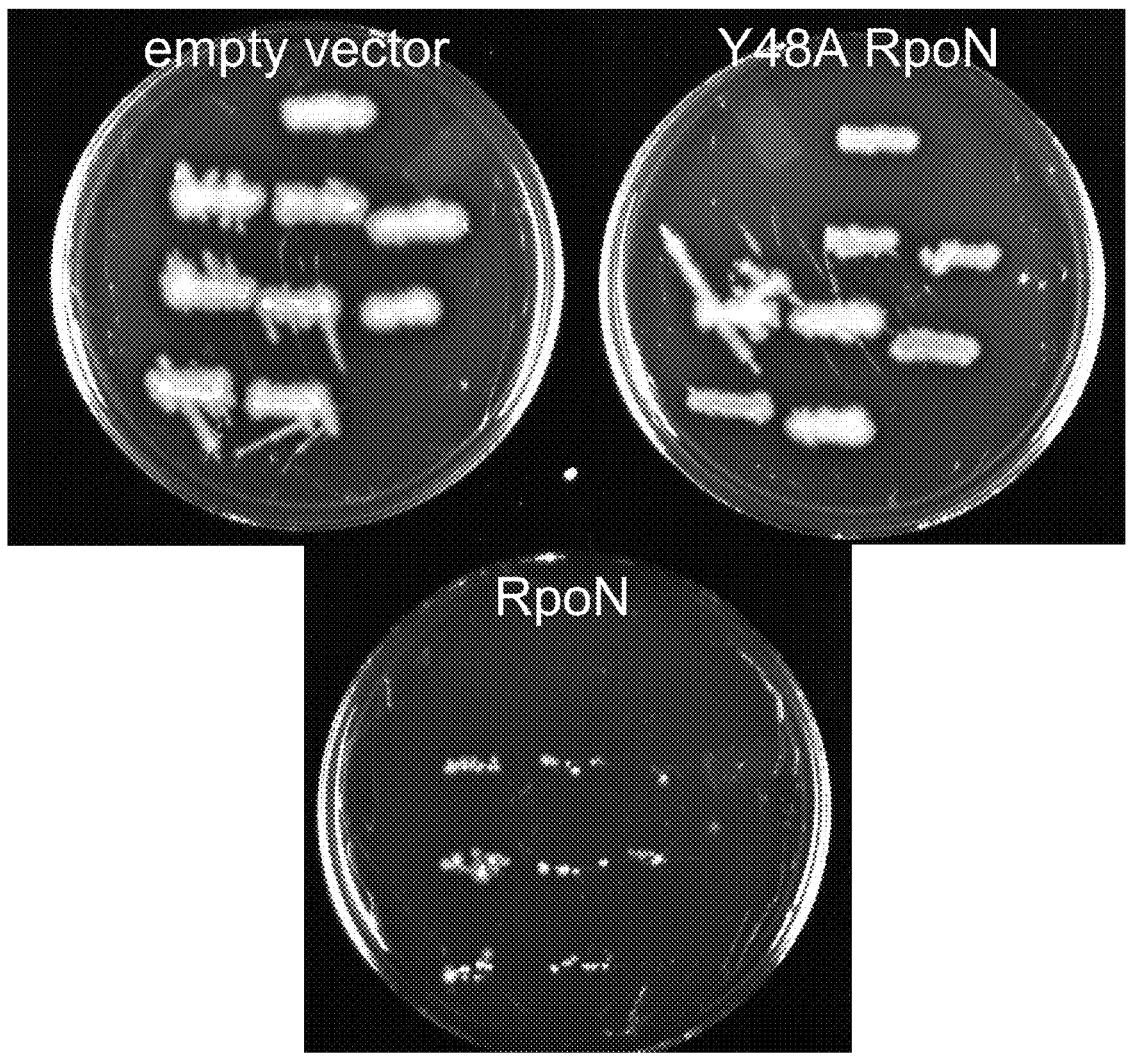
FIG. 10: *P. aeruginosa* PAO1 growth LB+5% sheep blood expressing i) pBRL344 (empty vector), ii) truncated RpoN, or iii) Y48A RpoN.
Figure 11:
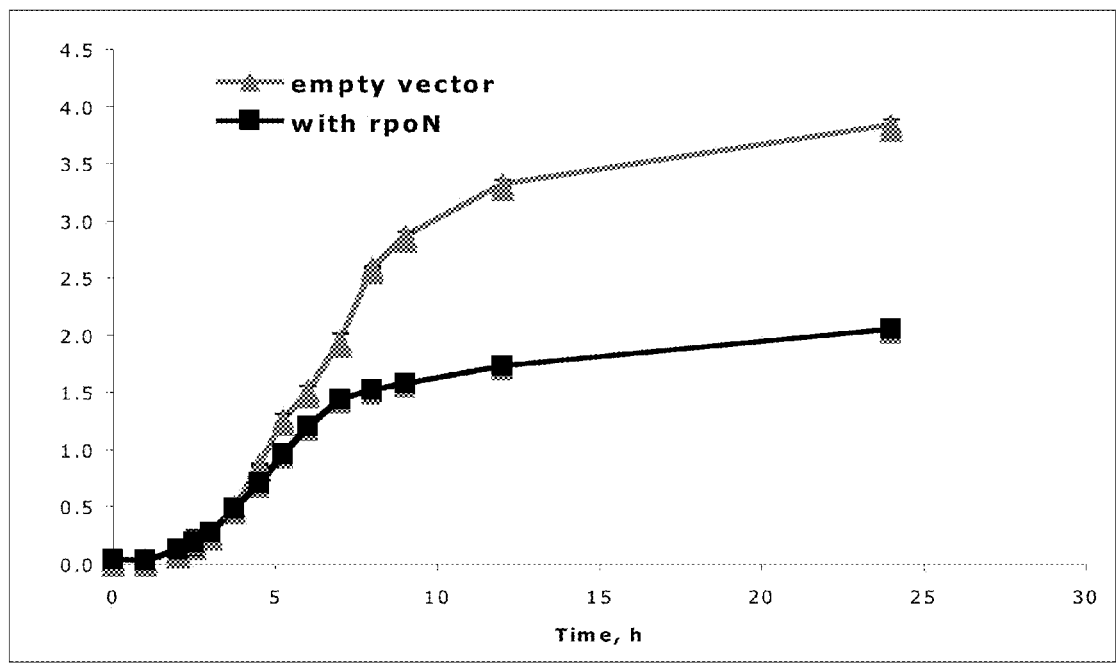
FIG. 11: *P. aeruginosa* PAO1 growth in LB expressing either i) pBRL344 (empty vector) or ii) synthetic, truncated RpoN.

The synthetic, truncated RpoN was then expressed in a medically relevant bacterium, *P. aeruginosa* PAO1. As for the case of *P. putida*, overexpression of RpoN in *P. aeruginosa* PAO1 inhibited motility on semisolid plates consisting of either minimal or rich media (FIG. 6 and FIG. 7). Motility is known to require RpoN in *P. aeruginosa*, and the heterologously expressed RpoN peptide antagonized motility, and as shown below, other virulent factors associated with this opportunistic pathogen.

Virulence Factors are Negatively Affected by RpoN Overexpression

Figure 12:
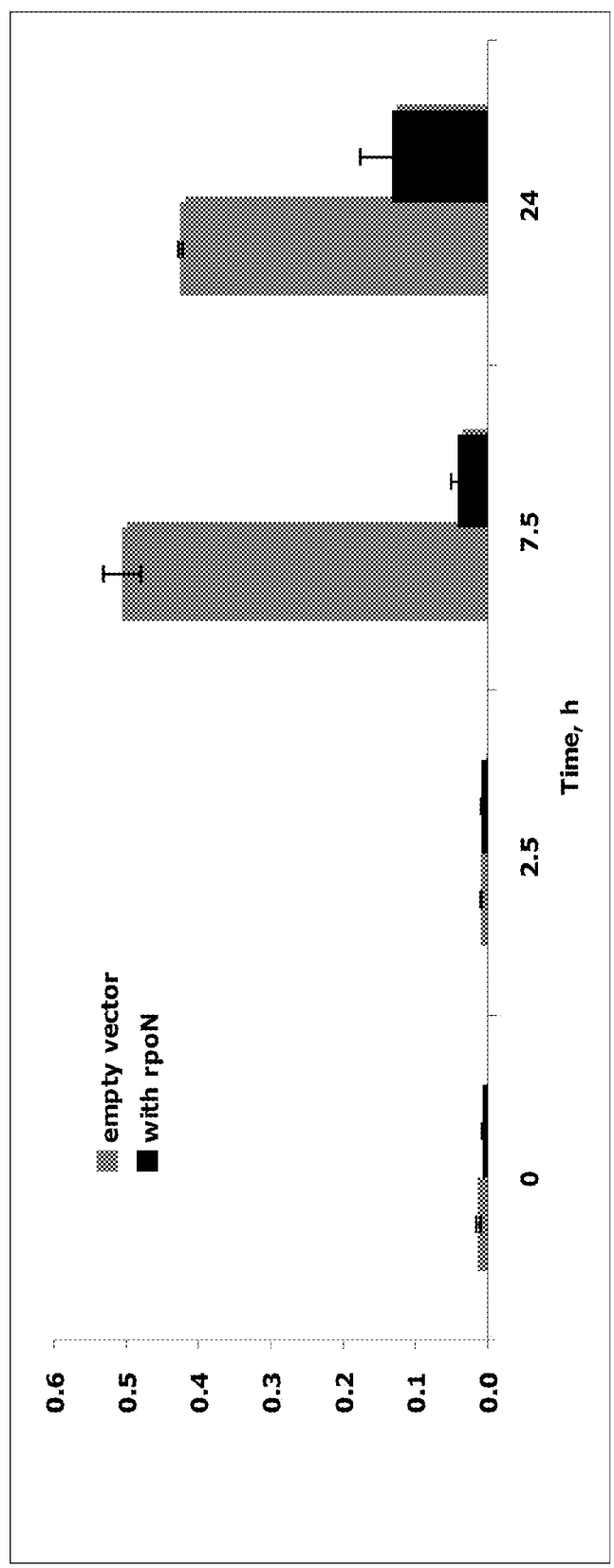
FIG. 12: Elastase production *P. aeruginosa* PAO1 in PTSB media expressing either i) pBRL344 (empty vector) or ii) synthetic, truncated RpoN. Elastase activity was measured at 0, 2.5, 7.5 or 24 h post inoculation. Note that 7.5 h time point represents 4 h post induction.

A notable characteristic of *P. aeruginosa* harboring the synthetic, truncated RpoN was its inability to breakdown protein. Extracellular proteases such as elastase and protease IV are critical virulent factors of *P. aeruginosa*. *P. aeruginosa* PAO1 strains possessing the synthetic, truncated RpoN failed to grow on a variety of rich media: LB, LB+2% milk, LB+5% sheep's blood, PTSB (5% peptone, 0.25% yeast extract) or King's B medium (FIGS. 8-11). Media had to be supplemented with CAA to promote a slow growth of PAO1/pBRL348 strains. Importantly, elastase, which serves as the major protease of *P. aeruginosa*, was found to be <10-fold active (FIG. 12) in spent PTSB-medium of PAO1/pBRL348 than that of wildtype (PAO1/pBRL344). Microarray analysis indicated that expression of the elastase genes, lasA and lasB, were downregulated by 11- and 36-fold, respectively, in PAO1/pBRL348 cells.

Figure 13:
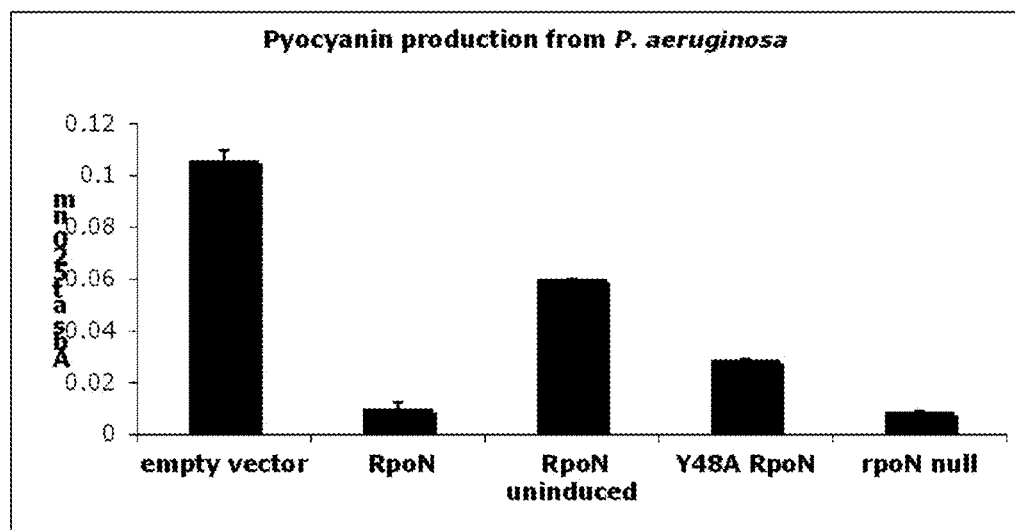
FIG. 13: Pyocyanin production *P. aeruginosa* PAO1 in LB media expressing either i) pBRL344 (empty vector), ii) synthetic, truncated or iii) Y48A RpoN. The ΔrpoN PAO1 strain was used as a control.

Another extracellular virulent factor associated with *P. aeruginosa* is the redox active phenazine compound pyocyanin. Pyocyanin production was significantly lower (<10 fold) for PAO1 when expressing the synthetic, truncated RpoN (FIG. 13). Microarray analysis showed that genes involved in the biosynthesis of phenazines were downregulated by 20-80 fold in PAO1/pBRL348 cultures.

RpoN Antagonism in Other Bacteria

Figure 14:
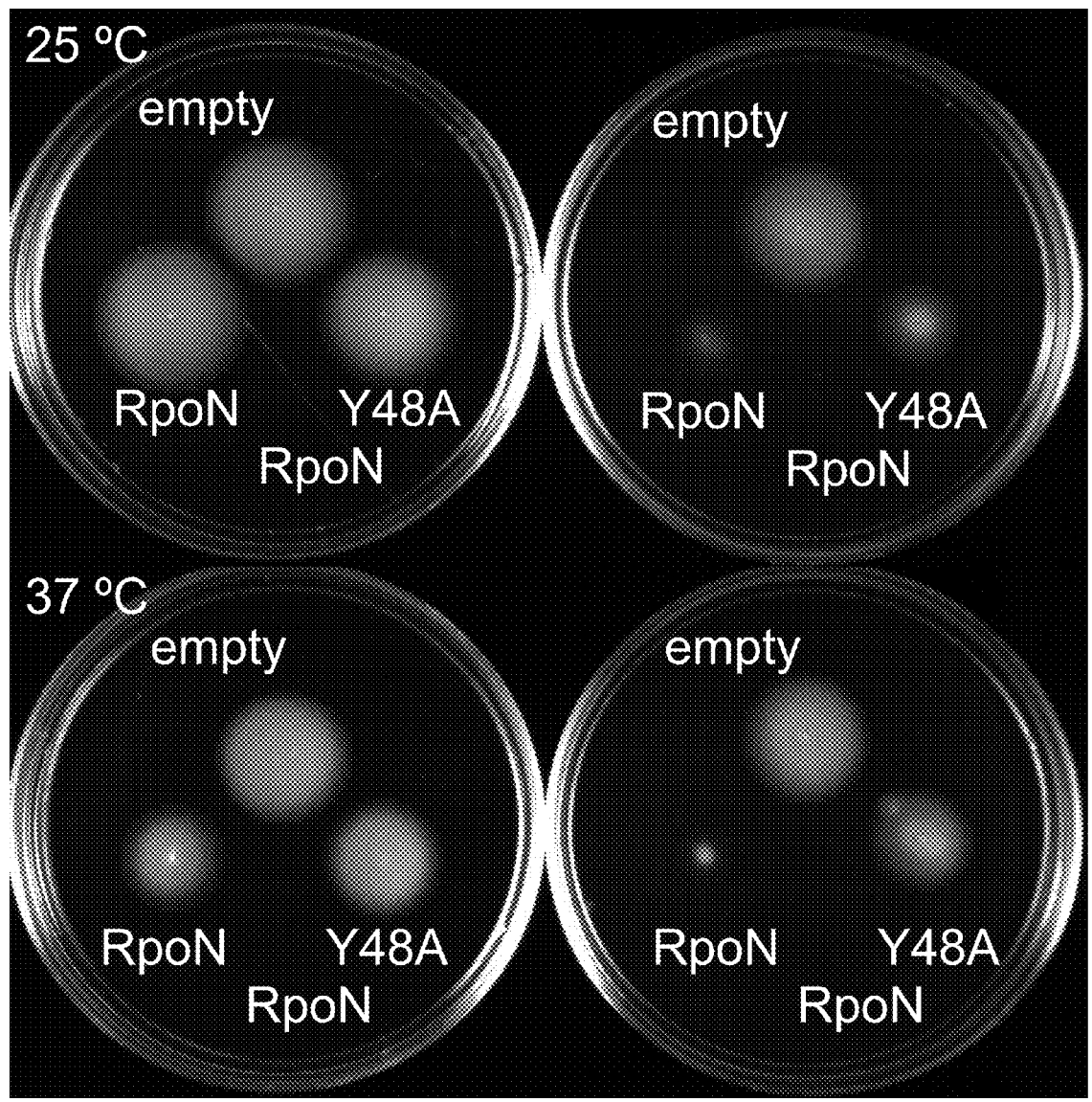
FIG. 14: Motility of *B. cepacia* on LB soft agar expressing either i) pBRL344 (empty vector), ii) synthetic, truncated or iii) Y48A RpoN.
Figure 15:
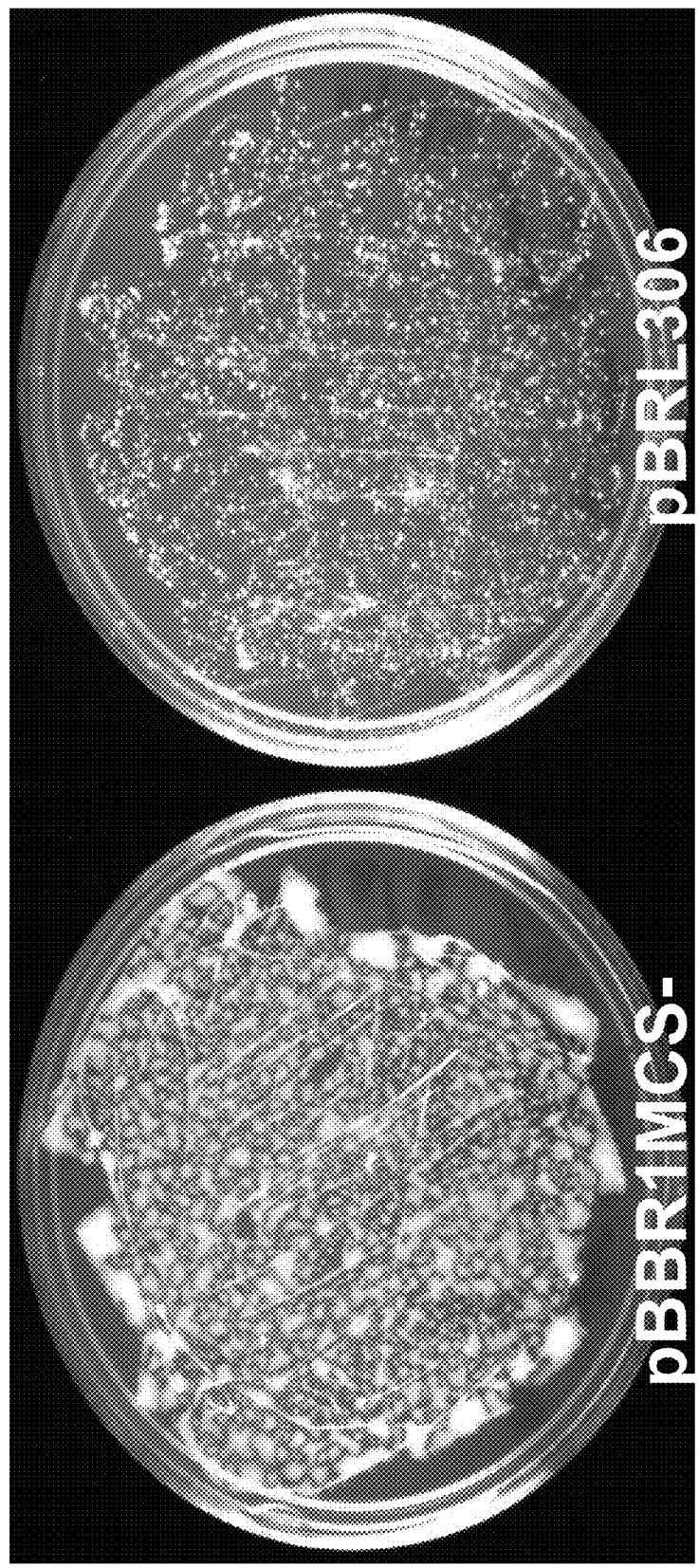
FIG. 15: Extracellular polysaccharide production from *R. solanacearum* expressing either pBBR1MCS-2 or *M. xanthus* rpoN (pBRL306).
Figure 16:
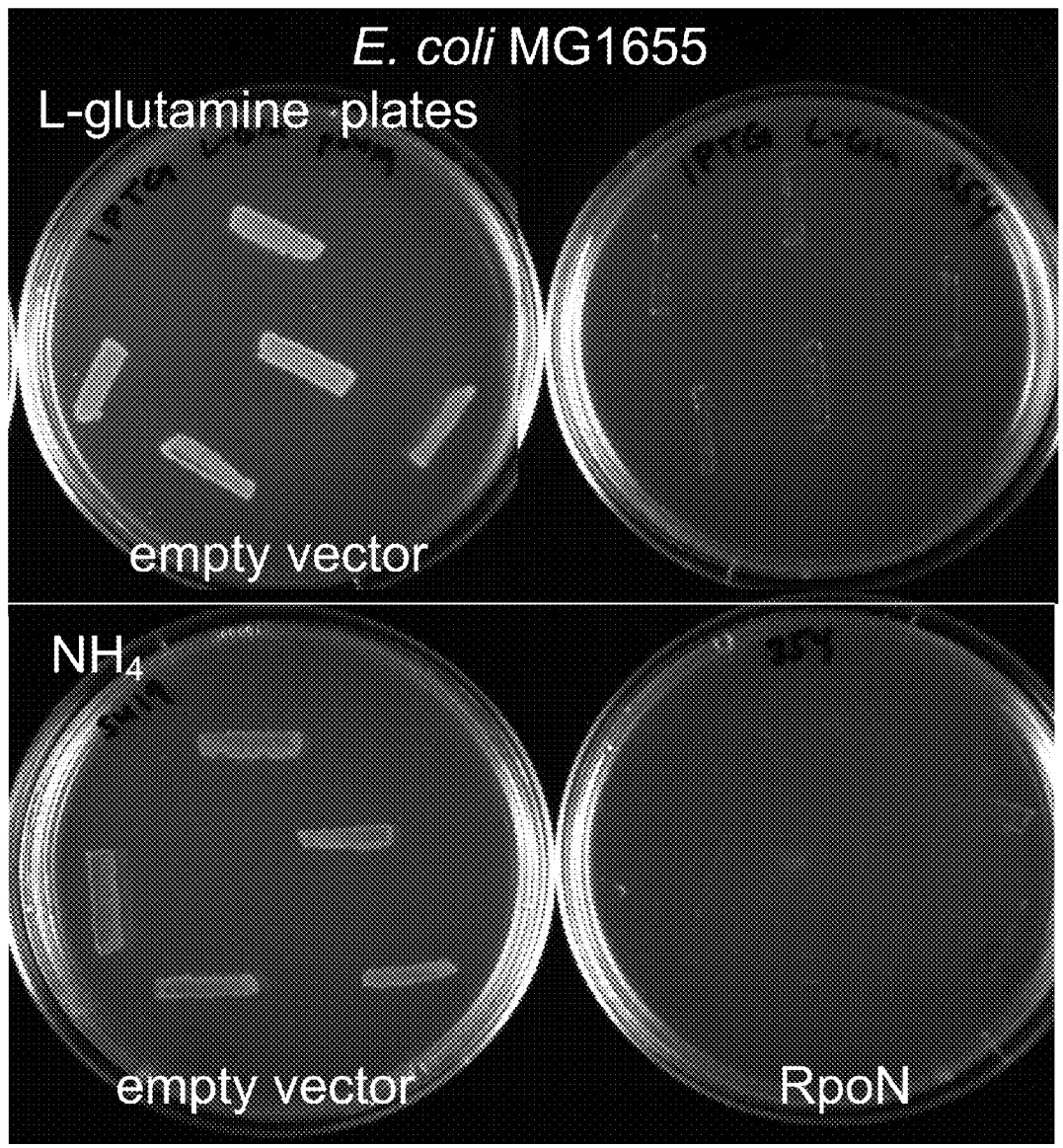
FIG. 16: Growth of *E. coli* MG1655 on W-salt agar plates with either L-Gln or ammonia as the sole nitrogen source.

To examine a broader impact of RpoN antagonism, RpoN was overexpressed in a variety of bacterial species. First, the synthetic, truncated RpoN was introduced into the human pathogen *B. cepacia*, and motility was assessed on LB-semisolid media. As shown in FIG. 14, *B. cepacia*/pBRL348 displayed impaired motility compared to the wildtype (*B. cepacia*/pBRL344). RpoN is required for motility in *Burkholderia*, and our results support the antagonistic nature of the synthetic, truncated RpoN with *B. cepacia* $\sigma^{54}$ promoters. In contrast to motility, we found a significant reduction in the extracellular polysaccharide (EPS) produced by the plant-pathogen *R. solanacearum* when it overexpressed the rpoN gene from *M. xanthus* (FIG. 15). And lastly, overexpression of the synthetic, truncated RpoN in *E. coli* MG1655 altered its metabolism of nitrogenous sources as shown in FIG. 16. As predicted, growth could be sustained on minimal media when L-glutamine but not ammonia was the sole nitrogen source.

Example 2

Method for Screening for RpoN -24 Binding Motifs

This example describes a method for examining the repression and/or interference of RpoN proteins and RpoN binding motif preferences and/or substrate specificity.

To screen -24 elements (nucleotide sequences) for RpoN binding, a plasmid-based reporter assay was developed. Nucleotide sequences, which comprised GTTGGXXXXTT (where X is any nucleotide depending on the -24 element, see Table 4), were introduced, using standard methods known in the art, between the lac promoter and RBS for the mCherry gene in the pmCherry plasmid (Clontech) via site-directed mutagenesis (Quikchange™, Stratagene). Binding of RpoN to the introduced, -24 element impedes $P_{lac}$-mediated transcription of the mCherry gene, thus reducing gene expression of the fluorescent mCherry protein.

TABLE 4

| Construct | -24 element or full promoter (italics) | -12/24 Forward (f) and reverse (r) primers used for site-directed mutagenesis with pmCherry (Clontech) |
|---|---|---|
| pmcherry-346 | GT-*TGGCACG*-TT [SEQ ID NO: 10104] | f-gagcggataacaattgttggcacgttcacacaggaaacagc [SEQ ID NO: 10105] r-gctgtttcctgtgtgaacgtgccaacaattgttatccgctc [SEQ ID NO: 10106] |
| pmcherry-347 | GT-*TGGTACA*-TT [SEQ ID NO: 10107] | f-gagcggataacaattgttggtacattcacacaggaaacagc [SEQ ID NO: 10108] r-gctgtttcctgtgtgaatgtaccaacaattgttatccgctc [SEQ ID NO: 10109] |
| pmcherry-348 | GT-*TGGCCCA*-TT [SEQ ID NO: 10110] | f-gagcggataacaattgttggcccattcacacaggaaacagc [SEQ ID NO: 10111] r-gctgtttcctgtgtgaatgggccaacaattgttatccgctc [SEQ ID NO: 10112] |
| pmcherry-350 | GT-*TCCCACG*-TT [SEQ ID NO: 10113] | f-gagcggataacaattgttcccacgttcacacaggaaacagc [SEQ ID NO: 10114] r-gctgtttcctgtgtgaacgtgggaacaattgttatccgctc [SEQ ID NO: 10115] |
| pmcherry-351 | GT-*TGGCACGGCCGTTGCT*-TA [SEQ ID NO: 10116] | f-gagcggataacaattgttggcacggccgttgctattcacacaggaaacagc [SEQ ID NO: 10117] r-gctgtttcctgtgtgaatagcaacggccgtgccaacaattgttatccgctc [SEQ ID NO: 10118] |
| pmcherry-352 | GT-*TGGCACAGATTTCGCT*-TT [SEQ ID NO: 10119] | f-gagcggataacaattgttggcacagatttcgctttcacacaggaaacagc [SEQ ID NO: 10120] r-gctgtttcctgtgtgaaagcgaaatctgtgccaacaattgttatccgctc [SEQ ID NO: 10121] |

The −24-element bearing pmCherry constructs were transformed into either JM109/pBRL340 or Top10/pBRL348 *E. coli* cells, which harbored the truncated, synthetic RpoN. Strains were grown in 20 mL of LB (in a 500-mL baffled shake flask) with the appropriate antibiotics at 37° C., 250 rpm, until an $OD_{600}$ of 0.2 was reached. At this time, lacI$^Q$-repression was relieved by the addition of 0.5 mM IPTG, and the induced *E. coli* cultures were grown for an additional 8 h at 37° C., 250 rpm. For extraction of mCherry, a total of 1.5 mL of each culture was harvested, and the resulting cell pellet was suspended in 0.6 mL of B-PER Bacterial Protein Extraction Reagent (Thermo Scientific, cat no. 78243). Suspensions (extractions) were incubated at 25° C. for 20 min, and then the unlysed cells and cellular debris were removed by centrifugation. Cleared supernatants were assayed at 586 nm for mCherry activity.

Figure 17:
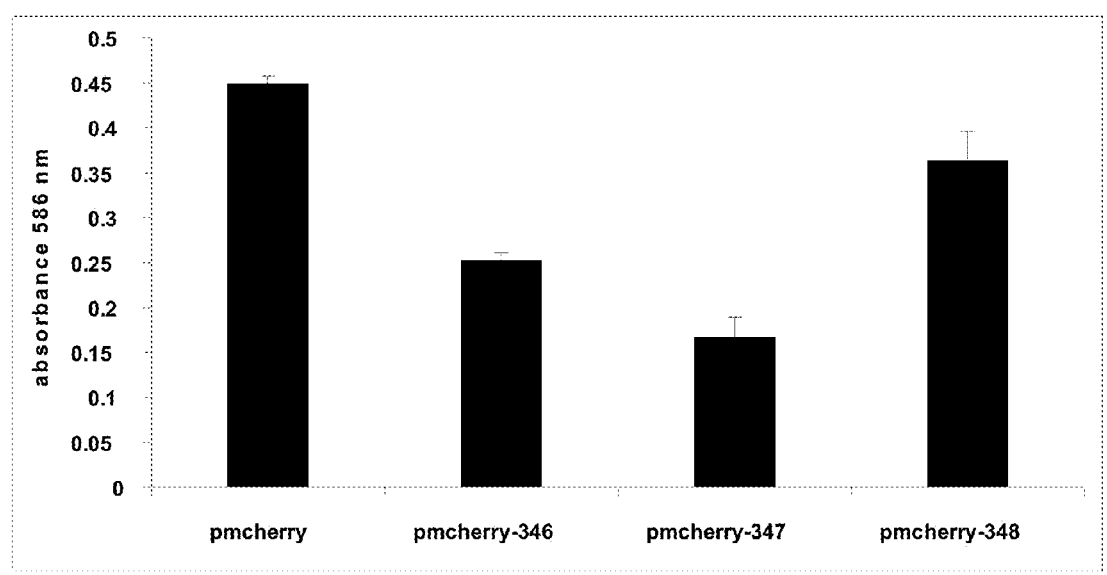
FIG. 17: Expression of pmcherry from the Plac-RpoN promoter is reduced in the presence of the synthetic RpoN.
Figure 18:
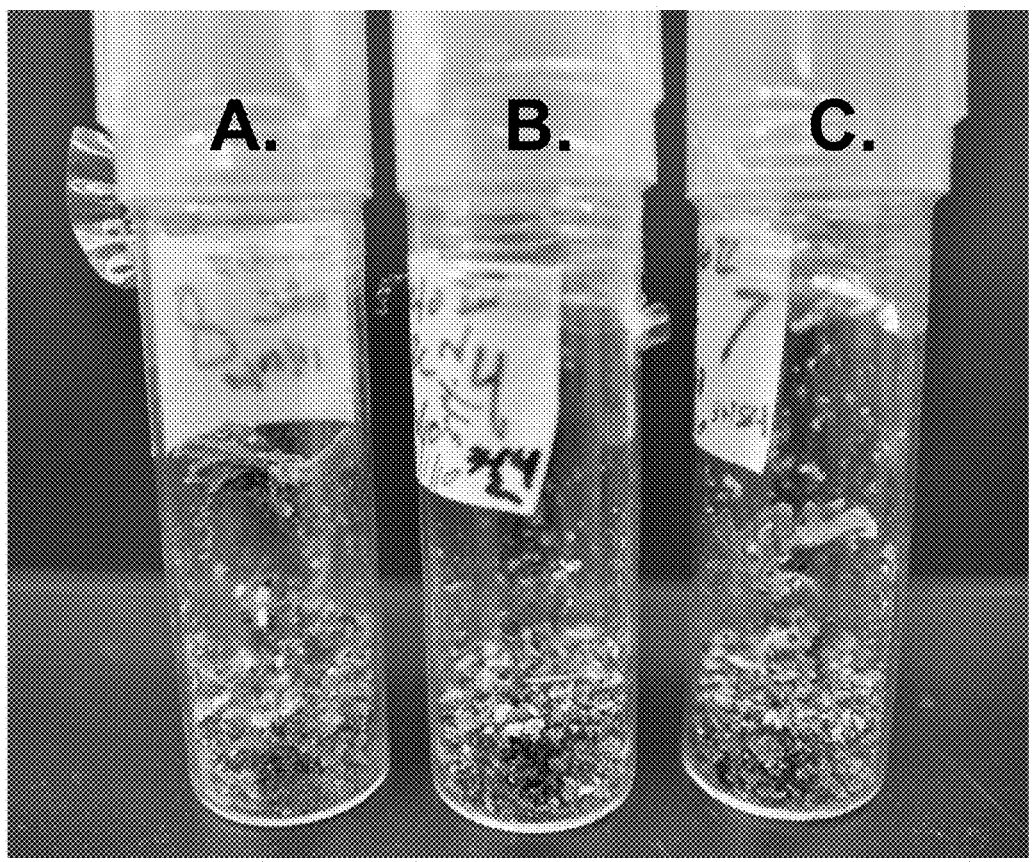
FIG. 18: Effect of synthetic RpoN on *R. solanacearum* plant pathogenicity. A. Untreated tomato seedling control. B. Tomato seedling treated with *R. solanac

Results are shown in FIG. 17. FIG. 17 shows expression of pmCherry from the $P_{lac}$-RpoN promoter is reduced in the presence of the synthetic RpoN.

These results demonstrate that there is a binding preference for the −24 binding motif by the RpoN box binding domain and that this domain can directly interfere with expression of genes downstream.

Example 3

Method for Preventing Virulence by *Ralstonia solanacearum* Against Tomato Plants This example demonstrates that the RpoN synthetic peptide can be used to repress plant pathogenicity in *Ralstonia solanacearum* (formerly *Pseudomonas solanacearum*). *R. solanacearum* harboring either pBRL344 or pBRL348 was grown in BG medium supplemented with 15 μg $mL^{-1}$ gentamicin at 30° C./250 rpm until an $OD_{600}$ of 0.3 was reached. At this time, IPTG was added to a final concentration of 2 mM, and the induced cultures were grown for 16 h at 30° C. at 250 rpm. Pathogenicity of the treated (induced) *R. solanacearum* cultures was tested on tomato seedlings as described by Boucher, C. A. et al., Transposon mutagenesis of *Pseudomonas solanacearum*: Isolation of Tn5-induced avirulent mutants. J. Gen. Microbiol. 1985, 131, 2449-2457.

FIG. 18 shows the effect of synthetic RpoN on *R. solanacearum* plant pathogenicity. FIG. 18A shows an untreated tomato seedling control. FIG. 18B shows a tomato seedling treated with *R. solanacearum* harboring empty vector. FIG. 18C shows a tomato seedling treated with *R. solanacearum* harboring pBRL348 expressing synthetic RpoN*. Under the conditions described, the RpoN synthetic molecule repressed pathogenesis of *R. solanacearum.*

Example 4

Microarray Analysis

This example demonstrates a microarray analysis to determine RpoN regulons and identify cryptic promoters. Over 300 genes were downregulated in *P. aeruginosa* overexpressing RpoN.

To get a global picture of how overexpression of RpoN alters the transcriptome of *P. aeruginosa*, PAO1/pBRL348 or PAO1/pBRL344 cells were grown to the exponential state in LB media at which time total RNA was isolated and subjected to Affymetrix GeneChip® analysis. Many genes involved in quorum sensing (QS) and/or products of QS were significantly downregulated in PA01/pBRL348. For example, the major QS-transcriptional regulator, RhlR, which responds to N-butanoyl-homoserine lactone, experienced a 4-fold reduction in expression. Also, genes that are controlled by the *Pseudomonas* quinolone signal (PQS), e.g., hcnB, chiC, and lecAB, were significantly downregulated.

Four replicates were done per strain tested. For each replicate, an individual colony of P. aeruginosa PAO1/pBRL344 or PAO1/pBRL348 was grown in 1.5 ml of LB at 37° C., and shaking at 250 rpm for 16 h. From this seed culture, 0.25 ml was used to inoculate 50 ml of LB in a 500-ml baffled shake flask. Cultures were grown at 37° C., 250 rpm until an $OD_{600}$ of 0.3 was reached. Cultures were induced with IPTG at a final concentration of 2 mM and grown for 2 h post induction ($OD_{600}$ of 1.5). At this time, 0.5 ml of culture was added to 1 ml of RNAprotect bacterial reagent, and the total RNA was subsequently extracted by performing an enzymatic lysis and proteinase K digestion, followed by purification with the RNeasy Mini kit (Qiagen, California). The purified RNA from all four replicates was combined and then split into four equal parts. The resulting RNA samples were checked for DNA contamination by both PCR and through a Bioanalyzer (Agilent). Microarray experiments were carried out by the Microarray Core Facility (Upstate Medical University, Syracuse, N.Y.) using Affymetrix P. aeruginosa PAO1 GeneChip® arrays.

Microarray studies were performed according to the Affymetrix GeneChip® Expression Analysis Technical Manual (Affymetrix publication 702232 Rev. 3) and previously published protocols (Middleton, F. A., K. Carrierfenster, S. M. Mooney, and S. L. Youngentob. 2009. Gestational ethanol exposure alters the behavioral response to ethanol odor and the expression of neurotransmission genes in the olfactory bulb of adolescent rats. Brain Res 1252:105-16). The pooled RNA samples were used to produce cDNA and profiled using the Affymetrix P. aeruginosa PAO1 GENECHIP® (Affymetrix, Santa Clara, Calif.). This array contains probe sets for over 5,500 ORFs from the PAO1 strain of P. aeruginosa, 199 probe sets corresponding to 100 intergenic sequences, and 117 additional genes from P. aeruginosa strains other than PAO1. The GeneChips were hybridized with constant rotation, then washed and stained on the Fluidics Station according to the Prokaryotic Target Hybridization protocols in the GeneChip Expression Analysis Technical Manual (Affymetrix publication 702232 Rev. 3). Affymetrix software (MicroArray Suite 5.0; MASS) was initially used to perform quality control (Q/C) analysis, calculate the signal intensities from each perfect match prove on the arrays relative to the mismatch probe, and to determine whether or not the gene was present in the sample. After obtaining these metrics, the RMA method was used to normalize the set of arrays in our screen (GeneTraffic software, Stratagene, La Jolla, Calif.). The two pairs of arrays consisting of four chips per condition (empty vector vs. synthetic RpoN in wild type P. aeruginosa and empty vector vs. synthetic RpoN in the rpoN null P. aeruginosa strain) were compared using a simple pairwise t-test with P value adjustment using variance inflation.

Analysis of the data was carried out on the normalized RMA files generated by microarray experiment using MeV from the TM4 Microarray Software Suite (Saeed, A., N. Bhagabati, V. Sharov, E. Howe, J. Li, M. Thiagarajan, J. White, and J. Quackenbush. 2006. TM4 microarray software suite. Meth Enz 411:134-193; Saeed, A., V. Sharov, J. White, J. Li, W. Liang, N. Bhagabati, J. Braisted, M. Klapa, T. Currier, M. Thiagarajan, A. Sturn, M. Snuffin, A. Rezanstev, D. Popov, A. Ryltsov, E. Kostukovich, I. Borsovsky, Z. Liu, A. Vinsavich, V. Trush, and J. Quackenbush. 2003. TM4: a free, open-source system for microarray data management and analysis. Biotechniques 34:374-378).

The results of the microarray analysis are shown in Tables 5-8.

Table 5 shows that these genes are under the control of more than one promoter, including sigma 54 because they are down regulated in both the wild type and native RpoN deletion strains of P. aeruginosa. The underscore represents no gene name associated with the protein. Negative numbers indicate the fold difference in expression of the gene as compared to a wild type strain.

TABLE 5

Genes that are down regulated in both P. aeruginosa PAO1 and P. aeruginosa ΔrpoN (PA06359) expressing synthetic RpoN

| Gene | | | Fold Change | |
|---|---|---|---|---|
| Locus | name | Biological function | PAO1 | PAO6359 |
| PA0200 | — | hypothetical protein | −33.3 | −2.24 |
| PA0459 | — | ClpA/B protease ATP binding subunit | −6.53 | −2.07 |
| PA0542 | — | hypothetical protein | −2.98 | −2.2 |
| PA0852 | cbpD | chitin-binding protein CbpD precursor | −11.61 | −2.15 |
| PA1216 | — | hypothetical protein | −2.98 | −5.82 |
| PA1544 | anr | transcriptional regulator Anr | −2.2 | −2.13 |
| PA1677 | — | hypothetical protein | −2.49 | −4.83 |
| PA1901 | phzC2 | phenazine biosynthesis protein PhzC | −18.51 | −3.18 |
| PA1903 | phzE2 | phenazine biosynthesis protein PhzE | −16.85 | −4.08 |
| PA1904 | phzF2 | phenazine biosynthesis protein | −15.94 | −4.03 |
| PA1905 | phzG2 | pyridoxamine 5′-phosphate oxidase | −22.12 | −4.89 |
| PA2008 | fahA | fumarylacetoacetase | −8.85 | −2.01 |
| PA2009 | hmgA | homogentisate 1,2-dioxygenase | −5.85 | −2.26 |
| PA2031 | — | hypothetical protein | −4.21 | −2.27 |
| PA2067 | — | hydrolase | −3.25 | −2.4 |
| PA2069 | — | carbamoyl transferase | −6.06 | −3.54 |
| PA2193 | hcnA | hydrogen cyanide synthase | −6.43 | −1.88 |
| PA2194 | hcnB | hydrogen cyanide synthase | −5.1 | −1.84 |
| PA2805 | — | hypothetical protein | −4.1 | −2.45 |
| PA3309 | — | hypothetical protein | −3.4 | −2.45 |
| PA3326 | — | ATP-dependent Clp protease proteolytic subunit | −3.71 | −2.97 |
| PA3477 | rhlR | transcriptional regulator RhlR | −4.16 | −2.81 |
| PA3724 | lasB | elastase LasB | −41.43 | −3.23 |
| PA3831 | pepA | leucyl aminopeptidase | −4.08 | −1.99 |
| PA4031 | ppa | inorganic pyrophosphatase | −2.28 | −3.22 |
| PA4067 | oprG | outer membrane protein OprG precursor | −5.22 | −3.38 |
| PA4141 | — | hypothetical protein | −9.76 | −3.11 |
| PA4210 | phzA1 | phenazine biosynthesis protein | −4.67 | −2.9 |
| PA4236 | katA | catalase | −7.22 | −1.82 |
| PA4463 | — | hypothetical protein | −4.32 | −2.69 |
| PA5171 | arcA | arginine deiminase | −5.67 | −1.85 |
| PA5253 | algP | alginate regulatory protein AlgP | −3.2 | −2.18 |

Table 6 shows genes that are down regulated in the P. aeruginosa PAO1 expressing synthetic RpoN but are absent in the P. aeruginosa ΔrpoN (PA06359). These are RpoN controlled genes. This result indicates that the transcription of these genes is antagonized by the synthetic RpoN in a wild type strain. The absence of these genes in the deletion mutant indicates that RpoN cannot be used to transcribe the genes.

TABLE 6

Genes down regulated in the P. aeruginosa PAO1 expressing synthetic RpoN but are absent in the P. aeruginosa ΔrpoN (PA06359).

| Locus | Gene name | Biological function | Fold Change |
|---|---|---|---|
| PA0298 | — | hypothetical protein | −2.93 |
| PA0302 | potG | polyamine transport protein | −2.42 |
| PA0446 | — | hypothetical protein | −2.08 |

TABLE 6-continued

Genes down regulated in the *P. aeruginosa* PA01 expressing synthetic RpoN but are absent in the *P. aeruginosa* ΔrpoN (PA06359).

| Locus | Gene name | Biological function | Fold Change |
|---|---|---|---|
| PA0547 | — | transcriptional regulator | −2.25 |
| PA0865 | hpd | 4-hydroxyphenylpyruvate dioxygenase | −12.08 |
| PA1073 | brad | branched-chain amino acid transport protein | −2.02 |
| PA1080 | flgE | flagellar hook protein | −2.59 |
| PA1094 | fliD | flagellar capping protein | −2.25 |
| PA1323 | — | hypothetical protein | −3.66 |
| PA1546 | hemN | coproporphyrinogen III oxidase | −2.56 |
| PA1784 | — | hypothetical protein | −2.65 |
| PA1874 | — | hypothetical protein | −3.94 |
| PA1888 | — | hypothetical protein | −3.54 |
| PA1939 | — | hypothetical protein | −4.36 |
| PA1967 | — | hypothetical protein | −2.36 |
| PA2110 | — | hypothetical protein | −5.18 |
| PA2111 | — | hypothetical protein | −8.75 |
| PA2444 | glyA2 | serine hydroxymethyltransferase | −8.72 |
| PA2446 | gcvH2 | glycine cleavage system protein H | −4.61 |
| PA2512 | antA | anthranilate dioxygenase large subunit | −2.36 |
| PA2553 | — | acyl-CoA thiolase | −6.6 |
| PA2815 | — | acyl-CoA dehydrogenase | −3.74 |
| PA3014 | faoA | multifunctional fatty acid oxidation complex subunit alpha | −2 |
| PA3188 | — | permease of ABC sugar transporter | −6.25 |
| PA3189 | — | permease of ABC sugar transporter | −3.39 |
| PA3190 | — | binding protein component of ABC sugar transporter | −7.22 |
| PA3250 | — | hypothetical protein | −2.33 |
| PA3336 | — | major facilitator superfamily (MFS) transporter | −2.54 |
| PA3337 | rfaD | ADP-L-glycero-D-mannoheptose 6-epimerase | −8.18 |
| PA3613 | — | hypothetical protein | −2.39 |
| PA3692 | — | Lipotoxon F | −6.27 |
| PA3784 | — | hypothetical protein | −3.18 |
| PA4132 | — | hypothetical protein | −6.41 |
| PA4205 | mexG | hypothetical protein | −5.33 |
| PA4306 | flp | Type IVb pilin | −6.25 |
| PA4328 | — | hypothetical protein | −2.51 |
| PA4500 | — | binding protein component of ABC transporter | −14.65 |
| PA4503 | — | permease of ABC transporter | −3.71 |
| PA4587 | ccpR | cytochrome c551 peroxidase precursor | −5.45 |
| PA4733 | ascB | acetyl-CoA synthetase | −2.56 |
| PA4735 | — | hypothetical protein | −2.08 |
| PA4824 | — | hypothetical protein | −36.69 |
| PA4825 | mgtA | Mg(2+) transport ATPase, P-type 2 | −88.95 |
| PA5167 | — | c4-dicarboxylate-binding protein | −5.39 |
| PA5417 | soxD | sarcosine oxidase delta subunit | −2.73 |
| PA5418 | soxA | sarcosine oxidase alpha subunit | −2.71 |
| PA5421 | fdhA | glutathione-independent formaldehyde dehydrogenase | −5.85 |

Table 7 shows genes that are upregulated in both the wild type and native RpoN deficient background *P. aeruginosa* strains. These results indicate that these genes are not controlled by RpoN directly.

TABLE 7

Genes that are up-regulated in both, *P. aeruginosa* PAO1 and *P. aeruginosa* ΔrpoN (PA06359) expressing synthetic RpoN. The underscore represents no gene name associated with the protein.

| Locus | Gene name | Biological function | PAO1 | PAO6359 |
|---|---|---|---|---|
| PA0578 | — | hypothetical protein | 5.18 | 3.30 |
| PA0579 | rpsU | 30S ribosomal protein S21 | 5.07 | 2.92 |
| PA0659 | — | hypothetical protein | 2.25 | 3.2 |
| PA0734 | — | hypothetical protein | 8.06 | 2.47 |
| PA0758 | — | hypothetical protein | 4.08 | 2.59 |
| PA1317 | cyoA | cytochrome o ubiquinol oxidase subunit II | 2.71 | 2.78 |
| PA1852 | — | hypothetical protein | 3.35 | 3.44 |
| PA3644 | lpxA | UDP-N-acetylglucosamine acyltransferase | 3.02 | 2 |
| PA3645 | fabZ | (3R)-hydroxymyristoyl-ACP dehydratase | 3.18 | 2.36 |
| PA3743 | trmD | tRNA (guanine-N(1)-)-methyltransferase | 6.43 | 2.81 |
| PA3744 | rimM | 16S rRNA-processing protein RimM | 5.11 | 3.22 |
| PA3815 | iscR | IscR | 2.33 | 2.37 |
| PA4115 | — | hypothetical protein | 3.06 | 3.86 |
| PA4433 | rplM | 50S ribosomal protein L13 | 4.03 | 2.69 |
| PA4563 | rpsT | 30S ribosomal protein S20 | 5.15 | 2.45 |
| PA4670 | prs | ribose-phosphate pyrophosphokinase | 3.81 | 2.2 |
| PA4782 | — | hypothetical protein | 2.15 | 3.01 |
| PA5316 | rpmB | 50S ribosomal protein L28 | 5.95 | 2.88 |
| PA5470 | — | peptide chain release factor-like protein | 6.87 | 4.02 |
| PA5471 | — | hypothetical protein | 6.16 | 3.51 |
| PA5570 | rpmH | 50S ribosomal protein L34 | 3.4 | 2.19 |

Table 8 shows genes that are down regulated in *P. aeruginosa* ΔrpoN (PA06359) as compared to wild type *P. aeruginosa*.

TABLE 8

Genes that are down regulated in *P. aeruginosa* ΔrpoN (PA06359) as compared to wild type *P. aeruginosa*.

| Locus | Gene name | Biological function | Fold Change |
|---|---|---|---|
| PA0102 | — | carbonic anhydrase | −2.11 |
| PA0200 | — | hypothetical protein | −2.24 |
| PA0459 | — | ClpA/B protease ATP binding subunit | −2.07 |
| PA0542 | — | hypothetical protein | −2.20 |
| PA0833 | — | hypothetical protein | −1.88 |
| PA0852 | cpbD | chitin-binding protein CbpD precursor | −2.15 |
| PA1215 | — | hypothetical protein | −2.09 |
| PA1216 | — | hypothetical protein | −5.82 |
| PA1217 | — | 2-isopropylmalate synthase | −3.19 |
| PA1342 | — | binding protein component of ABC transporter | −2.88 |
| PA1344 | — | short-chain dehydrogenase | −1.83 |
| PA1414 | — | hypothetical protein | −3.35 |
| PA1533 | — | hypothetical protein | −1.86 |
| PA1544 | anr | transcriptional regulator Anr | −2.13 |
| PA1588 | sucC | succinyl-CoA synthetase subunit beta | −2.04 |
| PA1589 | sucD | succinyl-CoA synthetase subunit alpha | −1.92 |
| PA1677 | — | hypothetical protein | −4.83 |
| PA1869 | — | acyl carrier protein | −3.48 |
| PA1901 | phzC2 | phenazine biosynthesis protein PhzC | −3.18 |
| PA1902 | phzE2 | phenazine biosynthesis protein PhzE | −2.77 |
| PA1903 | phzF2 | phenazine biosynthesis protein | −4.08 |
| PA1904 | phzG2 | pyridoxamine 5′-phosphate oxidase | −4.03 |
| PA1905 | phzC2 | phenazine biosynthesis protein PhzC | −4.89 |
| PA2008 | fahA | fumarylacetoacetase | −2.01 |
| PA2009 | hmgA | homogentisate 1,2-dioxygenase | −2.26 |
| PA2031 | — | hypothetical protein | −2.27 |
| PA2067 | — | hydrolase | −2.40 |
| PA2069 | — | carbamoyl transferase | −3.54 |
| PA2116 | — | hypothetical protein | −2.38 |

TABLE 8-continued

Genes that are down regulated in *P. aeruginosa* ΔrpoN (PA06359) as compared to wild type *P. aeruginosa*.

| Locus | Gene name | Biological function | Fold Change |
|---|---|---|---|
| PA2193 | hcnA | hydrogen cyanide synthase | −1.88 |
| PA2194 | hcnB | hydrogen cyanide synthase | −1.84 |
| PA2321 | — | gluconokinase | −2.48 |
| PA2412 | — | hypothetical protein | −1.96 |
| PA2604 | — | hypothetical protein | −2.09 |
| PA2619 | infA | translation initiation factor IF-1 | −1.93 |
| PA2623 | icd | isocitrate dehydrogenase | −1.85 |
| PA2624 | idh | isocitrate dehydrogenase | −2.60 |
| PA2634 | aceA | isocitrate lyase | −2.06 |
| PA2638 | nuoB | NADH dehydrogenase subunit B | −2.17 |
| PA2639 | nuoD | bifunctional NADH:ubiquinone oxidoreductase subunit C/D | 1.86 |
| PA2641 | nuoF | NADH dehydrogenase I subunit F | −2.40 |
| PA2642 | nuoG | NADH dehydrogenase subunit G | −2.19 |
| PA2644 | nuoI | NADH dehydrogenase subunit I | −1.95 |
| PA2647 | nuoL | NADH dehydrogenase subunit L | −2.39 |
| PA2740 | pheS | phenylalanyl-tRNA synthetase subunit alpha | −1.97 |
| PA2805 | — | hypothetical protein | −2.45 |
| PA3049 | rmf | ribosome modulation factor | −1.92 |
| PA3309 | — | hypothetical protein | −2.45 |
| PA3326 | — | ATP-dependent Clp protease proteolytic subunit | −2.97 |
| PA3477 | rhlR | transcriptional regulator RhlR | −2.81 |
| PA3479 | rhlA | rhamnosyltransferase chain A | −2.50 |
| PA3665 | — | hypothetical protein | −2.00 |
| PA3724 | lasB | elastase LasB | −3.23 |
| PA3831 | pepA | leucyl aminopeptidase | −1.99 |
| PA3880 | — | hypothetical protein | −1.97 |
| PA4031 | ppa | inorganic pyrophosphatase | −3.22 |
| PA4067 | oprG | outer membrane protein OprG precursor | −3.38 |
| PA4141 | — | hypothetical protein | −3.11 |
| PA4210 | phzA1 | phenazine biosynthesis protein | −2.90 |
| PA4211 | phzB1 | phenazine biosynthesis protein | −9.19 |
| PA4236 | katA | catalase | −1.82 |
| PA4348 | — | hypothetical protein | −2.22 |
| PA4463 | — | hypothetical protein | −2.69 |
| PA4602 | glyA3 | serine hydroxymethyltransferase | −2.22 |
| PA4872 | — | hypothetical protein | −1.86 |
| PA4922 | azu | azurin precursor | −2.91 |
| PA5170 | arcD | arginine/ornithine antiporter | −2.34 |
| PA5171 | arcA | arginine deiminase | −1.85 |
| PA5192 | pckA | phosphoenolpyruvate carboxykinase | −2.48 |
| PA5253 | algP | alginate regulatory protein AlgP | −2.18 |
| PA5445 | — | coenzyme A transferase | −2.07 |

CONCLUSION

Table 5 shows genes that are regulated by RpoN directly in *P. aeruginosa*. Table 6 shows genes that are regulated by RpoN but have promoters upstream of RpoN that are involved in their transcription. Table 7 shows genes that are not regulated by RpoN directly and are only turned on the absence of RpoN. Table 8 shows genes that are downregulated in the native RpoN deficient strain of *P. aeruginosa*. In summary, this example demonstrates identification of these genes and how they are regulated using the synthetic RpoN peptide described herein.

Example 5

Use of a Molecular Roadblock to Map the RpoN Regulon of *Pseudomonas aeruginosa* PAO1

This example demonstrates that an RpoN synthetic peptide can be used to map an RpoN regulon of a bacterium, and particularly the RpoN regulon of *Pseudomonas aeruginosa* PAO1.

Introduction

Gene expression in bacteria requires specialized proteins called sigma factors that direct the RNA polymerase (RNAP) to sites of transcription. Most sigma factors belong to the $\sigma^{70}$ family, which recognize a promoter at −10 base pairs upstream of the transcription start site. Whereas bacteria have multiple $\sigma^{70}$-type sigma factors, they normally only have one functional copy of the alternative sigma factor, $\sigma^{54}$ or RpoN. RpoN is an unusual sigma factor and initiates transcription from a highly conserved promoter located −24/−12 upstream of the transcriptional initiation site (1). Additional regulators called enhancer binding proteins or EBPs are required for activating transcription from RpoN promoters (2). The biological functions mediated by RpoN-dependent transcription are quite diverse and range from basic metabolism of various small organic molecules to complex adaptation responses such as biofilm formation (3-6). RpoN is a global transcriptional regulator and is necessary for full virulence in several human pathogens, including *Borrelia burgdorferi* (agent of Lyme disease), *Brucella abortus*, and *Pseudomonas aeruginosa* (7-9). Despite surmounting evidence of the importance of RpoN in processes such as bacterial pathogenesis and bioremediation, there is still no complete picture of the regulatory network governed by RpoN for any given bacterium.

The classic approach to define genes regulated by RpoN involves comparing and contrasting the transcriptomes between a wild-type bacterium and its rpoN-deficient equivalent. Although this direct comparison can provide a wealth of candidate genes that might be regulated by RpoN, it inherently has several critical shortcomings (FIG. 19). For example, genes and operons are typically expressed from more than one promoter, and although in an rpoN-deficient bacterium genes solely controlled by RpoN will not be expressed, a great number of genes that may possess RpoN promoters can still be transcribed from their $\sigma^{70}$-type promoters and as a result are erroneously classified as RpoN independent (10). Another weakness of the classic approach is the inability to observe instances of negative regulation or antagonistic relationships via RpoN. Like many other transcription factors, RpoN functions as a dual regulator. RpoN-mediated repression has been documented to be a naturally occurring method of gene regulation but the depth of this mode of regulation in bacteria is unknown and cannot be readily explored (11, 12). Lastly, the absence of a functional RpoN creates a significant burden on the cell. The catabolism of several commonly occurring organic and inorganic compounds is RpoN dependent, and removal of RpoN restricts the number of substrates that can be metabolized by the bacterium (13). Additionally, an rpoN-deficient bacterium cannot respond or adapt to environmental conditions in a native manner; because of this preexisting condition, it is not possible to observe RpoN-regulated networks in a temporal fashion, e.g., onset of oxygen starvation or biofilm maturation. Collectively, these traits yield a bacterial cell with a physiological and metabolic state that is grossly different than that of its RpoN proficient counterpart. This makes it difficult to discern genes that are regulated by RpoN or whose expression is altered due to pleiotropy associated with the rpoN deficiency.

Materials and Methods

Bacteria, Plasmids and Growth Conditions

Plasmids and oligonucleotides used in the study are given in Tables 9 and 10, respectively.

TABLE 9

Plasmids used in this example are given with relevant characteristics. Abbreviations for antibiotic selection: ampicillin (Am$^R$), kanamycin (Km$^R$) and gentamicin (Gm$^R$).

| Plasmids | Description | Source |
|---|---|---|
| pBBR1MCS-5 | Broad-host range cloning vector; Gm$^R$ | (38) (39) (39) (38) (38) |
| pTrc99a | General cloning expression vector; Am$^R$ | Pharmacia |
| pKH22 | pET-derived expression vector; Am$^R$ | (39) |
| pJ201:42178 | pUC ori, Km$^R$, codon optimized synthetic RpoN region III from *A. aerolicus* | DNA 2.0 |
| pBRL320 | lacI$^Q$-trc promoter of pTrc99a in pBBR1MCS5; Gm$^R$ | This example |
| pBRL327 | codon optimized synthetic RpoN region III from *A. aerolicus* in pKH22; Am$^R$ | This example |
| pBRL344 | same as pBRL320 but both EcoR I and Sac I restriction sites are absent from the MCS region of cloned pTrc99a fragment; Gm$^R$ | This example |
| pBRL348 | pBRL344, codon optimized synthetic RpoN region III from *A. aerolicus* | This example |
| pBRL349 | pBRL348, Y48A RpoN (synthetic) | This example |

TABLE 10

Oligonucleotides used in this example are given (5' to 3') and were purchased from Integrated DNA Technologies (Iowa, U.S.A.).

| Oligonucleotide | Sequence | SEQ ID NO: |
|---|---|---|
| BL330.f | cgtacggttgccaaggctcgtgagatgctgggtattccg | 10096 |
| BL330.r | cggaatacccagcatctcacgagccttggcaaccgtacg | 10097 |
| BL331.f | ggaaacagaccatgcaattccagctcggtacccggggatcc | 10098 |
| BL331.r | ggatccccgggtaccgagctggaattgcatggtctgtttcc | 10099 |
| BL343.f | ttaggcctgaatgccggtg | 10122 |
| BL343.r | atgtacgcagtgattgttaccg | 10123 |

Plasmids were maintained in *E. coli* Top10 (Invitrogen). *P. aeruginosa* studies were done using the strain PAO1 or the rpoN:Ω-Km insertion mutant PAO6359 (32). Bacteriological media was prepared from products of Becton, Dickinson and Company (BD). Bacteria were cultivated in BD Difco™ Lennox media (LB broth; 10 g L$^{-1}$ tryptone, 5 g L$^{-1}$ yeast extract, 5 g L$^{-1}$ NaCl) or M63 minimal media (37). BD Difco™ agar was added to a final concentration of 15 g L$^{-1}$ for solidifying bacteriological media. *P. aeruginosa* strains, PAO1 or PAO6359, were electroporated with plasmids as described (38). For gene expression in recombinant *P. aeruginosa* strains, isopropyl β-D-1-thiogalactopyranoside (IPTG) was used at a final concentration of either 1 or 2 mM depending on the experiment (see below). Antibiotics were used at the following concentrations: ampicillin, 100 mg L$^{-1}$ *E. coli*; kanamycin, 50 mg L$^{-1}$ *E. coli* or 500 mg L$^{-1}$ *P. aeruginosa*; gentamicin, 20 mg L$^{-1}$ *E. coli* or 30 mg L$^{-1}$ *P. aeruginosa*.

Construction of RpoN Molecular Roadblock

To construct a tightly regulated, IPTG-inducible expression vector for *P. aeruginosa*, the region encoding LacI$^Q$ and the trc-promoter of pTrc99a (Pharmacia Biotech, Sweden) was cloned into the Xba I and Sph I sites of the broad-host range plasmid pBBR1MCS-5 to yield pBRL320 (39). Next, the EcoR I and Sac I sites of the multiple cloning region of the inserted pTrc99a fragment in pBRL320 were removed via site-directed mutagenesis using Quikchange™ (Stratagene) and the oligonucleotides BL331.f/BL331.r (Table S2) to generate the plasmid pBRL344.

A gene encoding the last 60 amino acids of the RpoN of *A. aeolicus* was synthesized and codon optimized for expression in *E. coli* by DNA 2.0 (Menlo Park, Calif.). For cloning purposes, Nde I and Sac I restriction sites were engineered into the 5' and 3' ends, respectively, of the synthetic rpoN gene. The synthetic rpoN gene was then subcloned from pJ201:42178 into the Nde I/Sac I sites of the *E. coli* expression pET-vector pKH22 to give pBRL327 (40). The pBRL327 plasmid was then digested with Xba I and Sac I to liberate the synthetic rpoN gene with an upstream ribosome binding site. This fragment was cloned into the Xba I/Sac I sites of pBRL344 to yield pBRL348.

To generate an attenuated RpoN molecular roadblock, the tyrosine at position 48 was changed into alanine using Quikchange™ (Stratagene, Santa Clara, Calif.) with pBRL348 as the template and the oligonucleotides BL330.f/BL330.r (Table S2) (18). The resulting plasmid pBRL349 encodes for the Y48A RpoN molecular roadblock.

Analysis of Virulence Factors

*P. aeruginosa* strains, PAO1 or PAO6359, were transformed with either pBRL344 (empty plasmid), pBRL348 (RpoN*) or pBRL349 (Y48A RpoN*) plasmids (38). These recombinant strains were used for all virulence factor experiments.

Motility.

Motility of *P. aeruginosa* was assessed as described (37). Plates used in motility assays were supplemented with 2 mM IPTG. Single colonies of recombinant *P. aeruginosa* were stabbed onto (i) M63 minimal media supplemented with 0.5% Difco™ casamino acids, 0.2% glucose and 0.3% agar or (ii) LB with 0.3% agar. Motility plates were grown for 16 h at 37° C.

Hemolytic Activity.

Recombinant *P. aeruginosa* was patched onto LB-solid media supplemented with 5% sheep blood, 30 mg L$^{-1}$ gentamicin and 1 mM IPTG. Patched plates were grown at 37° C. for 16 h.

General Proteases.

To detect nonspecific protease activity, single colonies of recombinant *P. aeruginosa* were patched onto LB-solid media supplemented with 2% non-fat dry milk, 30 mg L$^{-1}$ gentamicin and 1 mM IPTG. Patched plates were grown at 37° C. for 16 h. Degradation of protein was determined by colony and/or halo formation.

Elastase.

Elastolytic activity was assayed by the breakdown of elastin-Congo red (41). In triplicate, recombinant P. aeruginosa PAO1 was grown in PTSB broth (50 g $L^{-1}$ Difco™ Peptone, 2.5 g $L^{-1}$ tryptic soy broth, 5 g $L^{-1}$ yeast extract) supplemented with 30 mg $L^{-1}$ gentamicin at 37° C. to an $OD_{600}$ of 0.15. At this time, IPTG was added to a final concentration of 2 mM, and the induced cultures were grown for an additional 5 h. After this 5 h incubation, cells were removed by centrifugation and passage through a 0.2 micron filter. Next, 1 mL of the cleared supernatant was added to 2 mL elastase reaction buffer (0.1 M Tris, pH 7.2, 1 mM $CaCl_2$, 10 g $L^{-1}$ elastin-Congo red). Reactions were incubated at 37° C. with gentle shaking for 7 h and subsequently centrifuged to remove insoluble elastin-Congo red. The absorbance of liberated Congo red in the supernatant was measured at 459 nm.

Pyoverdine.

Production of pyoverdine from P. aeruginosa in King's B medium (20 g $L^{-1}$ Difco™ bacteriological peptone, 1.5 g $L^{-1}$ $K_2HPO_4$, 1.5 g $L^{-1}$ $MgSO_4.7H_2O$, 1% v/v glycerol) was determined as follows. In triplicate, 2 mL of King B medium was inoculated with 0.5% of seed culture and then grown to an $OD_{600}$ of 0.3 at 37° C. with shaking at 250 rpm. IPTG was added to a final concentration of 2 mM, and the induced cultures were grown for an additional 16 h. After incubation, cells were cleared by passage through a 0.2 micron filter. The cleared filtrate was then assayed at 408 nm for pyoverdine.

Pyocyanin.

Production of pyocyanin from P. aeruginosa in LB was determined as described (42). In triplicate, 2 mL of LB was inoculated with 0.5% of seed culture and then grown to an $OD_{600}$ of 0.3 at 37° C. with shaking at 250 rpm. IPTG was added to a final concentration of 2 mM, and the induced cultures were grown for an additional 16 h. After incubation, cells were cleared by passage through a 0.2 micron filter, and the pyocyanin was extracted from 1.5 ml of the cell-free broth by the addition of 1 ml of chloroform. The resulting chloroform phase was then extracted with an equal volume of 0.2 M HCl, and the pink aqueous phase was assayed at 520 nm for pyocyanin.

RNA Isolation and Microarray Analysis

RNA isolation and microarray analysis were done in quadruplicate. Per replicate, a single clone of P. aeruginosa harboring either pBRL344 or pBRL348 was grown in 2 mL LB supplemented with 30 mg $L^{-1}$ gentamicin at 37° C., 250 rpm, for 16 h. This seed culture was then used (0.5% v/v) to inoculate 50 mL (in a 500-mL baffled shake flask) of LB supplemented with 30 mg $L^{-1}$ gentamicin. The inoculated shake-flask cultures were grown at 37° C., 250 rpm, until an $OD_{600}$ of 0.2, and then IPTG was added to a final concentration of 1 mM to induce expression of the RpoN molecular roadblock. The induced cells were grown for 2 h at which time 0.5 mL of culture was removed and added to 1 mL of RNAprotect® reagent. Total RNA was purified from the samples using the enzymatic lysis and proteinase K digestion method of Qiagen RNeasy with an on-column DNase digestion. Purified RNA samples were checked for DNA contamination by Polymerase Chain Reaction (PCR) with the primers BL343.f/BL343.r, which were designed to amplify the rplU gene (43) (Table S2). Purified RNA samples were also analyzed for quality using a Bioanalyzer (Agilent).

Microarray studies were carried out by the Microarray Core Facility (Upstate Medical University, Syracuse, N.Y.) using GeneChip® P. aeruginosa PAO1 Affymetrix arrays. Experiments were performed according to the Affymetrix GeneChip© Expression Analysis Technical Manual (Affymetrix publication 702232 Rev. 3) and published protocols established at SUNY Upstate (Syracuse, N.Y.) (44). For initial data processing, the Affymetrix software (MicroArray Suite 5.0; MASS) was used for quality control (Q/C) analysis, calculating the signal intensities from each perfect match prove on the arrays relative to the mismatch probe, and determining whether or not the gene was present in the sample. The RMA method was used to normalize the set of arrays in our screen (GeneTraffic software, Stratagene, La Jolla). The MultiExperiment viewer (MeV v4.6.2) was used for subsequent statistical analysis. To identify genes displaying a significant difference in intensities, a T-test between subjects was performed using p-values based on all permutations and overall alpha value fixed at 0.05. False discoveries were addressed using the standard Bonferroni correction. Microarray data was deposited in Gene Expression Omnibus and is accessible through GEO Series accession number GSE35632. (45).

Predictive Modeling of RpoN Promoters

Bacterial $\sigma^{54}$ promoters were identified genome-wide using a modified version of the PromScan Perl script (available at www.sigma54.ca/PromoterApp/Web/promscandata.pl), which was originally developed by Studholme (19). PromScan relies on a scoring algorithm that fits a position weighted matrix (PWM) to every location on both strands of a genome. The scoring function calculates the Kullback-Leibler divergence between the probability of observing a particular base from the matrix and the probability of that base occurring randomly in the genome. While the Kullback-Leibler divergence provides a measure of difference between two probability distributions, it has been shown that this property provides a reasonable estimate for binding energy contributions in the context of sequence-specific DNA binding proteins (2) and has been used extensively for this application. The original PromScan algorithm was further modified to output all hits within a genome, including intragenic hits, with a normalized score of 65 or higher. The Perl script was run on Windows using Strawberry Perl (free from strawberryperl.com/). The script used as inputs were the P. aeruginosa PAO1 DNA sequence file (FNA FASTA file from NCBI's FTP Genome Database (46)(46)(45)(45)(45), see External Database S1, FTP Folder found at ftp.ncbi.nlm.nih.gov/genomes/Bacteria/
Pseudomonas_aeruginosa_PAO1_uid57945/) and a $\sigma^{54}$ promoter position weighted matrix file that is derived from on 186 known $\sigma^{54}$ promoter sites (1). The script output consisting of a score, strand direction, and by location for each hit was captured in a text file and imported into a SQL server database (Microsoft SQL Server 2008 R2 Express free from www.microsoft.com/express/). The results were cross referenced using annotation data from PTT files and RNT files containing gene and RNA gene data respectively (also from NCBI's FTP Genome Database). The results are can be found below (External Database S2, P. aeruginosa PAO1 rpoN Score Data: found at www.sigma54.ca/PromoterApp/Web/setparameters.aspx?organism=NC_002516.2 &matrix=RPON.Matrix).

A C# program (www.sigma54.ca/source/DataExport/) was used to link hits with gene start sites on both the positive and reverse strands. A web interface was built to access and filter the data based on a variety of parameters including score and distance from the ORF. In addition, microarray data was imported into the server and linked to the hit and gene annotation data. A webpage displaying the microarray data was created with the ability to show the computationally predicted hits of both the coding and non-coding strands (External database S3, MicroArray Results with RpoN binding sites: found at www.sigma54.ca/PromoterApp/Web/PAmarray.aspx).

Results

Design and Construction of the RpoN Molecular Roadblock.

Figure 20:
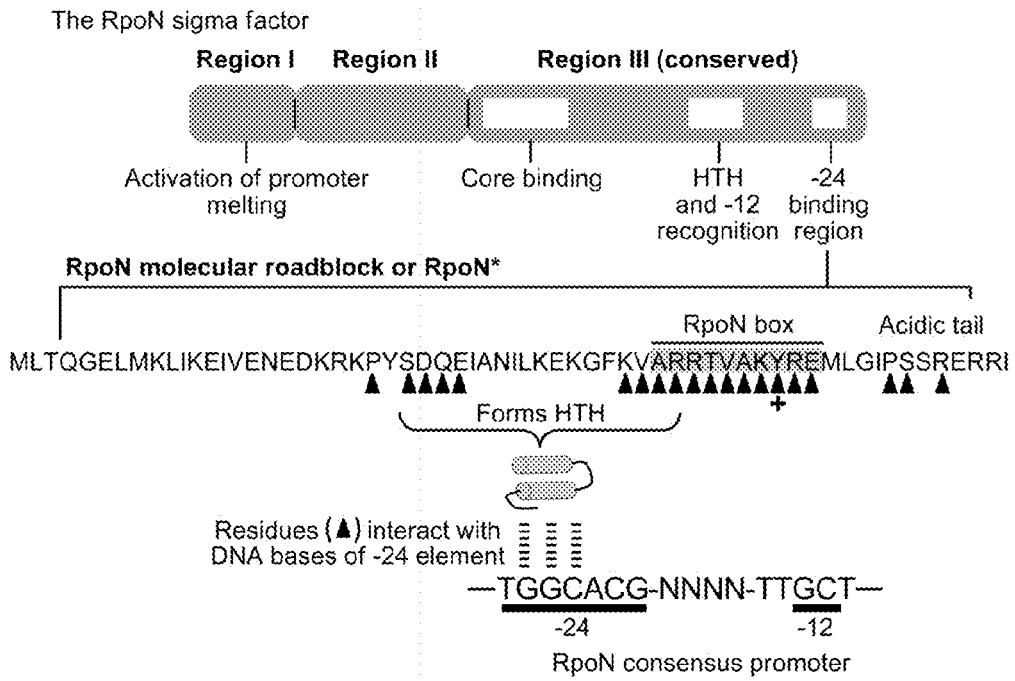
FIG. 20: Schematic illustration of the RpoN protein and the RpoN molecular roadblock. RpoN consists of three regions. Region III contains the highest degree of conservation among the three regions and is involved with binding to the −24/−12 conserved promoter elements. The RpoN* peptide comprises amino acids 376-400 of Region III of RpoN and contains amino acids that bind specifically to the −24 element of RpoN promoters. Changing the tyrosine residue (Y48, labeled as +) to alanine reduces the binding and transcriptional activity of RpoN. Region III is conserved among RpoN proteins in many bacteria.

Because of the central, crucial role played by RpoN in bacterial physiology and pathogenesis, and the inability of current methods to define regulons controlled by this sigma factor, it was necessary to develop a robust, simplistic tool for mapping bacterial RpoN regulatory networks. To this end, we exploited the unique binding properties of the RpoN protein for its cognate promoter. Unlike other sigma factors, RpoN can bind to its promoter without interacting with the RNA polymerase (RNAP), although this binding efficiency is 10-fold lower than that of the RpoN:RNAP complex (14). Importantly, RpoN proteins are highly conserved in their C-terminal DNA binding domains. This DNA binding domain of RpoN binds specifically to the −24 element of RpoN promoters with high affinity ($K_d$~114 nM) (15). Using this interaction to our advantage, a gene encoding a peptide resembling the last 60 amino acids of the RpoN from the thermophile *Aquifex aeolicus* was synthesized and codon-optimized for expression in the lab-prototype bacterium, *Escherichia coli* (FIG. 20). This short peptide, termed the RpoN molecular roadblock or RpoN*, will bind to the −24 element of RpoN promoters and antagonize transcription from these loci (FIG. 19). Unlike full-length RpoN, RpoN* cannot interact with native EBPs or RNAP and therefore minimally impacts the transcriptional machinery of the bacterial cell. For example, native sigma factors compete with each other for RNAP to initiate transcription, because RpoN* cannot interact with RNAP, it will not disturb the RNAP: sigma factor pools (16). When used with transcriptomic profiling and predictive modeling, the RpoN molecular roadblock can identify all sites of RpoN regulation, including points of regulation that could not be visualized before such as genes possessing multiple promoters and/or under negative control by RpoN.

The RpoN Molecular Roadblock Inhibits Motility and Production of Virulence Factors of *P. aeruginosa*.

Figure 21:
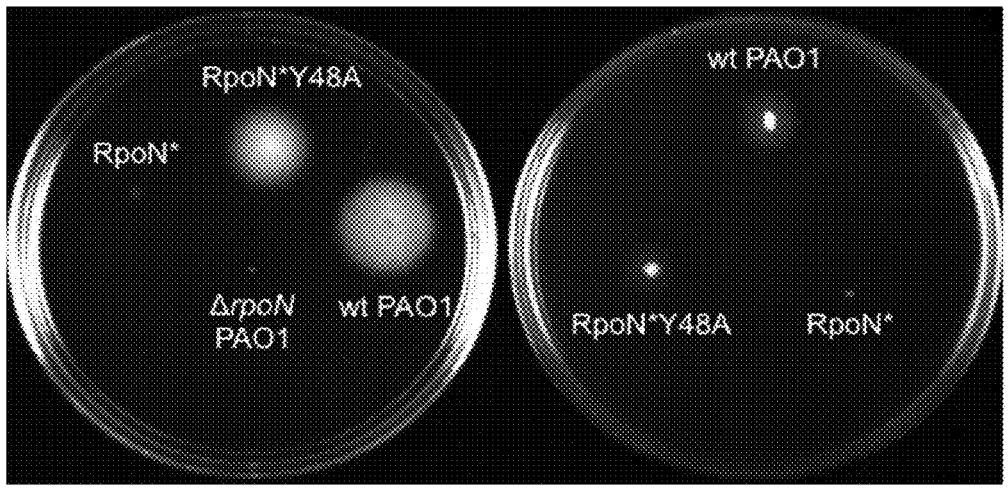
FIG. 21: Expression of RpoN molecular roadblock inhibits both swarming (left) and twitching (right) motility of *P. aeruginosa* PAO1. Colonies of recombinant *P. aeruginosa* PAO1 harboring either empty plasmid, RpoN* or Y48A RpoN* were stabbed onto either i) M63 minimal media supplemented with 0.2% glucose, 0.5% casamino acids and 0.3% agar (swarming) or ii) thin-layer LB plates in polystyrene petri dishes (twitching). Plates were supplemented with 2 mM IPTG to induce expression of recombinant proteins and grown for 16 h at 37° C. Swarming motility of recombinant rpoN-deficient *P. aeruginosa* PAO1 (PA06359/pBRL344) was done for comparison.
Figure 22:
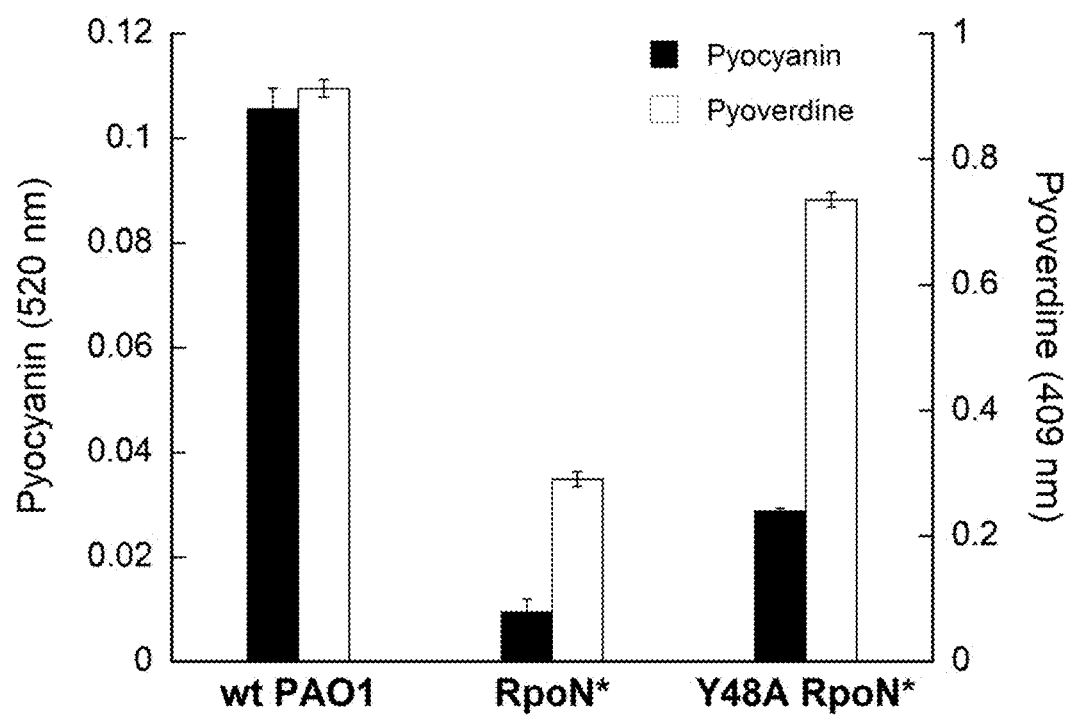
FIG. 22: Expression of RpoN molecular roadblock reduces pyocyanin and pyoverdine production from *P. aeruginosa* PAO1 grown on LB. Recombinant *P. aeruginosa* PAO1 harboring either empty plasmid (wt PAO1), RpoN* or Y48A RpoN* were evaluated for the production of pyocyanin and pyoverdine in LB. Standard error bars are shown.
Figure 23:
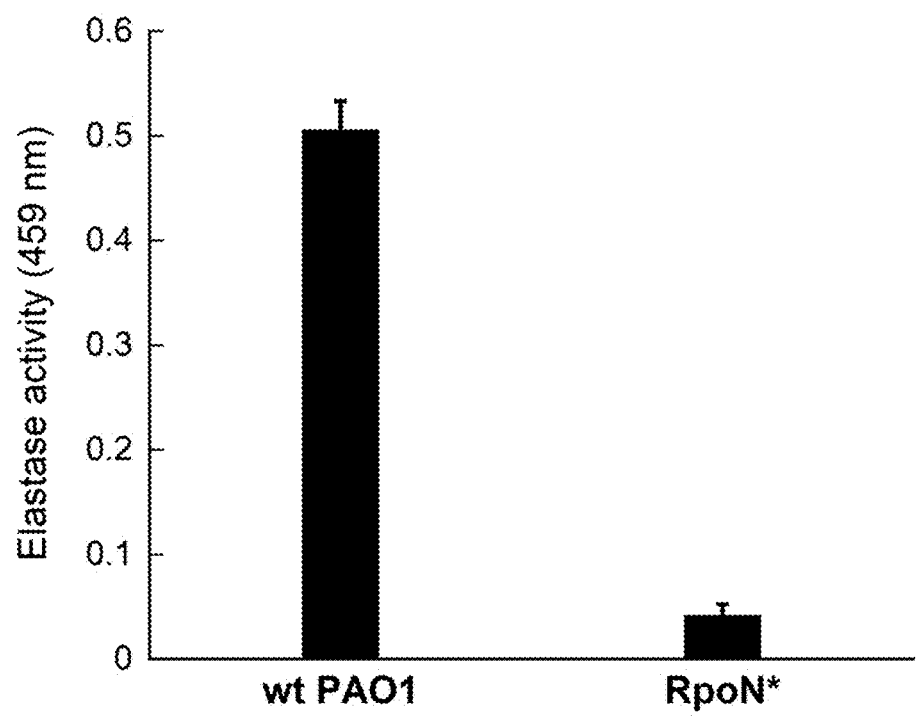
FIG. 23: Expression of RpoN molecular roadblock reduced the production of elastase from *P. aeruginosa* PAO1 grown on PTSB. Recombinant *P. aeruginosa* PAO1 harboring either empty plasmid (wt PAO1) or RpoN* were grown on PTSB for 7.5 h at 37° C. Cells were removed from the broth, and the resulting cell-free samples were assayed for the breakdown of elastin-Congo red. Standard error bars are shown.
Figure 24:
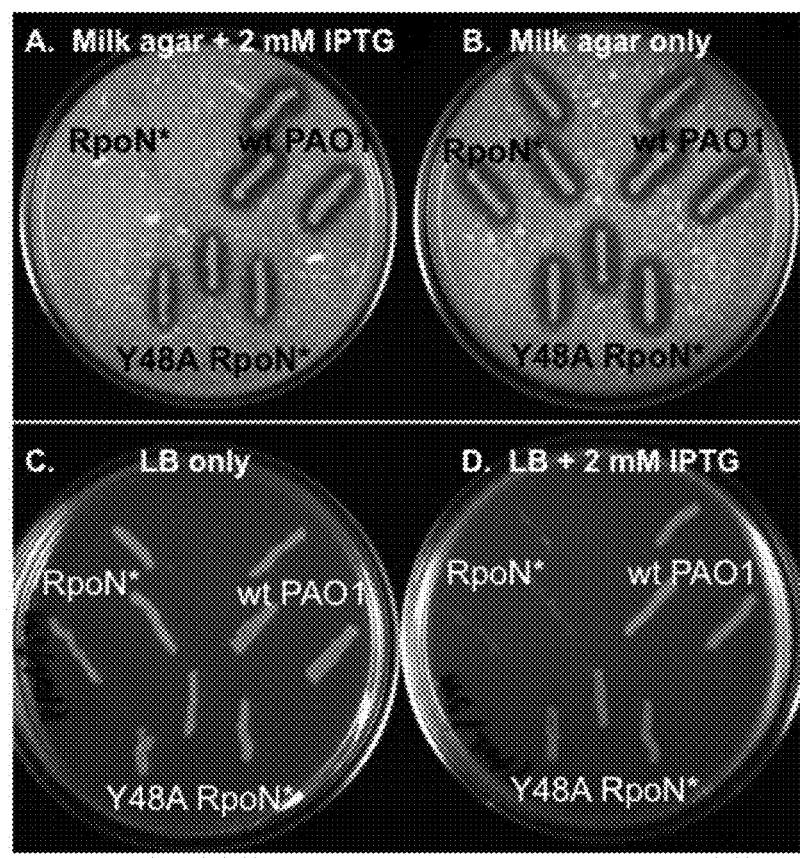
FIG. 24: Expression of RpoN molecular roadblock inhibits growth of *P. aeruginosa* PAO1 on rich media, including milk agar (top) and LB (bottom). Recombinant *P. aeruginosa* PAO1 harboring either empty plasmid (wt PAO1), RpoN* or Y48A* RpoN were patched onto rich-solid media and growth was assessed after 16 h at 37° C.
Figure 25:
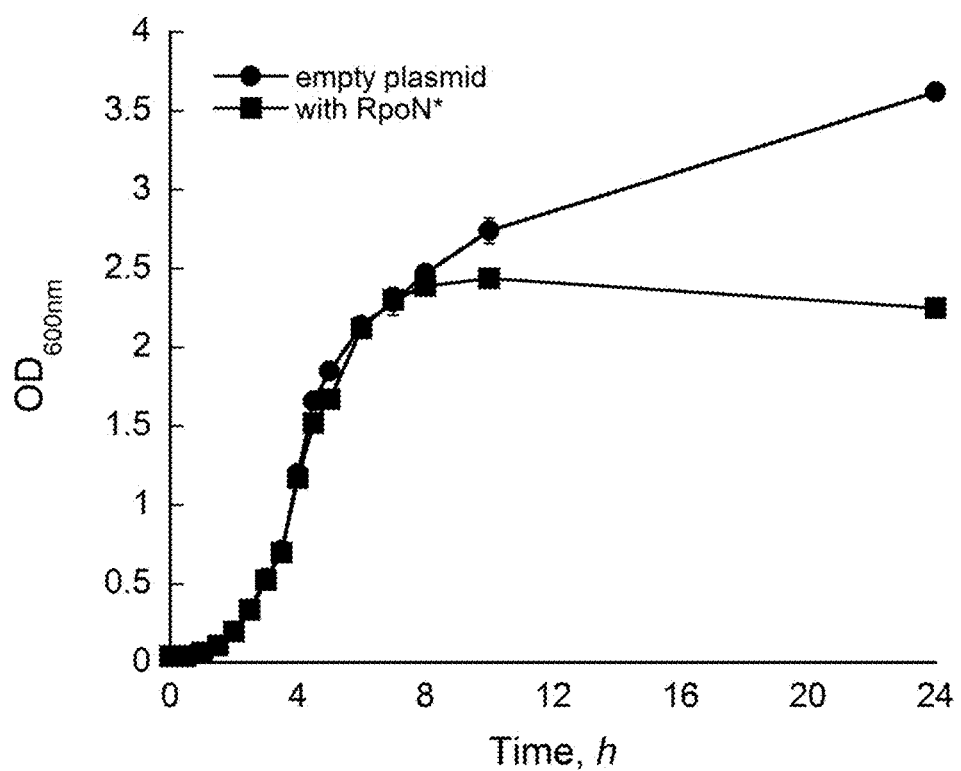
FIG. 25: Expression of RpoN molecular roadblock inhibited the growth of *P. aeruginosa* PAO1 following 3 h post induction. Recombinant *P. aeruginosa* PAO1 harboring either empty plasmid or RpoN* were grown in LB at 37° C., 250 rpm. Cultures were induced at an $OD_{600nm}$ of 0.5 with 1 mM IPTG. As shown, within 3 h post induction, RpoN* reduced the growth of *P. aeruginosa* PAO1. All results shown are the average values from triplicate samples. Standard error bars are shown.

To test the functionality of the RpoN molecular roadblock, it was used to antagonize known RpoN-mediated responses in the opportunistic and model pathogen *P. aeruginosa* PAO1. RpoN* was cloned into a broad-host range plasmid under the control of an inducible trc-promoter to enable precise timing of RpoN* expression. Introduction of the plasmid-based RpoN* into *P. aeruginosa* PAO1 significantly impeded the organism's motility on semisolid media (FIG. 21), which is a biological function that requires RpoN-mediated transcription (17). The RpoN molecular roadblock also decreased the production of the siderophore pyoverdine, phenazine compounds such as pyocyanin, and the major extracellular protease, elastase (FIGS. 22 and 23). Expression of RpoN* prevented the growth of the bacterium on a wide range of rich media, and alleviation of this growth inhibition could only be achieved with the addition of free amino acids (FIG. 24). To gain insight into whether these phenotypes were a result of RpoN* binding, the tyrosine residue (Y48) located within the RpoN box of RpoN* was replaced by alanine using site-directed mutagenesis. As shown previously for full-length RpoN, this tyrosine-alanine mutation reduces the binding and transcriptional activation efficacy of the RpoN protein (18). As expected, the Y48A RpoN* peptide generated similar traits to that of wild-type *P. aeruginosa* PAO1 (FIGS. 21, 23, and 24). The expression of RpoN* did not slow down the growth rate of *P. aeruginosa* in liquid culture until ~3 hours post induction (FIG. 25). It was initially suspected that the reduction of these virulence factors and growth rate was due to a pleiotropic and toxic effect of the RpoN molecular roadblock via non-specific DNA binding. However, examination of the transcriptome of *P. aeruginosa* expressing the RpoN molecular roadblock revealed a completely different story.

Mapping the RpoN Regulon of *P. aeruginosa*.

Having evidence that expression of the RpoN molecular roadblock could inhibit RpoN-related functions, we next attempted to redefine the RpoN regulon for *P. aeruginosa* PAO1 using a combination of predictive bioinformatics and microarray analysis. Putative binding sites for the RpoN molecular roadblock in *P. aeruginosa* PAO1 were identified in silico using an algorithm based on the PromScan software and an RpoN promoter positional weighted matrix (1, 19). This algorithm has been applied to ascertain putative RpoN promoters from over 60 sequenced genomes covering a wider range of bacterial phyla (data available at www.sigma54.ca).

Figure 26:
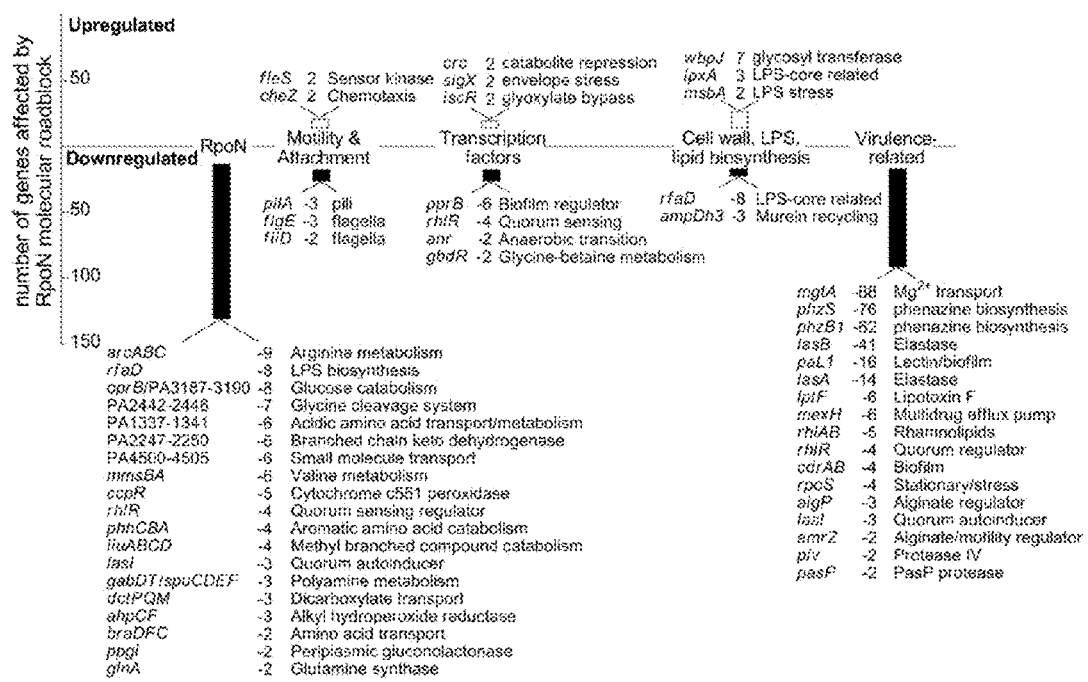
FIG. 26: Expression of the RpoN molecular roadblock altered the transcription of over 700 genes. The majority of downregulated genes possessed high-scoring putative RpoN binding sites and were found to be involved in metabolism. The RpoN molecular roadblock had a negative effect on the transcription of quorum-related genes, e.g., virulence factors, and other key transcriptional regulators such as the anaerobic transition regulator, anr. Note that the hypothetical (~250 total) and ribosomal (~70) genes were excluded from the above figure.

Microarray experiments were done in quadruplicate using Affymetrix GeneChips™. Cells of *P. aeruginosa* PAO1 harboring plasmids capable of inducible RpoN* expression or the empty vector equivalent were grown in rich media and upon entering mid-exponential growth, expression of RpoN* was induced. At two hours post induction, total RNA was isolated and subjected to transcriptiomic analysis. The two-hour time point was chosen, because it gave sufficient time for recombinant RpoN* to be expressed and saturate RpoN promoters. Notably, we observed no difference in growth rates between *P. aeruginosa* with and without RpoN* but there was a clear phenotypic difference based on the presence and absence of the blue-chromophore pyocyanin in cultures with empty plasmid as compared to cells expressing RpoN*. A total of ~700 genes were found to be differentially expressed at least 2-fold in the presence of the RpoN molecular roadblock. The majority of these genes (>400) were downregulated whereas those involved in lipopolysaccharide and ribosomal biosynthesis constituted the preponderance of upregulated genes. After crosschecking downregulated genes with their predicted RpoN promoters, a total of 150 genes were classified as being under the control of RpoN and can be broadly divided into proteins involved in metabolism, stress/survival, or cell signaling (FIG. 26).

RpoN Network in General Metabolism.

Figure 27:
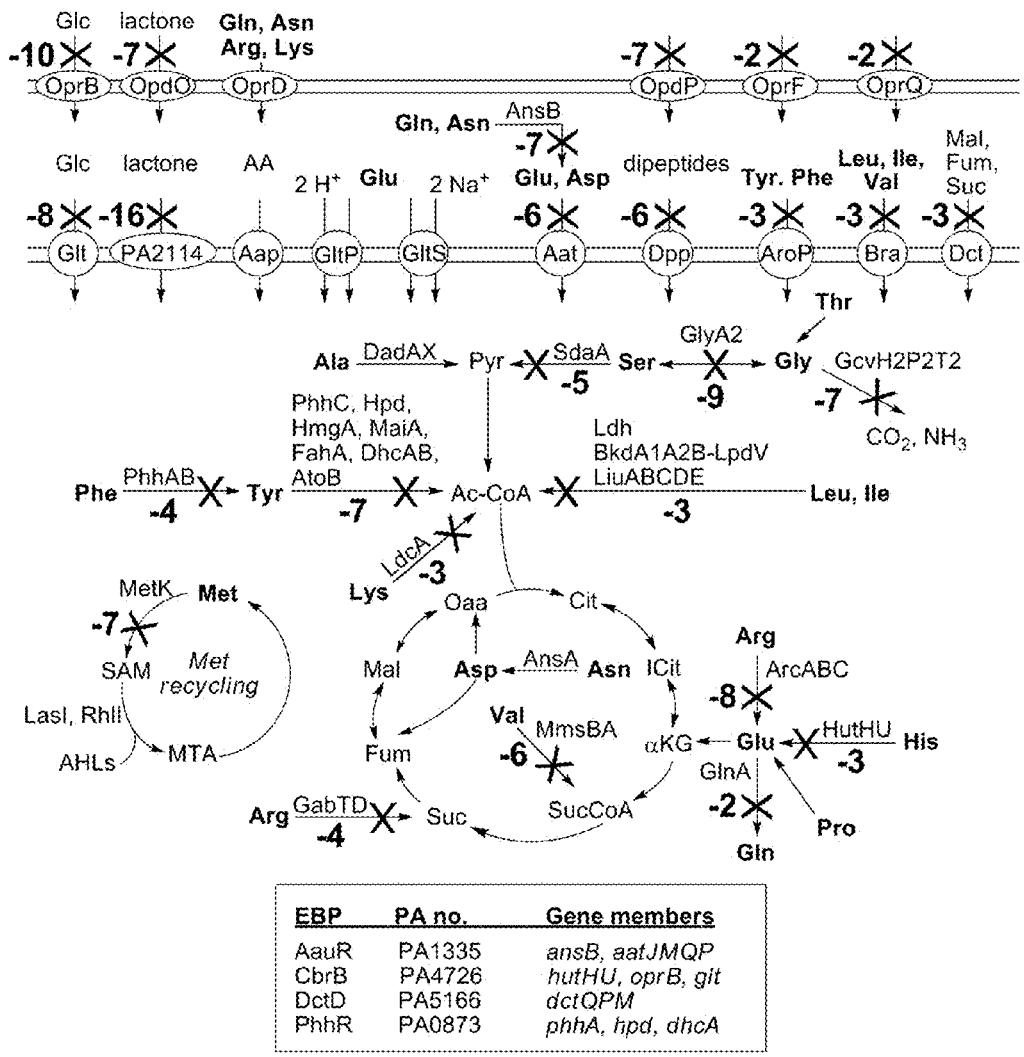
FIG. 27: RpoN controls multiple facets of carbon and nitrogen metabolism in *P. aeruginosa*. Expression of the RpoN molecular roadblock downregulated transcription of genes involved in assimilating diverse carbon and nitrogen sources. Bold numbers indicate fold down regulation of genes encoding proteins and "X" indicates potential blockage of transport or catabolic ability due to the repression of genes encoding these proteins via the RpoN molecular roadblock. Several of these metabolic pathways were previously observed to be under the control of RpoN EBPs, including AauR, PhhR, DctD and CbrB. The microarray data generated in our study supports these earlier findings but also suggests that RpoN regulates single carbon metabolism (glycine cleavage system and SAM biosynthesis), hexose transport and the catabolism of branched-chain amino acids.

Transcription of genes involved in the consumption of sugars, amino acids and dicarboxylates was repressed under expression of the RpoN molecular roadblock (FIG. 27). This data was consistent with prior experimental evidence of RpoN and its cognate EBPs functioning in carbon metabolism of *Pseudomonas* spp. A classic example of this is the RpoN regulation of the glutamine synthase gene, glnA, which requires the EBP NtrC, and is activated under nitrogen limitation (20). As expected, transcription of the glnA locus declined 2-fold as a result of expression of RpoN*. In another example, the EBP PhhR is necessary for aromatic amino acid catabolism, and genes previously cataloged into the PhhR regulon were downregulated as a result of RpoN* expression (21). The EBP AauR regulates transport of acidic amino acids, and as anticipated, RpoN* repressed transcription of AauR-controlled genes (22). The more global acting EBP CbrB functions in the assimilation of a wide variety of compounds, including several common amino acids (alanine, arginine, and histidine) (23). It is also known that AcbrB *P. aeruginosa* is impaired in the use glucose and mannitol as sole carbon sources but the reason for this trait has remained unclear (24). Based on our predictive bioinformatics, the sugar-specific outer membrane porin, OprB, and the hexose transporter, GlcKGF, have high-scoring putative RpoN promoters, and their transcription decreased by 8-fold when the RpoN molecular roadblock was expressed. Transcription of these loci appeared to be RpoN-dependent and a key determinant in sugar utilization by *Pseudomonas*, thus providing a probable explanation for the growth limitation observed with the cbrB null mutation. Recently, genes encoding a dicarboxylate transport system, DctPQM, were found to be under the control of the EBP DctD, and this regulation was confirmed by expression of RpoN*, which downregulated the transcription of the dctPQM operon by 3-fold (25). In addition to targeting and identifying genes regulated by RpoN and known EBPs, several new metabolic conversions regulated by RpoN were discovered in this example. Single carbon metabolism via the glycine cleavage system, the recycling of S-adenosylmethionine, breakdown of branched chain amino acids and the transcription of the terminal pathway for arginine and polyamine degradation, the gabTD genes, were found to be RpoN-dependent. Interestingly, transcriptional regulator(s) of the gabTD operon have not been identified but direct control via RpoN coincides with previously observed RpoN regulation of other genes involved in arginine and polyamine utilization (26). These findings greatly expand our knowledge of RpoN regulation and suggest that RpoN-mediated transcription is widespread across all points of bacterial metabolism.

We also observed that RpoN regulates transcription of several genes whose products are associated with cell stress and survival (12, 27). One of the more interesting members of this group was the rfaD gene, which encodes a required enzyme for the biosynthesis of core lipopolysaccharide (LPS). The rfaD gene has a predicted RpoN promoter of a score of 81 and has been shown to be regulated by RpoN and the EBP NtrC in the human-related pathogen *Vibrio vulnificus* (28). Transcription of rfaD declined 8-fold due to RpoN* expression, and this drop in expression of rfaD was associated with an increase in transcription for several LPS biosynthesis genes as exemplified by the LPS-stress protein, MsbA. Some other notable genes with observed RpoN regulation identified by our study include mgtA ($Mg^{2+}$ transport), rmf (ribosome modulation factor), rpoS, ccpR (cytochrome c551 peroxidase), and PA3309 (universal stress protein).

RpoN in Cell Signaling of *P. Aeruginosa*.

RpoN* also negatively regulated quorum sensing (QS) in *P. aeruginosa*. Cell signaling in *P. aeruginosa* consists of three interconnecting networks: the two homoserine lactone-responsive regulators, RhlR and LasR, and signaling via 2-alkyl-4-quinolones or PQS (29, 30). Expression of the RpoN molecular roadblock significantly reduced the transcription of two major QS proteins RhlR and the autoinducer synthase LasI. This antagonistic action at the rhlR/lasI loci led to downregulation of >70 genes suspected to be regulated by RhlR/LasR signaling, including the virulence factors elastase, protease IV, esterase, rhamnolipids, and transcriptional regulators, e.g., RpoS and PprB (31). Because the rhlR/lasI loci can be transcribed from multiple promoters, the direct antagonistic actions of RpoN on these genes cannot be observed by simply comparing transcriptome data between wild-type and rpoN-deficient *P. aeruginosa*. Higher levels of QS molecules have been observed in rpoN-deficient *P. aeruginosa*, which supports the microarray results generated by RpoN* (32). Together, they suggest that native RpoN might be a natural negative regulator of QS in *P. aeruginosa*. It was also observed that the PQS signaling system was transcriptionally intact in *P. aeruginosa* expressing the RpoN molecular roadblock, but its end product pyocyanin was greatly reduced. The microarray results showed that the genes required for phenazine biosynthesis were down by 8-fold in the presence of RpoN*; both phenazine biosynthetic clusters possess high-scoring putative RpoN promoters. Overall, the decreased production of pyocyanin can be attributed to the downregulation of genes involved in phenazine biosynthesis and elevated levels of intracellular tyrosine, which limits precursor availability for compounds derived from the shikimic acid pathway, including phenazines (33).

Because native RpoN can bind to its cognate promoter without interacting with RNA polymerase, it serves as a repressor of transcription for genes regulated by multiple promoters (12). This type of regulation is impossible to examine with rpoN-deficient strains alone. To discover loci that are under the control of RpoN and may possess multiple promoters, transcriptomics were compared between rpoN-deficient *P. aeruginosa* PAO1 expressing either RpoN* or the empty vector equivalent. The results of these microarrays identified several genes (~30) that were antagonistically regulated by RpoN* (FIG. 28). For example, isocitrate lyase activity has been found to be negatively regulated by RpoN in *P. aeruginosa*, and the isocitrate lyase gene (aceA), was observed to be downregulated by 2-fold in the presence of the RpoN molecular roadblock (34). Another key antagonistic interaction that was discovered involves the anr gene, which encodes a regulator of anaerobic metabolism. The anr gene is known to possess an RpoN promoter but was previously thought to be RpoN-independent (10). However, its transcription decreased 2-fold as a result of expression of RpoN*, suggesting the specific antagonistic nature of RpoN on expression of anr. Indeed, several gene members of the Anr regulon were predicted to have strong probable RpoN promoters and downregulated by RpoN* expression, including genes encoding the hydrogen cyanide synthase (hcnABC) and the arginine deaminase pathway (arcABC) (35). This suggests that RpoN might aid in coordinating overall metabolism at the onset of anaerobic transition.

Discussion

Use of the RpoN molecular roadblock in *P. aeruginosa* PAO1 readily identified hundreds of genes under the control of RpoN, thereby providing an accurate and temporal snapshot of RpoN regulation within the cell. However, there were some unexpected results. It was originally speculated that genes involved in the biosynthesis of flagella would be noticeably downregulated, because these genes are known to be transcribed by RpoN in *P. aeruginosa*. Despite the few flagella genes that were downregulated by the RpoN molecular roadblock, the majority remained unchanged. It was also noticed that the cognate sensor kinase, FleS, for the EBP FleR was upregulated. We propose that the flagella loci may represent a sort of 'hot' site for RpoN regulation in which the native RpoN:RNAP complex is effectively able to out compete the RpoN roadblock for gene activation. As previously stated, the RpoN:RNAP holoenzyme has stronger affinity for the RpoN promoter than that of RpoN alone (>10-fold difference) and this phenomenon would explain why certain RpoN-controlled genes were undetected with the RpoN molecular roadblock. In contrast, detection of RpoN regulation at some of these 'hot' loci was due to a probable titration effect caused by the RpoN molecular roadblock. Because of the limited availability of RpoN:RNAP holoezymes, RpoN* inhibition cannot be overridden at all loci with RpoN promoters.

Similarly, the metabolism of certain amino acids is under RpoN regulation, but the RpoN molecular roadblock did not affect the transcription of the catabolic genes for some of these compounds. For example, P. aeruginosa prefers to consume proline, alanine, arginine and glutamate (36). The microarray results from our study support this trend. Genes necessary for the degradation of histidine, branched chain and aromatic amino acids were significantly downregulated whereas gene expression was unchanged for the catabolism of more favorable substrates, i.e., proline, alanine and arginine. The metabolism of these three amino acids requires RpoN and the EBP CbrB but is also regulated by other transcription factors. Transcriptional activation by these other regulators and native RpoN:RNAP most likely weakened the inhibitory effect of RpoN*. More sensitive detection methods such as qPCR can be used to measure transcriptional changes at suspected RpoN control points where competition between the RpoN molecular roadblock and the native RpoN:RNAP is occurring.

This example describes the development and successful application of a DNA-binding protein (RpoN molecular roadblock) that specifically targets the −24 element of the promoter of the global transcriptional regulator RpoN to interrogate and redefine the RpoN regulon of P. aeruginosa. The RpoN molecular roadblock is a compelling tool that will allow researchers to define the RpoN regulon of any bacterium. The −24 element of an RpoN promoter is comprised of only seven nucleotides, so it was reasonable to suspect that this DNA binding protein or RpoN molecular roadblock would interact with this motif throughout the genome of any given bacterium. However, expression of the RpoN molecular roadblock in P. aeruginosa targeted and affected transcription of only genes under RpoN control. We did not observe any random perturbations in transcription for genes that could not be linked to RpoN regulation. The RpoN molecular roadblock does not interact with the −12 element of RpoN promoters and has conclusively been shown to bind specifically to the consensus sequence of the −24 element. How much nucleotide variation is allowed before the RpoN molecular roadblock no longer interacts with the −24 element? The answer to this question will not only define how RpoN mediated transcription depends on the magnitude of the interaction between RpoN and the −24 element, but will allow us to strengthen the substrate specificity of RpoN molecular roadblock.

Due to the universal nature of RpoN transcription, the RpoN molecular roadblock can be used across numerous bacterial species to completely map out their respective RpoN regulatory networks. The inducible expression of RpoN* allows for the first time the ability to assess RpoN regulation at any instant during a bacterium's life cycle. It is now possible to measure RpoN regulation in a temporal manner, which could not be ascertained before, and therefore will allow us to discover RpoN-mediated responses that occur during biofilm formation or that are necessary for infection in patients with cystic fibrosis. The RpoN molecular roadblock can be employed in bacteria in which it is not possible to generate rpoN-deficient strains, and combined with transcriptomic studies as outlined here, will shed some light on the essentiality of RpoN regulation within these unusual microorganisms. Microarray analysis illustrated the use of the RpoN molecular roadblock for defining the RpoN regulon of P. aeruginosa. RpoN molecular roadblock binding to the −24 RpoN promoter element resulted in interference with transcription from RpoN promoters and all sites of RpoN control were readily identified. Interestingly, RpoN was found to control a genetic network that was responsible for processing a wealth of environmental responses and information. Expression of the RpoN molecular roadblock under different conditions and stresses in P. aeruginosa will enable us to completely define the genetic network for this global transcriptional regulator.

REFERENCES AND NOTES

1. Barrios H, Valderrama B, & Morett E (1999) Compilation and analysis of sigma(54)-dependent promoter sequences. *Nucleic acids research* 27(22):4305-4313.
2. Chen B, et al. (2007) ATP ground- and transition states of bacterial enhancer binding AAA+ ATPases support complex formation with their target protein, sigma54. *Structure* 15(4):429-440.
3. Totten P A, Lara J C, & Lory S (1990) The rpoN gene product of *Pseudomonas aeruginosa* is required for expression of diverse genes, including the flagellin gene. *Journal of bacteriology* 172(1):389-396.
4. Köhler T, Harayama S, Ramos J L, & Timmis K N (1989) Involvement of *Pseudomonas putida* RpoN sigma factor in regulation of various metabolic functions. *Journal of bacteriology* 171(8):4326-4333.
5. Giglio K M, Eisenstatt J, & Garza A G (2010) Identification of enhancer binding proteins important for *Myxococcus xanthus* development. *Journal of bacteriology* 192:360-364.
6. Jones J, Studholme D J, Knight C G, & Preston G M (2007) Integrated bioinformatic and phenotypic analysis of RpoN-dependent traits in the plant growth-promoting bacterium *Pseudomonas fluorescens* SBW25. *Environmental microbiology* 9(12):3046-3064.
7. Fisher M A, et al. (2005) *Borrelia burgdorferi* sigma54 is required for mammalian infection and vector transmission but not for tick colonization. *Proceedings of the National Academy of Sciences of the United States of America* 102 (14):5162-5167.
8. Iannino F, Ugalde R A, & Inon de Iannino N (2008) Characterization of *Brucella abortus* sigma factor sigma54 (rpoN): genetic complementation of *Sinorhizobium meliloti* ntrA mutant. *Microb Pathog* 45(5-6):394-402.
9. Hendrickson E L, Plotnikova J, Mahajan-Miklos S, Rahme L G, & Ausubel F M (2001) Differential roles of the *Pseudomonas aeruginosa* PA14 rpoN gene in pathogenicity in plants, nematodes, insects, and mice. *Journal of bacteriology* 183(24):7126-7134.
10. Savioz A, Zimmermann A, & Haas D (1993) *Pseudomonas aeruginosa* promoters which contain a conserved GG-N10-GC motif but appear to be RpoN-independent. *Mol Gen Genet.* 238(1-2):74-80.
11. Boucher J C, Schurr M J, & Deretic V (2000) Dual regulation of mucoidy in *Pseudomonas aeruginosa* and sigma factor antagonism. *Molecular microbiology* 36(2): 341-351.
12. Dong T, Yu R, & Schellhorn H (2011) Antagonistic regulation of motility and transcriptome expression by RpoN and RpoS in *Escherichia coli*. *Molecular microbiology* 79(2):375-386.
13. Reitzer L & Schneider B L (2001) Metabolic context and possible physiological themes of sigma(54)-dependent genes in *Escherichia coli*. *Microbiology and molecular biology reviews: MMBR* 65(3):422-444.
14. Merrick M (1993) In a class of its own—the RNA polymerase sigma factor σ54 (σN). *Molecular microbiology* 10(5):903-909.

15. Doucleff M, Pelton J G, Lee P S, Nixon B T, & Wemmer D E (2007) Structural basis of DNA recognition by the alternative sigma-factor, sigma54. *Journal of molecular biology* 369(4):1070-1078.
16. Jishage M, Kvint K, Shingler V, & Nystrom T (2002) Regulation of sigma factor competition by the alarmone ppGpp. *Genes & development* 16(10):1260-1270.
17. Dasgupta N, et al. (2003) A four-tiered transcriptional regulatory circuit controls flagellar biogenesis in *Pseudomonas aeruginosa. Molecular microbiology* 50(3): 809-824.
18. Wang L & Gralla J D (2001) Roles for the C-terminal region of sigma 54 in transcriptional silencing and DNA binding. *The Journal of biological chemistry* 276(12): 8979-8986.
19. Studholme D J, Buck M, & Nixon T (2000) Identification of potential sigma(N)-dependent promoters in bacterial genomes. *Microbiology* 146 Pt 12:3021-3023.
20. Magasanik B (1993) The regulation of nitrogen utilization in enteric bacteria. *J Cell Biochem* 51(1):34-40.
21. Palmer G C, Palmer K L, Jorth P A, & Whiteley M (2010) Characterization of the *Pseudomonas aeruginosa* transcriptional response to phenylalanine and tyrosine. *Journal of bacteriology* 192(11):2722-2728.
22. Singh B & Röhm K (2008) Characterization of a *Pseudomonas putida* ABC transporter (AatJMQP) required for acidic amino acid uptake: biochemical properties and regulation by the Aau two-component system. *Microbiology* 154(3):797-809.
23. Nishiyo T, Haas D, & Itoh Y (2001) The CbrA-CbrB two-component regulatory system controls the utilization of multiple carbon and nitrogen sources in *Pseudomonas aeruginosa. Molecular microbiology* 40(4):917-931.
24. Li W & Lu C D (2007) Regulation of carbon and nitrogen utilization by CbrAB and NtrBC two-component systems in *Pseudomonas aeruginosa. Journal of bacteriology* 189 (15):5413-5420.
25. Valentini M, Storelli N, & Lapouge K (2011) Identification of C(4)-dicarboxylate transport systems in *Pseudomonas aeruginosa* PAO1. *Journal of bacteriology* 193(17): 4307-4316.
26. Lu C D, Itoh Y, Nakada Y, & Jiang Y (2002) Functional analysis and regulation of the divergent spuABCDEFGH-spuI operons for polyamine uptake and utilization in *Pseudomonas aeruginosa* PAO1. *Journal of bacteriology* 184(14):3765-3773.
27. Hwang S, Jeon B, Yun J, & Ryu S (2011) Roles of RpoN in the resistance of *Campylobacter jejuni* under various stress conditions. *BMC microbiology* 11:207.
28. Kim H, Lee M, Chun S, Park S, & Lee K (2007) Role of NtrC in biofilm formation via controlling expression of the gene encoding an ADP-glycero-manno-heptose-6-epimerase in the pathogenic bacterium, *Vibrio vulnificus. Molecular microbiology* 63(2):559-574.
29. Dubern J F & Diggle S P (2008) Quorum sensing by 2-alkyl-4-quinolones in *Pseudomonas aeruginosa* and other bacterial species. *Molecular bioSystems* 4(9):882-888.
30. Schuster M & Greenberg E P (2006) A network of networks: quorum-sensing gene regulation in *Pseudomonas aeruginosa. International journal of medical microbiology: IJMM* 296(2-3):73-81.
31. Schuster M, Hawkins A C, Harwood C S, & Greenberg E P (2004) The *Pseudomonas aeruginosa* RpoS regulon and its relationship to quorum sensing. *Molecular microbiology* 51(4):973-985.
32. Heurlier K, Dénervaud V, Pessi G, Reimmann C, & Haas D (2003) Negative control of quorum sensing by RpoN (sigma54) in *Pseudomonas aeruginosa* PAO1. *Journal of bacteriology* 185(7):2227-2235.
33. Fiske M J, Whitaker R J, & Jensen R A (1983) Hidden overflow pathway to L-phenylalanine in *Pseudomonas aeruginosa. Journal of bacteriology* 154(2):623-631.
34. Lindsey T L, Hagins J M, Sokol P A, & Siloh-Suh L A (2008) Virulence determinants from a cystic fibrosis isolate of *Pseudomonas aeruginosa* include isocitrate lyase. *Microbiology* 154:1616-1627.
35. Trunk K, et al. (2010) Anaerobic adaptation in *Pseudomonas aeruginosa*: definition of the Anr and Dnr regulons. *Environmental microbiology* 12(6):1719-1733.
36. Palmer K, Aye L, & Whitely M (2007) Nutritional cues control *Pseudomonas aeruginosa* multicellular behavior in cystic fibrosis sputum. *Journal of bacteriology* 189(22): 8079-8087.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09392790B2). An electronic copy of the "Sequence Listing" will also be available from the USPTO upon request and payment of the fee set forth in 37 CFR 1.19(b)(3).

What is claimed is:

1. A method for repressing transcription or gene expression from a binding site of interest, wherein the binding site of interest is an RpoN binding site or a cryptic promoter upstream or downstream of an RpoN binding site, comprising the steps of:
    (a) providing an agent wherein the agent:
        (i) specifically and selectively binds to a sequence comprised in the binding site of interest,
        (ii) inhibits or represses expression of genes regulated by the binding site of interest, and
        (iii) comprises a heterologous protein comprising a sequence selected from the group consisting of SEQ ID NOS. 10000-10093; and
    (b) contacting the agent to the binding site of interest.

2. The method of claim 1, wherein said contacting comprises contacting the agent to a bacterial cell comprising the binding site of interest, wherein the agent is heterologous to the bacterial cell.

3. The method of claim 1, wherein the agent binds specifically to a −24, −12, or −24/−12 site for RpoN promoter interference.

4. The method of claim 1, wherein the RpoN binding site comprises a sequence selected from the group consisting of SEQ ID NOS. 1-9999 and the 3' to 5' complementary base pairs thereof.

5. The method of claim 1, wherein the agent comprises a $\sigma^{54}$ ("sig54") protein.

6. The method of claim 5, wherein the agent is provided by heterologously expressing the $\sigma^{54}$ ("sig54") protein.

7. The method of claim 1, wherein the agent comprises an RpoN protein comprising a modification to the heptad repeat overlapping the glutamine-rich or acid-rich motifs.

8. The method of claim 1, wherein the agent binds specifically and selectively to the cryptic promoter.

9. The method of claim 1, wherein the agent is a synthetic peptide from 20 to 600 amino acids in length.

10. The method of claim 9, wherein the synthetic peptide comprises at least 20 carboxy terminal amino acids of an RpoN protein.

11. The method of claim 9, wherein the synthetic peptide comprises the conserved amino acids from an RpoN box of Region III of an RpoN protein through the carboxy terminal amino acid residue of the RpoN protein.

12. The method of claim 9, wherein the synthetic peptide has 70-75%, 75-80%, 80-85%, 85-90%, 90-95% or 95-100% homology with an RpoN box of Region III of an RpoN protein.

13. The method of claim 11, wherein Region III comprises a modification of the heptad repeat overlapping the glutamine-rich or acid-rich motifs.

* * * * *